(12) United States Patent
Wood et al.

(10) Patent No.: US 8,372,859 B2
(45) Date of Patent: Feb. 12, 2013

(54) CGRP RECEPTOR ANTAGONISTS WITH TERTIARY AMIDE, SULFONAMIDE, CARBAMATE AND UREA END GROUPS

(75) Inventors: Michael R. Wood, Harleysville, PA (US); June Kim, Collegeville, PA (US); Melody McWherter, Boyertown, PA (US); Harold G. Selnick, Ambler, PA (US); Kathy Schirripa, Quakertown, PA (US)

(73) Assignee: Merck, Sharp & Dohme Corp., Rahway, NJ (US)

( * ) Notice: Subject to any disclaimer, the term of this patent is extended or adjusted under 35 U.S.C. 154(b) by 359 days.

(21) Appl. No.: 12/594,993

(22) PCT Filed: Apr. 7, 2008

(86) PCT No.: PCT/US2008/004528
§ 371 (c)(1),
(2), (4) Date: May 27, 2010

(87) PCT Pub. No.: WO2008/127584
PCT Pub. Date: Oct. 23, 2008

(65) Prior Publication Data
US 2010/0292263 A1   Nov. 18, 2010

Related U.S. Application Data

(60) Provisional application No. 60/922,929, filed on Apr. 11, 2007.

(51) Int. Cl.
*A61K 31/44* (2006.01)
*A01N 43/50* (2006.01)
(52) U.S. Cl. ........................................ 514/278; 514/385
(58) Field of Classification Search ............................. None
See application file for complete search history.

(56) References Cited

U.S. PATENT DOCUMENTS

| | | |
|---|---|---|
| 7,189,722 B2 | 3/2007 | Bell et al. |
| 7,192,954 B2 | 3/2007 | Bell et al. |
| 7,202,251 B2 | 4/2007 | Bell et al. |
| 7,390,798 B2 | 6/2008 | Williams et al. |
| 2003/0114465 A1 | 6/2003 | Stamford et al. |
| 2008/0004304 A1 | 1/2008 | Bell et al. |
| 2008/0096878 A1 | 4/2008 | Bell et al. |
| 2008/0214511 A1 | 9/2008 | Bell et al. |
| 2009/0054408 A1 | 2/2009 | Bell et al. |

FOREIGN PATENT DOCUMENTS

| | | |
|---|---|---|
| WO | 2006031676 A2 | 3/2006 |
| WO | WO 2006/031513 * | 3/2006 |
| WO | 2008020902 A1 | 2/2008 |
| WO | 2008112159 A2 | 9/2008 |

OTHER PUBLICATIONS

International Search Report for PCT/US2008/04528.

* cited by examiner

*Primary Examiner* — Craig Ricci
(74) *Attorney, Agent, or Firm* — Nicole M. Beeler; Gerard M. Devlin

(57) ABSTRACT

Compounds of formula I:

(I)

$$\text{structure with } R^f, R^e, R^4, E^c, E^a, E^b, A, m, n, J, Y, R^{PG}$$

(wherein variables A, m, n, J, $R^e$, $R^f$, $R^4$, $E^a$, $E^b$, $E^c$, $R^{PG}$ and Y are as described herein) which are antagonists of CGRP receptors and which are useful in the treatment or prevention of diseases in which the CGRP is involved, such as migraine; and pharmaceutical compositions comprising these compounds and the use of these compounds and compositions in the prevention or treatment of such diseases in which CGRP is involved.

4 Claims, No Drawings

CGRP RECEPTOR ANTAGONISTS WITH TERTIARY AMIDE, SULFONAMIDE, CARBAMATE AND UREA END GROUPS

CROSS-REFERENCE TO RELATED APPLICATIONS

This application claims priority under 35 U.S.C. §119(e) of U.S. provisional application Ser. No. 60/922,929, filed Apr. 11, 2007.

BACKGROUND OF THE INVENTION

CGRP (Calcitonin Gene-Related Peptide) is a naturally occurring 37-amino acid peptide that is generated by tissue-specific alternate processing of calcitonin messenger RNA and is widely distributed in the central and peripheral nervous system. CGRP is localized predominantly in sensory afferent and central neurons and mediates several biological actions, including vasodilation. CGRP is expressed in alpha- and beta-forms that vary by one and three amino acids in the rat and human, respectively. CGRP-alpha and CGRP-beta display similar biological properties. When released from the cell, CGRP initiates its biological responses by binding to specific cell surface receptors that are predominantly coupled to the activation of adenylyl cyclase. CGRP receptors have been identified and pharmacologically evaluated in several tissues and cells, including those of brain, cardiovascular, endothelial, and smooth muscle origin.

Based on pharmacological properties, these receptors are divided into at least two subtypes, denoted $CGRP_1$ and $CGRP_2$. Human α-CGRP-(8-37), a fragment of CGRP that lacks seven N-terminal amino acid residues, is a selective antagonist of $CGRP_1$, whereas the linear analogue of CGRP, diacetoamido methyl cysteine CGRP ([Cys(ACM)2,7] CGRP), is a selective agonist of $CGRP_2$. CGRP is a potent neuromodulator that has been implicated in the pathology of cerebrovascular disorders such as migraine and cluster headache. In clinical studies, elevated levels of CGRP in the jugular vein were found to occur during migraine attacks (Goadsby et al., Ann. Neurol., 1990, 28, 183-187), salivary levels of CGRP are elevated in migraine subjects between attacks (Bellamy et al., Headache, 2006, 46, 24-33), and CGRP itself has been shown to trigger migrainous headache (Lassen et al., Cephalalgia, 2002, 22, 54-61). In clinical trials, the CGRP antagonist BIBN4096BS has been shown to be effective in treating acute attacks of migraine (Olesen et al., New Engl. J. Med., 2004, 350, 1104-1110) and was able to prevent headache induced by CGRP infusion in a control group (Petersen et al., Clin. Pharmacol. Ther., 2005, 77, 202-213).

CGRP-mediated activation of the trigeminovascular system may play a key role in migraine pathogenesis. Additionally, CGRP activates receptors on the smooth muscle of intracranial vessels, leading to increased vasodilation, which is thought to contribute to headache pain during migraine attacks (Lance, Headache Pathogenesis: Monoamines, Neuropeptides, Purines and Nitric Oxide, Lippincott-Raven Publishers, 1997, 3-9). The middle meningeal artery, the principle artery in the dura mater, is innervated by sensory fibers from the trigeminal ganglion which contain several neuropeptides, including CGRP. Trigeminal ganglion stimulation in the cat resulted in increased levels of CGRP, and in humans, activation of the trigeminal system caused facial flushing and increased levels of CGRP in the external jugular vein (Goadsby et al., Ann. Neurol., 1988, 23, 193-196). Electrical stimulation of the dura mater in rats increased the diameter of the middle meningeal artery, an effect that was blocked by prior administration of CGRP(8-37), a peptide CGRP antagonist (Williamson et al., Cephalalgia, 1997, 17, 525-531). Trigeminal ganglion stimulation increased facial blood flow in the rat, which was inhibited by CGRP(8-37) (Escott et al., Brain Res. 1995, 669, 93-99). Electrical stimulation of the trigeminal ganglion in marmoset produced an increase in facial blood flow that could be blocked by the non-peptide CGRP antagonist BIBN4096BS (Doods et al., Br. J. Pharmacol., 2000, 129, 420-423). Thus the vascular effects of CGRP may be attenuated, prevented or reversed by a CGRP antagonist.

CGRP-mediated vasodilation of rat middle meningeal artery was shown to sensitize neurons of the trigeminal nucleus caudalis (Williamson et al., The CGRP Family: Calcitonin Gene-Related Peptide (CGRP), Amylin, and Adrenomedullin, Landes Bioscience, 2000, 245-247). Similarly, distention of dural blood vessels during migraine headache may sensitize trigeminal neurons. Some of the associated symptoms of migraine, including extra-cranial pain and facial allodynia, may be the result of sensitized trigeminal neurons (Burstein et al., Ann. Neurol. 2000, 47, 614-624). A CGRP antagonist may be beneficial in attenuating, preventing or reversing the effects of neuronal sensitization.

The ability of the compounds of the present invention to act as CGRP antagonists makes them useful pharmacological agents for disorders that involve CGRP in humans and animals, but particularly in humans. Such disorders include migraine and cluster headache (Doods, Curr Opin Inves Drugs, 2001, 2 (9), 1261-1268; Edvinsson et al., Cephalalgia, 1994, 14, 320-327); chronic tension type headache (Ashina et al., Neurology, 2000, 14, 1335-1340); pain (Yu et al., Eur. J. Pharm., 1998, 347, 275-282); chronic pain (Hulsebosch et al., Pain, 2000, 86, 163-175); neurogenic inflammation and inflammatory pain (Holzer, Neurosci., 1988, 24, 739-768; Delay-Goyet et al., Acta Physiol. Scanda. 1992, 146, 537-538; Salmon et al., Nature Neurosci., 2001, 4(4), 357-358); eye pain (May et al. Cephalalgia, 2002, 22, 195-196), tooth pain (Awawdeh et al., Int. Endocrin. J., 2002, 35, 30-36), non-insulin dependent diabetes mellitus (Molina et al., Diabetes, 1990, 39, 260-265); vascular disorders; inflammation (Zhang et al., Pain, 2001, 89, 265), arthritis, bronchial hyperreactivity, asthma, (Foster et al., Ann. NY Acad. Sci., 1992, 657, 397-404; Schini et al., Am. J. Physiol., 1994, 267, H2483-H2490; Zheng et al., J. Virol., 1993, 67, 5786-5791); shock, sepsis (Beer et al., Crit. Care Med., 2002, 30 (8), 1794-1798); opiate withdrawal syndrome (Salmon et al., Nature Neurosci., 2001, 4(4), 357-358); morphine tolerance (Menard et al., J. Neurosci., 1996, 16 (7), 2342-2351); hot flashes in men and women (Chen et al., Lancet, 1993, 342, 49; Spetz et al., J. Urology, 2001, 166, 1720-1723); allergic dermatitis (Wallengren, Contact Dermatitis, 2000, 43 (3), 137-143); psoriasis; encephalitis, brain trauma, ischaemia, stroke, epilepsy, and neurodegenerative diseases (Rohrenbeck et al., Neurobiol. of Disease 1999, 6, 15-34); skin diseases (Geppetti and Holzer, Eds., Neurogenic Inflammation, 1996, CRC Press, Boca Raton, Fla.), neurogenic cutaneous redness, skin rosaceousness and erythema; tinnitus (Herzog et al., J. Membrane Biology, 2002, 189(3), 225); inflammatory bowel disease, irritable bowel syndrome, (Hoffman et al. Scandinavian Journal of Gastroenterology, 2002, 37(4) 414-422) and cystitis. Of particular importance is the acute or prophylactic treatment of headache, including migraine and cluster headache.

The present invention relates to compounds that are useful as ligands for CGRP receptors, in particular antagonists for CGRP receptors, processes for their preparation, their use in therapy, pharmaceutical compositions comprising them and methods of therapy using them.

SUMMARY OF THE INVENTION

The present invention is directed to compounds of the formula I:

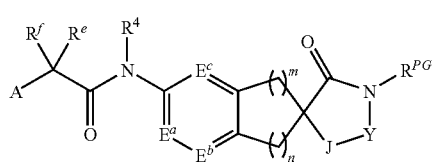

(I)

(wherein variables A, m, n, J, $R^e$, $R^f$, $R^4$, $E^a$, $E^b$, $E^c$, $R^{PG}$ and Y are as described herein) which are antagonists of CGRP receptors and which are useful in the treatment or prevention of diseases in which the CGRP is involved, such as migraine. The invention is also directed to pharmaceutical compositions comprising these compounds and the use of these compounds and compositions in the prevention or treatment of such diseases in which CGRP is involved.

DETAILED DESCRIPTION OF THE INVENTION

The present invention is directed to compounds of the formula I:

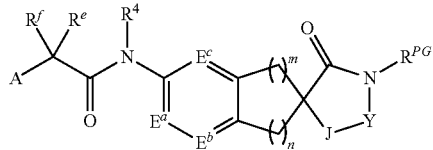

wherein:
A is independently selected from:

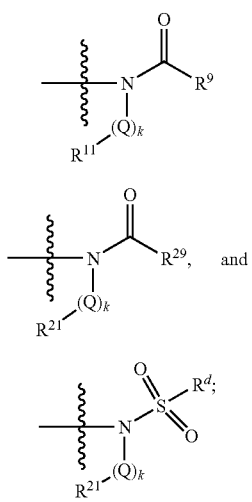

Q is independently selected from:
(1) —$CH_2$—,
(2) —$CHR^d$—
(3) —$C(R^d)_2$—,
(4) —$C(halo)R^a$—, and
(5) —$C(halo)_2$-;

each k is 0, 1, 2, or 3, with the understanding that when k=0, this represents a direct bond between the two adjacent groups;
$R^4$ is independently selected from:
   (1) hydrogen,
   (2) —$C_{1-6}$alkyl, which is unsubstituted or substituted with 1-5 substituents each independently selected from:
      (a) halo,
      (b) —$C_{3-6}$cycloalkyl,
      (c) —$CF_3$, and
      (d) —O—$R^a$,
   (3) —$C_{3-6}$cycloalkyl,
   (4) benzyl, and
   (5) phenyl;
$E^a$ is selected from:
   (1) —$C(R^{5a})$=,
   (2) —N=, and
   (3) —($N^+$—$O^-$)=;
$E^b$ is selected from:
   (1) —$C(R^{5b})$=,
   (2) —N=, and
   (3) —($N^+$—$O^-$)=;
$E^c$ is selected from:
   (1) —$C(R^{5c})$=,
   (2) —N=, and
   (3) —($N^+$—$O^-$)=;
$R^{5a}$, $R^{5b}$ and $R^{5c}$ are each independently selected from:
   (1) hydrogen,
   (2) —$C_{1-6}$alkyl, which is unsubstituted or substituted with 1-6 halo,
   (3) halo,
   (4) —$OR^a$, and
   (5) —CN;
$R^9$ is independently selected from:
   (1) —$C_1$alkyl, optionally substituted with 1-2 fluoro, and further substituted with 1-3 substituents which are each independently selected from:
      (a) chloro,
      (b) bromo,
      (c) iodo,
      (d) —$OR^a$,
      (e) —CN,
      (f) —$CO_2R^a$,
      (g) —C(=O)$NR^bR^c$,
      (h) —$S(O)_xR^d$;
      (i) —$C_{3-6}$cycloalkyl, which is unsubstituted or substituted with 1-6 halo,
      (j) —$NR^bR^c$,
      (k) —O—$CO_2R^d$,
      (l) —C≡C—$R^a$,
      (m) —N($R^b$)—$CO_2R^d$,
      (n) —N($R^b$)—$SO_2R^d$,
      (o) —C(=O)$R^a$,
      (p) —O—C(=O)$R^a$,
      (q) oxo,
      (r) —N($R^b$)—C(=O)$R^a$, and
      (s) heterocycle, wherein heterocycle is selected from; pyridyl, pyrimidinyl, pyrazinyl, pyridazinyl, piperidyl, piperazinyl, pyrrolidinyl, thienyl, morpholinyl, thiazolyl, oxazolyl, isoxazolyl, furanyl, tetrahydrofuranyl, and tetrahydropyranyl, which heterocycle is unsubstituted or substituted with 1-5 substituents each independently selected from:
         (i) halo,
         (ii) —$OR^a$,
         (iii) —CN,
         (iv) —$CO_2R^a$, (v) —$C_{1-6}$alkyl, which is optionally substituted with 1-6 halo,
(vi) —C(=O)NR$^b$R$^c$,
(vii) —S(O)$_v$R$^d$;
(viii) —$C_{3-6}$cycloalkyl, which optionally substituted with 1-6 halo,
(ix) —NR$^b$R$^c$,
(x) —O—CO$_2$R$^d$,
(xi) —C≡C—R$^a$,
(xii) —N(R$^b$)—CO$_2$R$^d$,
(xiii) —N(R$^b$)—SO$_2$R$^d$,
(xiv) —C(=O)R$^a$,
(xv) —O—C(=O)R$^a$,
(xvi) oxo, and
(xvii) —N(R$^b$)—C(=O)R$^a$, (2) —$C_{2-8}$alkyl, optionally substituted with 1-6 fluoro, and further substituted with 1-5 substituents each independently selected from:
(a) chloro,
(b) bromo,
(c) iodo,
(d) —OR$^a$,
(e) —CN,
(f) —CO$_2$R$^a$,
(g) —C(=O)NR$^b$R$^c$,
(h) —S(O)$_v$R$^d$;
(i) —$C_{3-6}$cycloalkyl, which is unsubstituted or substituted with 1-6 halo,
(j) —NR$^b$R$^c$,
(k) —O—CO$_2$R$^d$,
(l) —C≡C—R$^a$,
(m) —N(R$^b$)—CO$_2$R$^d$,
(n) —N(R$^b$)—SO$_2$R$^d$,
(o) —C(=O)R$^a$,
(p) —O—C(=O)R$^a$,
(q) oxo,
(r) —N(R$^b$)—C(=O)R$^a$, and
(s) phenyl or heterocycle, wherein heterocycle is selected from: pyridyl, pyrimidinyl, pyrazinyl, pyridazinyl, piperidyl, piperazinyl, pyrrolidinyl, thienyl, morpholinyl, thiazolyl, oxazolyl, isoxazolyl, furanyl, tetrahydrofuranyl, and tetrahydropyranyl, which phenyl or heterocycle is unsubstituted or substituted with 1-5 substituents each independently selected from:
(i) halo,
(ii) —OR$^a$,
(iii) —CN,
(iv) —CO$_2$R$^a$,
(v) —$C_{1-6}$alkyl, which is optionally substituted with 1-6 halo,
(vi) —C(=O)NR$^b$R$^c$,
(vii) —S(O)$_v$R$^d$;
(viii) —$C_{3-6}$cycloalkyl, which optionally substituted with 1-6 halo,
(ix) —NR$^b$R$^c$,
(x) —O—CO$_2$R$^d$,
(xi) —C≡C—R$^a$,
(xii) —N(R$^b$)—CO$_2$R$^d$,
(xiii) —N(R$^b$)—SO$_2$R$^d$,
(xiv) —C(=O)R$^a$,
(xv) —O—C(=O)R$^a$,
(xvi) oxo, and
(xvii) —N(R$^b$)—C(=O)R$^a$, (3) benzyl or phenyl, substituted with 1-5 substituents each independently selected from:
(a) halo,
(b) —OR$^a$,
(c) —CN,
(d) —CO$_2$R$^a$,
(e) —$C_{1-6}$alkyl, which is unsubstituted or substituted with 1-6 halo,
(f) —C(=O)NR$^b$R$^c$,
(g) —S(O)$_v$R$^d$;
(h) —$C_{3-6}$cycloalkyl, which is unsubstituted or substituted with 1-6 halo,
(i) —NR$^b$R$^c$,
(j) —O—CO$_2$R$^d$,
(k) —C≡C—R$^a$,
(l) —N(R$^b$)—CO$_2$R$^d$,
(m) —N(R$^b$)—SO$_2$R$^d$,
(n) —C(=O)R$^a$,
(o) —O—C(=O)R$^a$,
(p) oxo,
(q) —N(R$^b$)—C(=O)R$^a$, and
(r) phenyl or heterocycle, wherein heterocycle is selected from; pyridyl, pyrimidinyl, pyrazinyl, pyridazinyl, piperidyl, piperazinyl, pyrrolidinyl, thienyl, morpholinyl, thiazolyl, oxazolyl, isoxazolyl, furanyl, tetrahydrofuranyl, and tetrahydropyranyl, which phenyl or heterocycle is unsubstituted or substituted with 1-5 substituents each independently selected from:
(i) halo,
(ii) —OR$^a$,
(iii) —CN,
(iv) —CO$_2$R$^a$,
(v) —$C_{1-6}$alkyl, which is optionally substituted with 1-6 halo,
(vi) —C(=O)NR$^b$R$^c$,
(vii) —S(O)$_v$R$^d$;
(viii) —$C_{3-6}$cycloalkyl, which optionally substituted with 1-6 halo,
(ix) —NR$^b$R$^c$,
(x) —O—CO$_2$R$^d$,
(xi) —C≡C—R$^a$,
(xii) —N(R$^b$)—CO$_2$R$^d$,
(xiii) —N(R$^b$)—SO$_2$R$^d$,
(xiv) —C(=O)R$^a$,
(xv) —O—C(=O)R$^a$,
(xvi) oxo, and
(xvii) —N(R$^b$)—C(=O)R$^a$, (4) a group independently selected from: naphthyl, tetrahydronaphthyl, indanyl, biphenyl, phenanthryl, anthryl, azepinyl, azepanyl, azetidinyl, benzimidazolyl, benzisoxazolyl, benzofuranyl, benzofurazanyl, benzopyranyl, benzothiopyranyl, benzofuryl, benzothiazolyl, benzothienyl, benzoxazolyl, benzopyrazolyl, benzotriazolyl, chromanyl, cinnolinyl, dibenzofuranyl, dihydrobenzofuryl, dihydrobenzothienyl, dihydrobenzothiopyranyl, dihydrobenzothiopyranyl sulfone, furyl, furanyl, imidazolidinyl, imidazolinyl, imidazolyl, indolinyl, indolyl, isochromanyl, isoindolinyl, isoquinolinyl, isothiazolidinyl, isothiazolyl, morpholinyl, naphthyridinyl, oxadiazolyl, 2-oxoazepinyl, 4-oxonaphthyridinyl, 2-oxopiperazinyl, 2-oxopiperidinyl, 2-oxopyrrolidinyl, 2-oxopyridyl, 2-oxoquinolinyl, piperidyl, piperazinyl, pyrazinyl, pyrazolidinyl, pyrazolyl, pyridazinyl, pyridinyl, pyridyl, pyrimidinyl, pyrimidyl, pyrrolidinyl, pyrrolyl, quinazolinyl, quinolinyl, quinoxalinyl, tetrahydrofuranyl, tetrahydrofuryl, tetrahydroimidazopyridinyl, tetrahydroisoquinolinyl, tetrahydroquinolinyl, tetrazolyl, thiamorpholinyl, thiamorpholinyl sulfoxide, thiamorpholinyl sulfone, thiazolyl, thiazolinyl, thienofuryl, thienothienyl, thienyl, triazolyl, isoxazolyl, tetrahydrothienyl, tetrahydropyranyl, oxetanyl, tetrahydrothiapyranyl, and thietanyl, which group is unsubstituted or substituted with 1-5 substituents each independently selected from:
(a) halo,
(b) —$OR^a$,
(c) —CN,
(d) —$CO_2R^a$,
(e) —$C_{1-6}$alkyl, which is unsubstituted or substituted with 1-6 halo,
(f) —C(=O)$NR^bR^c$,
(g) —S(O)$_vR^d$;
(h) —$C_{3-6}$cycloalkyl, which is unsubstituted or substituted with 1-6 halo,
(i) —$NR^bR^c$,
(j) —O—$CO_2R^d$,
(k) —C≡C—$R^a$,
(l) —N($R^b$)—$CO_2R^d$,
(m) —N($R^b$)—$SO_2R^d$,
(n) —C(=O)$R^a$,
(o) —O—C(=O)$R^a$,
(p) oxo,
(q) —N($R^b$)—C(=O)$R^a$, and
(r) phenyl or heterocycle, wherein heterocycle is selected from; pyridyl, pyrimidinyl, pyrazinyl, pyridazinyl, piperidyl, piperazinyl, pyrrolidinyl, thienyl, morpholinyl, thiazolyl, oxazolyl, isoxazolyl, furanyl, tetrahydrofuranyl, and tetrahydropyranyl, which phenyl or heterocycle is unsubstituted or substituted with 1-5 substituents each independently selected from:
(i) halo,
(ii) —$OR^a$,
(iii) —CN,
(iv) —$CO_2R^a$,
(v) —$C_{1-6}$alkyl, which is optionally substituted with 1-6 halo,
(vi) —C(=O)$NR^bR^c$,
(vii) —S(O)$_vR^d$;
(viii) —$C_{3-6}$cycloalkyl, which optionally substituted with 1-6 halo,
(ix) —$NR^bR^c$,
(x) —O—$CO_2R^d$,
(xi) —C≡C—$R^a$,
(xii) —N($R^b$)—$CO_2R^d$,
(xiii) —N($R^b$)—$SO_2R^d$,
(xiv) —C(=O)$R^a$,
(xv) —O—C(=O)$R^a$,
(xvi) oxo, and
(xvii) —N($R^b$)—C(=O)$R^a$, (5) —$C_3$cycloalkyl, —$C_4$cycloalkyl or —$C_7$cycloalkyl, unsubstituted or substituted with 1-5 substituents each independently selected from:
(a) halo,
(b) —$OR^a$,
(c) —CN,
(d) —$CO_2R^a$,
(e) —$C_{1-6}$alkyl, which is unsubstituted or substituted with 1-6 halo,
(f) —C(=O)$NR^bR^c$,
(g) —S(O)$_vR^d$;
(h) —$C_{3-6}$cycloalkyl, which is unsubstituted or substituted with 1-6 halo,
(i) —$NR^bR^c$,
(j) —O—$CO_2R^d$,
(k) —C≡C—$R^a$,
(l) —N($R^b$)—$CO_2R^d$,
(m) —N($R^b$)—$SO_2R^d$,
(n) —C(=O)$R^a$,
(o) —O—C(=O)$R^a$,
(p) oxo,
(q) —N($R^b$)—C(=O)$R^a$, and
(r) phenyl or heterocycle, wherein heterocycle is selected from; pyridyl, pyrimidinyl, pyrazinyl, pyridazinyl, piperidyl, piperazinyl, pyrrolidinyl, thienyl, morpholinyl, thiazolyl, oxazolyl, isoxazolyl, furanyl, tetrahydrofuranyl, and tetrahydropyranyl, which phenyl or heterocycle is unsubstituted or substituted with 1-5 substituents each independently selected from:
(i) halo,
(ii) —$OR^a$,
(iii) —CN,
(iv) —$CO_2R^a$,
(v) —$C_{1-6}$alkyl, which is optionally substituted with 1-6 halo,
(vi) —C(=O)$NR^bR^c$,
(vii) —S(O)$_vR^d$;
(viii) —$C_{3-6}$cycloalkyl, which optionally substituted with 1-6 halo,
(ix) —$NR^bR^c$,
(x) —O—$CO_2R^d$,
(xi) —C≡C—$R^a$,
(xii) —N($R^b$)—$CO_2R^d$,
(xiii) —N($R^b$)—$SO_2R^d$,
(xiv) —C(=O)$R^a$,
(xv) —O—C(=O)$R^a$,
(xvi) oxo, and
(xvii) —N($R^b$)—C(=O)$R^a$, (6) —$C_5$cycloalkyl or —$C_6$cycloalkyl substituted with 1-5 substituents each independently selected from:
(a) halo,
(b) —$OR^a$,
(c) —CN,
(d) —$CO_2R^a$,
(e) —$C_{1-6}$alkyl, which is unsubstituted or substituted with 1-6 halo,
(f) —C(=O)$NR^bR^c$,
(g) —S(O)$_vR^d$;
(h) —$C_{3-6}$cycloalkyl, which is unsubstituted or substituted with 1-6 halo,
(i) —$NR^bR^c$,
(j) —O—$CO_2R^d$,
(k) —C≡c—$R^a$,
(l) —N($R^b$)—$CO_2R^d$,
(m) —N($R^b$)—$SO_2R^d$,
(n) —C(=O)$R^a$,
(o) —O—C(=O)$R^a$,
(p) oxo,
(q) —N($R^b$)—C(=O)$R^a$, and
(r) phenyl or heterocycle, wherein heterocycle is selected from; pyridyl, pyrimidinyl, pyrazinyl, pyridazinyl, piperidyl, piperazinyl, pyrrolidinyl, thienyl, morpholinyl, thiazolyl, oxazolyl, isoxazolyl, furanyl, tetrahydrofuranyl, and tetrahydropyranyl, which phenyl or heterocycle is unsubstituted or substituted with 1-5 substituents each independently selected from:
(i) halo,
(ii) —OR$^a$,
(iii) —CN,
(iv) —CO$_2$R$^a$,
(v) —C$_{1-6}$alkyl, which is optionally substituted with 1-6 halo,
(vi) —C(=O)NR$^b$R$^c$,
(vii) —S(O)$_v$R$^d$;
(viii) —C$_{3-6}$cycloalkyl, which optionally substituted with 1-6 halo,
(ix) —NR$^b$R$^c$,
(x) —O—CO$_2$R$^d$,
(xi) —C≡C—R$^a$,
(xii) —N(R$^b$)—CO$_2$R$^d$,
(xiii) —N(R$^b$)—SO$_2$R$^d$,
(xiv) —C(=O)R$^a$,
(xv) —O—C(=O)R$^a$,
(xvi) oxo, and
(xvii) —N(R$^b$)—C(=O)R$^a$,
(7) —CO$_2$R$^a$,
(8) —NR$^b$R$^c$,
(9) —OR$^d$, and
(10) —C$_{4-11}$bicycloalkyl or —C$_{4-15}$tricycloalkyl, where one or two non-bridge head carbons
are optionally replaced with and oxygen(s), and one or two carbons may be optionally replaced with nitrogen(s), which bicyclo- or tricyclo-groups are unsubstituted or substituted with 1-4 substituents each independently selected from:
(a) halo,
(b) —OR$^a$,
(c) CO$_2$R$^a$,
(d) —CN,
(e) oxo, and
(f) —C$_{1-6}$alkyl, which is optionally substituted with 1-6 halo;

R$^{11}$ is independently selected from the group consisting of:
C$_{3-10}$cycloalkyl, phenyl, naphthyl, tetrahydronaphthyl, indanyl, biphenyl, phenanthryl, anthryl, azepinyl, azetidinyl, benzimidazolyl, benzisoxazolyl, benzofuranyl, benzofurazanyl, benzopyranyl, benzothiopyranyl, benzofuryl, benzothiazolyl, benzothienyl, benzoxazolyl, benzopyrazolyl, benzotriazolyl, chromanyl, cinnolinyl, dibenzofuranyl, dihydrobenzofuryl, dihydrobenzothienyl, dihydrobenzothiopyranyl, dihydrobenzothiopyranyl sulfone, furyl, furanyl, imidazolidinyl, imidazolinyl, imidazolyl, indolinyl, indolyl, isochromanyl, isoindolinyl, isoquinolinyl, isothiazolidinyl, isothiazolyl, morpholinyl, naphthyridinyl, oxadiazolyl, 2-oxoazepinyl, 4-oxonaphthyridinyl, 2-oxopiperazinyl, 2-oxopiperidinyl, 2-oxopyrrolidinyl, 2-oxopyridyl, 2-oxoquinolinyl, piperidyl, piperazinyl, pyrazinyl, pyrazolidinyl, pyrazolyl, pyridazinyl, pyridinyl, pyridyl, pyrimidinyl, pyrimidyl, pyrrolidinyl, pyrrolyl, quinazolinyl, quinolinyl, quinoxalinyl, tetrahydrofuranyl, tetrahydrofuryl, tetrahydroimidazopyridinyl, tetrahydroisoquinolinyl, tetrahydroquinolinyl, tetrazolyl, thiamorpholinyl, thiamorpholinyl sulfoxide, thiazolyl, thiazolinyl, thienofuryl, thienothienyl, thienyl, and triazolyl, where R$^{11}$ is unsubstituted or substituted with 1-5 substituents each independently selected from R$^{12}$, R$^{13}$, R$^{14}$, R$^{15a}$ and R$^{15b}$;

R$^{12}$, R$^{13}$, R$^{14}$, R$^{15a}$ and R$^{15b}$ are each independently selected from:
(1) —C$_{1-6}$alkyl, which is unsubstituted or substituted with 1-5 substituents each independently selected from:
(a) halo,
(b) —OR$^a$,
(c) —C$_{3-6}$cycloalkyl,
(d) phenyl or heterocycle, wherein heterocycle is selected from: pyridyl, pyrimidinyl, pyrazinyl, pyridazinyl, piperidinyl, piperazinyl, pyrrolidinyl, thienyl, morpholinyl, thiazolyl, or oxazolyl, which phenyl or heterocycle is unsubstituted and substituted with 1-5 substituents each independently selected from:
(i) halo,
(ii) —C$_{1-6}$alkyl, which is unsubstituted or substituted with 1-5 halo, and
(iii) —OR$^a$,
(e) —CO$_2$R$^a$,
(f) —C(=O)NR$^b$R$^c$,
(g) —S(O)$_v$R$^d$,
(h) —CN,
(i) —NR$^b$R$^c$,
(j) —N(R$^b$)C(=O)R$^a$,
(k) —N(R$^b$)SO$_2$R$^d$,
(l) —CF$_3$,
(m) —O—CO$_2$R$^d$,
(n) —O—(C=O)—NR$^b$R$^c$,
(o) —NR$^b$—(C=O)—NR$^b$R$^c$, and
(p) —C(=O)R$^a$,
(2) —C$_{1-6}$cycloalkyl, which is unsubstituted or substituted with 1-5 substituents each independently selected from:
(a) halo,
(b) —CN,
(c) —C$_{1-6}$alkyl, which is unsubstituted or substituted with 1-5 halo,
(d) —OR$^a$, and
(e) phenyl, which is unsubstituted or substituted with 1-5 substituents each independently selected from:
(i) —OR$^a$,
(ii) halo,
(iii) —CN, and
(iv) —C$_{1-6}$alkyl, which is unsubstituted or substituted with 1-5 halo,
(3) phenyl or heterocycle, wherein heterocycle is selected from: pyridyl, pyrimidinyl, pyrazinyl, pyridazinyl, piperidinyl, piperazinyl, pyrrolidinyl, thienyl, morpholinyl, thiazolyl, and oxazolyl, which phenyl or heterocycle is unsubstituted or substituted with 1-5 substituents each independently selected from:
(a) halo,
(b) —OR$^a$,
(c) —C$_{3-6}$cycloalkyl,
(d) phenyl, which is unsubstituted or substituted with 1-5 substituents each independently selected from:
(i) halo,
(ii) —C$_{1-6}$alkyl, which is unsubstituted or substituted with 1-6 halo, and
(iii) —OR$^a$,
(e) —CO$_2$R$^a$,
(f) —C(=O)NR$^b$R$^c$,
(g) —S(O)$_v$R$^d$,
(h) —CN,
(i) —NR$^b$R$^c$,
(j) —N(R$^b$)C(=O)R$^a$,
(k) —N(R$^b$)SO$_2$R$^d$,
(l) —O—CO$_2$R$^d$, (m) —O—(C=O)—NR$^b$R$^c$,
(n) —NR$^b$—(C=O)—NR$^b$R$^c$,
(o) —C(=O)R$^a$, and
(p) —C$_{1-6}$alkyl, which is unsubstituted or substituted with 1-6 halo,
(4) halo,
(5) oxo,
(6) —OR$^a$,
(7) —CN,
(8) —CO$_2$R$^a$,
(9) —C(=O)R$^a$,
(10) —NR$^b$R$^c$,
(11) —S(O)$_v$R$^d$,
(12) —C(=O)NR$^b$R$^c$,
(13) —O—CO$_2$R$^d$,
(14) —N(R$^b$)CO$_2$R$^d$,
(15) —O—(C=O)—NR$^b$R$^c$,
(16) —NR$^b$—(C=O)—NR$^b$R$^c$,
(17) —SO$_2$NR$^b$R$^c$,
(18) —N(R$^b$)SO$_2$R$^d$,
or where R$^{15a}$ and R$^{15b}$ and the atom(s) to which they are attached join to form a ring selected from cyclopropyl, cyclobutyl, cyclopentyl, cyclohexyl, cycloheptyl, aziridinyl, azetidinyl, pyrrolidinyl, piperidinyl, piperazinyl, morpholinyl, thietanyl, and tetrahydrothienyl wherein the sulfur is optionally oxidized to the sulfone or sulfoxide, which ring is unsubstituted or substituted with 1-5 substituents each independently selected from:
(a) —C$_{1-6}$alkyl, which is unsubstituted or substituted with 1-3 substituents each independently selected from:
(i) halo,
(ii) —OR$^a$,
(iii) —C$_{3-6}$cycloalkyl,
(iv) —CO$_2$R$^a$,
(v) —NR$^b$R$^c$,
(vi) —S(O)$_v$R$^d$,
(vii) —C(=O)NR$^b$R$^c$, and
(viii) phenyl,
(b) phenyl or heterocycle, wherein heterocycle is selected from: pyridyl, pyrimidinyl, pyrazinyl, pyridazinyl, piperidinyl, piperazinyl, pyrrolidinyl, thienyl, morpholinyl, thiazolyl, and oxazolyl, which phenyl or heterocycle is unsubstituted or substituted with 1-5 substituents each independently selected from:
(i) halo,
(ii) —C$_{1-6}$alkyl, which is unsubstituted or substituted with 1-5 halo, and
(iii) —OR$^a$,
(c) —OR$^a$,
(d) halo,
(e) —CO$_2$R$^a$,
(f) —C(=O)NR$^b$R$^c$,
(g) —S(O)$_v$R$^d$,
(h) —CN,
(i) —NR$^b$R$^c$,
(j) —N(R$^b$)C(=O)R$^a$,
(k) —N(R$^b$)SO$_2$R$^d$,
(l) —O—CO$_2$R$^d$,
(m) —O—(C=O)—NR$^b$R$^c$,
(n) —NR$^b$—(C=O)—NR$^b$R$^c$, and
(o) —C(=O)R$^a$;
R$^{PG}$ is independently selected from:
(1) hydrogen,
(2) —CH$_2$OR$^a$,
(3) —CH$_2$—O—CH$_2$CH$_2$Si(CH$_3$)$_3$,
(4) —C$_{1-6}$alkyl which is unsubstituted or substituted with 1-5 halo,
(5) —CH$_2$—O—P(=O)(OR$^a$)$_2$ and
(6) —(CH$_2$)$_k$-phenyl, which is unsubstituted or substituted with 1-3 substituents where the substituents are each independently selected from:
(a) halo,
(b) —OR$^a$,
(c) —CN, and
(d) —C$_{1-6}$alkyl, which is unsubstituted or substituted with 1-6 halo;
J is independently selected from:
(1) =C(R$^{16a}$)—,
(2) —CR$^{17}$R$^{18}$—,
(3) —C(=O)—, and
(4) —N(R$^b$)—;
Y is independently selected from:
(1) =C(R$^{16b}$)—,
(2) —CR$^{17}$R$^{18}$—,
(3) —C(=O)—,
(4) =N—, and
(5) —N(R$^{16b}$)—;
R$^{17}$ and R$^{18}$ are each independently selected from:
(1) hydrogen,
(2) halo,
(3) —OR$^a$,
(4) —C$_{1-6}$alkyl, which is unsubstituted or substituted with 1-4 substituents each independently selected from:
(a) halo,
(b) —OR$^a$,
(c) —CN,
(d) phenyl or heterocycle wherein heterocycle is selected from pyridyl, pyrimidinyl, thienyl, pyridazinyl, piperidinyl, azetidinyl, piperazinyl, pyrrolidinyl, morpholinyl, tetrahydropyranyl, tetrahydropyranyl, and pyrazinyl, which phenyl or heterocycle is unsubstituted or substituted with 1-5 substituents each independently selected from:
(i) —OR$^a$,
(ii) halo,
(iii) —CN,
(iv) —C$_{1-6}$alkyl which is unsubstituted or substituted with 1-6 halo,
(5) phenyl or heterocycle wherein heterocycle is selected from pyridyl, pyrimidinyl, thienyl, pyridazinyl, piperidinyl, azetidinyl, piperazinyl, pyrrolidinyl, morpholinyl, tetrahydrofuranyl, tetrahydropyranyl, and pyrazinyl, which phenyl or heterocycle is unsubstituted or substituted with 1-5 substituents each independently selected from:
(a) halo,
(b) —CN,
(c) —OR$^a$,
(d) nitro,
(e) —C$_{1-6}$alkyl which is unsubstituted or substituted with 1-6 halo;
or where R$^{17}$ and R$^{18}$ and the atom to which they are attached join to form a 4-, 5-, or 6-membered ring, said ring optionally containing a heteroatom selected from N, O, and S, wherein said sulfur is optionally oxidized to a sulfone or sulfoxide, which ring is unsubstituted or substituted with 1-4 substituents each independently selected from:
(a) halo,
(b) —OR$^a$,
(c) —C$_{1-6}$alkyl, which is unsubstituted or substituted with 1-6 halo, and
(d) phenyl;

$R^{16a}$ and $R^{16b}$ are each independently selected from:
(1) hydrogen,
(2) —$C_{1-4}$alkyl, which is unsubstituted or substituted with 1-5 substituents each independently selected from:
  (a) halo,
  (b) —$OR^a$,
  (c) —$C_{3-6}$cycloalkyl,
  (d) phenyl or heterocycle, wherein heterocycle is selected from: imidazolyl, oxazolyl, pyridyl, pyrimidinyl, pyrazinyl, pyridazinyl, piperidinyl, piperazinyl, pyrrolidinyl, thiazolyl, thienyl, triazolyl, isoxazolyl, and morpholinyl, which phenyl or heterocycle is unsubstituted or substituted with 1-3 substituents each independently selected from:
    (i) halo,
    (ii) —$OR^a$,
    (iii) —CN, and
    (iv) $C_{1-6}$alkyl, which is unsubstituted or substituted with 1-6 halo,
(3) phenyl or heterocycle, wherein heterocycle is selected from: imidazolyl, oxazolyl, pyridyl, pyrimidinyl, pyrazinyl, pyridazinyl, tetrahydrofuryl, piperidinyl, piperazinyl, pyrrolidinyl, azetidinyl, thiazolyl, thienyl, triazolyl, isoxazolyl, and morpholinyl, which phenyl or heterocycle is unsubstituted or substituted with 1-3 substituents each independently selected from:
  (a) halo,
  (b) —$OR^a$,
  (c) —$C_{3-6}$cycloalkyl,
  (d) —$C_{1-4}$alkyl which is unsubstituted or substituted with 1-6 halo, and
  (e) phenyl, which is unsubstituted or substituted with 1-5 substituents each independently selected from:
    (i) halo,
    (ii) —$C_{1-6}$alkyl, which is unsubstituted or substituted with 1-6 halo, and
    (iii) —$OR^a$,
(4) halo,
(5) —$OR^a$,
(6) —CN,
(7) —$CO_2R^a$,
(8) —$NR^bR^c$, and
(9) —C(=O)$NR^bR^c$;
or where $R^{16a}$ and $R^{16b}$ and the atom(s) to which they are attached join to form a ring selected from cyclopentenyl, cyclohexenyl, phenyl, pyridyl, pyrimidinyl, pyrazinyl, pyridazinyl, furanyl, dihydrofuranyl, dihydropyranyl, thiazolyl, isothiazolyl, oxazolyl, isoxazolyl, imidazolyl, triazolyl, thienyl, dihydrothienyl, and dihydrothiopyranyl, which ring is unsubstituted or substituted with 1-5 substituents each independently selected from:
  (a) —$C_{1-6}$alkyl, which is unsubstituted or substituted with 1-3 substituents each independently selected from:
    (i) halo,
    (ii) —$OR^a$,
    (iii) —$C_{3-6}$cycloalkyl,
    (iv) phenyl or heterocycle, wherein heterocycle is selected from pyridyl, pyrimidinyl, pyrazinyl, pyridazinyl, piperidinyl, piperazinyl, pyrrolidinyl, thienyl, and morpholinyl, which phenyl or heterocycle is unsubstituted or substituted with 1-5 substituents each independently selected from:
      (I) —$OR^a$,
      (II) halo,
      (III) —CN, and
      (IV) —$C_{1-6}$alkyl which is unsubstituted or substituted with 1-6 halo,
    (v) —$CO_2R^a$,
    (vi) —$NR^bR^c$,
    (vii) —$S(O)_vR^d$,
    (viii) —C(=O)$NR^bR^c$,
    (ix) —$N(R^b)CO_2R^a$, and
    (x) —$N(R^b)SO_2R^d$,
  (b) phenyl or heterocycle, wherein heterocycle is selected from pyridyl, pyrimidinyl, pyrazinyl, pyridazinyl, piperidinyl, azetidinyl, piperazinyl, pyrrolidinyl, thienyl, and morpholinyl, which phenyl and heterocycle is unsubstituted or substituted with 1-5 substituents each independently selected from:
    (i) halo,
    (ii) —$OR^a$,
    (iii) —CN, and
    (iv) —$C_{1-6}$alkyl which is unsubstituted or substituted with 1-6 halo,
  (c) halo,
  (d) —$S(O)_vR^d$,
  (e) —$OR^a$,
  (f) —CN,
  (g) —C(=O)$R^a$,
  (h) —$NR^bR^c$,
  (i) —C(=O)$NR^bR^c$,
  (j) —$CO_2R^a$,
  (k) —($NR^b$)$CO_2R^a$,
  (l) —O—(C=O)—$NR^bR^c$,
  (m) —($NR^b$)—(C=O)—$NR^bR^c$,
  (n) oxo, and
  (o) —($NR^b$)$SO_2R^d$;
$R^{21}$ is independently selected from:
(1) —C≡C—$R^a$,
(2) —$C_{1-7}$alkyl, which is unsubstituted or substituted with 1-5 substituents each independently selected from:
  (a) halo,
  (b) —$OR^a$,
  (c) —CN,
  (d) —$CO_2R^a$,
  (e) —$C_{1-6}$alkyl, which is unsubstituted or substituted with 1-6 halo,
  (f) —C(=O)$NR^bR^c$,
  (g) —$S(O)_vR^d$;
  (h) —$NR^bR^c$,
  (i) —O—$CO_2R^d$,
  (j) —C≡C—$R^a$,
  (k) —$N(R^b)$—$CO_2R^d$,
  (l) —$N(R^b)$—$SO_2R^d$,
  (m) —C(=O)$R^a$,
  (n) —O—C(=O)$R^a$,
  (o) oxo, and
  (p) —$N(R^b)$—C(=O)$R^a$,
(3) a group independently selected from: isoxazolyl, tetrahydrothienyl, thiamorpholinyl sulfone, thiadiazolyl, quinuclidinyl, norbornyl, adamantyl, tetrahydropyranyl, and azepanyl, which is unsubstituted or substituted with 1-5 substituents each independently selected from $R^{12}$, $R^{13}$, $R^{14}$, $R^{15a}$, and $R^{15b}$;
$R^{29}$ is independently selected from:
(1) —$C_{1-6}$alkyl, which is unsubstituted or substituted with 1-5 substituents each independently selected from:
  (a) halo,
  (b) —$OR^a$,
  (c) —CN,
  (d) —$CO_2R^a$, (e) —$C_{1-6}$alkyl, which is unsubstituted or substituted with 1-6 halo,
(f) —C(=O)N$R^b R^c$,
(g) —S(O)$_v R^d$;
(h) —$C_{3-6}$cycloalkyl, which is unsubstituted or substituted with 1-6 halo,
(i) —N$R^b R^c$,
(j) —O—$CO_2 R^d$,
(k) —C≡C—$R^a$,
(l) —N($R^b$)—$CO_2 R^d$,
(m) —N($R^b$)—$SO_2 R^d$,
(n) —C(=O)$R^a$,
(o) —O—C(=O)$R^a$,
(p) oxo,
(q) —N($R^b$)—C(=O)$R^a$, and
(r) phenyl or heterocycle, wherein heterocycle is selected from; pyridyl, pyrimidinyl, pyrazinyl, pyridazinyl, piperidyl, piperazinyl, pyrrolidinyl, thienyl, morpholinyl, thiazolyl, oxazolyl, isoxazolyl, furanyl, tetrahydrofuranyl, or tetrahydropyranyl, which phenyl or heterocycle is unsubstituted or substituted with 1-5 substituents each independently selected from:
   (i) halo,
   (ii) —O$R^a$,
   (iii) —CN,
   (iv) —$CO_2 R^a$,
   (v) —$C_{1-6}$alkyl, which is optionally substituted with 1-6 halo,
   (vi) —C(=O)N$R^b R^c$,
   (vii) —S(O)$_v R^d$;
   (viii) —$C_{3-6}$cycloalkyl, which optionally substituted with 1-6 halo,
   (ix) —N$R^b R^c$,
   (x) —O—$CO_2 R^d$,
   (xi) —C≡C—$R^a$,
   (xii) —N($R^b$)—$CO_2 R^d$,
   (xiii) —N($R^b$)—$SO_2 R^d$,
   (xiv) —C(=O)$R^a$,
   (xv) —O—C(=O)$R^a$,
   (xvi) oxo, and
   (xvii) —N($R^b$)—C(=O)$R^a$,
(2) a group independently selected from: $C_{3-10}$cycloalkyl, phenyl, naphthyl, tetrahydronaphthyl, indanyl, biphenyl, phenanthryl, anthryl, azepinyl, azepanyl, azetidinyl, benzimidazolyl, benzisoxazolyl, benzofuranyl, benzofurazanyl, benzopyranyl, benzothiopyranyl, benzofuryl, benzothiazolyl, benzothienyl, benzoxazolyl, benzopyrazolyl, benzotriazolyl, chromanyl, cinnolinyl, dibenzofuranyl, dihydrobenzofuryl, dihydrobenzothienyl, dihydrobenzothiopyranyl, dihydrobenzothiopyranyl sulfone, furyl, furanyl, imidazolidinyl, imidazolinyl, imidazolyl, indolinyl, indolyl, isochromanyl, isoindolinyl, isoquinolinyl, isothiazolidinyl, isothiazolyl, morpholinyl, naphthyridinyl, oxadiazolyl, 2-oxoazepinyl, 4-oxonaphthyridinyl, 2-oxopiperazinyl, 2-oxopiperidinyl, 2-oxopyrrolidinyl, 2-oxopyridyl, 2-oxoquinolinyl, piperidyl, piperazinyl, pyrazinyl, pyrazolidinyl, pyrazolyl, pyridazinyl, pyridinyl, pyridyl, pyrimidinyl, pyrimidyl, pyrrolidinyl, pyrrolyl, quinazolinyl, quinolinyl, quinoxalinyl, tetrahydrofuranyl, tetrahydrofuryl, tetrahydroimidazopyridinyl, tetrahydroisoquinolinyl, tetrahydroquinolinyl, tetrazolyl, thiamorpholinyl, thiamorpholinyl sulfoxide, thiamorpholinyl sulfone, thiazolyl, thiazolinyl, thienofuryl, thienothienyl, thienyl, triazolyl, isoxazolyl, tetrahydrothienyl, tetrahydropyranyl, oxetanyl, tetrahydrothiapyranyl, and thietanyl, which group is unsubstituted or substituted with 1-5 substituents each independently selected from:
(a) halo,
(b) —O$R^a$,
(c) —CN,
(d) —$CO_2 R^a$,
(e) —$C_{1-6}$alkyl, which is unsubstituted or substituted with 1-6 halo,
(f) —C(=O)N$R^b R^c$,
(g) —S(O)$_v R^d$;
(h) —$C_{3-6}$cycloalkyl, which is unsubstituted or substituted with 1-6 halo,
(i) —N$R^b R^c$,
(j) —O—$CO_2 R^d$,
(k) —C≡C—$R^a$,
(l) —N($R^b$)—$CO_2 R^d$,
(m) —N($R^b$)—$SO_2 R^d$,
(n) —C(=O)$R^a$,
(o) —O—C(=O)$R^a$,
(p) oxo,
(q) —N($R^b$)—C(=O)$R^a$, and
(r) phenyl or heterocycle, wherein heterocycle is selected from; pyridyl, pyrimidinyl, pyrazinyl, pyridazinyl, piperidyl, piperazinyl, pyrrolidinyl, thienyl, morpholinyl, thiazolyl, oxazolyl, isoxazolyl, furanyl, tetrahydrofuranyl, or tetrahydropyranyl, which phenyl or heterocycle is unsubstituted or substituted with 1-5 substituents each independently selected from:
   (i) halo,
   (ii) —O$R^a$,
   (iii) —CN,
   (iv) —$CO_2 R^a$,
   (v) —$C_{1-6}$alkyl, which is optionally substituted with 1-6 halo,
   (vi) —C(=O)N$R^b R^c$,
   (vii) —S(O)$_v R^d$;
   (viii) —$C_{3-6}$cycloalkyl, which optionally substituted with 1-6 halo,
   (ix) —N$R^b R^c$,
   (x) —O—$CO_2 R^d$,
   (xi) —C≡C—$R^a$,
   (xii) —N($R^b$)—$CO_2 R^d$,
   (xiii) —N($R^b$)—$SO_2 R^d$,
   (xiv) —C(=O)$R^a$,
   (xv) —O—C(=O)$R^a$,
   (xvi) oxo, and
   (xvii) —N($R^b$)—C(=O)$R^a$,
(3) —$CO_2 R^a$,
(4) —N$R^b R^c$,
(5) hydrogen,
(6) —O$R^d$, and
(7) —$C_{4-11}$ bicycloalkyl or —$C_{4-15}$tricycloalkyl, where one or two non-bridge head carbons are optionally replaced with and oxygen(s), and one or two carbons may be optionally replaced with nitrogen(s), which bicyclo- or tricyclo-groups are unsubstituted or substituted with 1-4 substituents each independently selected from:
(a) halo,
(b) —O$R^a$,
(c) $CO_2 R^a$,
(d) oxo,
(e) —CN, and
(f) —$C_{1-6}$alkyl, which is optionally substituted with 1-6 halo;

$R^a$ is independently selected from:
(1) hydrogen,
(2) $C_{1-6}$alkyl, which is unsubstituted or substituted with 1-7 substituents each independently selected from:
  (a) halo,
  (b) —O—$C_{1-6}$alkyl, which is unsubstituted or substituted with 1-6 halo,
  (c) hydroxyl,
  (d) —CN, and
  (e) phenyl or heterocycle wherein heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl, and pyrazinyl, which phenyl or heterocycle is unsubstituted or substituted with 1-3 substituents each independently selected from:
    (i) halo,
    (ii) —O—$C_{1-6}$alkyl, which is unsubstituted or substituted with 1-6 halo,
    (iii) —CN,
    (iv) nitro,
    (v) hydroxyl, and
    (vi) —$C_{1-6}$alkyl, which is unsubstituted or substituted with 1-6 halo,
(3) phenyl or heterocycle wherein heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl, and pyrazinyl, which phenyl or heterocycle is unsubstituted or substituted with 1-3 substituents each independently selected from:
  (a) halo,
  (b) —CN,
  (c) —O—$C_{1-6}$alkyl, which is unsubstituted or substituted with 1-6 halo,
  (d) nitro,
  (e) hydroxyl, and
  (f) —$C_{1-6}$alkyl, which is unsubstituted or substituted with 1-6 halo,
(4) —$C_{3-6}$cycloalkyl, which is unsubstituted or substituted with 1-6 halo;
$R^b$ and $R^c$ are each independently selected from:
(1) hydrogen,
(2) $C_{1-6}$alkyl, which is unsubstituted or substituted with 1-7 substituents each independently selected from:
  (a) halo,
  (b) —OR$^a$,
  (c) —CN,
  (d) —CO$_2$R$^a$, and
  (e) phenyl or heterocycle wherein heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl, and pyrazinyl, which phenyl or heterocycle is unsubstituted or substituted with 1-3 substituents each independently selected from:
    (i) halo,
    (ii) —OR$^a$,
    (iii) —$C_{1-6}$alkyl, which is unsubstituted or substituted with 1-6 halo, and
    (iv) nitro,
(3) phenyl or heterocycle wherein heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl, and pyrazinyl, which phenyl or heterocycle is unsubstituted or substituted with 1-3 substituents each independently selected from:
  (a) halo,
  (b) —OR$^a$,
  (c) —$C_{1-6}$alkyl, which is unsubstituted or substituted with 1-6 halo,
  (d) —$C_{3-6}$cycloalkyl, which is unsubstituted or substituted with 1-6 halo,
  (e) —CN, and
  (f) —CO$_2$R$^a$,
(4) —$C_{3-6}$cycloalkyl, which is unsubstituted or substituted with 1-6 halo;
or where $R^b$ and $R^c$ and the nitrogen to which they are attached join to form a 4-, 5-, or 6-membered ring, optionally containing an additional heteroatom selected from N, O, and S wherein the sulfur is optionally oxidized to the sulfone or sulfoxide, which ring is unsubstituted or substituted with 1-4 substituents each independently selected from:
  (a) halo,
  (b) —OR$^a$, and
  (c) —$C_{1-6}$alkyl, which is unsubstituted or substituted with 1-6 halo, and
  (d) phenyl;
$R^d$ is independently selected from:
(1) $C_{1-6}$alkyl, which is unsubstituted or substituted with 1-4 substituents each independently selected from:
  (a) halo,
  (b) —OR$^a$,
  (c) —CO$_2$R$^a$,
  (d) —CN, and
  (e) phenyl or heterocycle, wherein heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl, and pyrazinyl, which phenyl or heterocycle is unsubstituted or substituted with 1-3 substituents each independently selected from:
    (i) halo,
    (ii) —OR$^a$,
    (iii) —$C_{1-6}$alkyl, which is unsubstituted or substituted with 1-6 halo, and
    (iv) nitro,
(2) phenyl or heterocycle, wherein heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl, and pyrazinyl, which phenyl or heterocycle is unsubstituted or substituted with 1-3 substituents each independently selected from:
  (a) halo,
  (b) —OR$^a$,
  (c) —$C_{1-6}$alkyl, which is unsubstituted or substituted with 1-6 halo,
  (d) —$C_{3-6}$cycloalkyl, which is unsubstituted or substituted with 1-6 halo
  (e) —CN, and
  (f) —CO$_2$R$^a$,
(3) —$C_{3-6}$cycloalkyl, which is unsubstituted or substituted with 1-6 halo;
$R^e$ and $R^f$ are independently selected from:
(1) hydrogen,
(2) $C_{1-6}$alkyl, which is unsubstituted or substituted with 1-4 substituents each independently selected from:
  (a) halo,
  (b) —OR$^a$,
  (c) —CO$_2$R$^a$,
  (d) —CN, (e) —S(O)$_v$R$^a$, and
(f) phenyl or heterocycle, wherein heterocycle is selected from pyridyl, pyrimidinyl; thienyl, pyridazinyl, piperidinyl, azetidinyl, furanyl, piperazinyl, pyrrolidinyl, morpholinyl, tetrahydrofuranyl, tetrahydropyranyl, and pyrazinyl, which phenyl or heterocycle is unsubstituted or substituted with 1-3 substituents each independently selected from:
  (i) halo,
  (ii) —OR$^a$,
  (iii) —C$_{1-6}$alkyl, which is unsubstituted or substituted with 1-6 halo, and
  (iv) nitro,
(3) phenyl or heterocycle, wherein heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl, and pyrazinyl, which phenyl or heterocycle is unsubstituted or substituted with 1-3 substituents each independently selected from:
  (b) halo,
  (c) —OR$^a$,
  (d) —C$_{1-6}$alkyl, which is unsubstituted or substituted with 1-6 halo,
  (e) —C$_{3-6}$cycloalkyl, which is unsubstituted or substituted with 1-6 halo
  (f) —CN, and
  (g) —CO$_2$R$^a$,
(4) —C$_{3-6}$cycloalkyl, which is unsubstituted or substituted with 1-6 halo;
or where R$^e$ and R$^f$ and the atom to which they are attached join to form a 4-, 5-, or 6-membered ring, optionally containing a heteroatom selected from N, O, and S wherein the sulfur is optionally oxidized to the sulfone or sulfoxide, which ring is unsubstituted or substituted with 1-4 substituents each independently selected from:
  (a) halo,
  (b) —OR$^a$,
  (c) —C$_{1-6}$alkyl, which is unsubstituted or substituted with 1-6 halo, and
  (d) phenyl;
m is 1, 2, or 3;
n is 1, 2, or 3;
v is 0, 1, or 2;
and pharmaceutically acceptable salts thereof and individual enantiomers and diastereomers thereof.

An embodiment of the invention includes compounds of formula Ia:

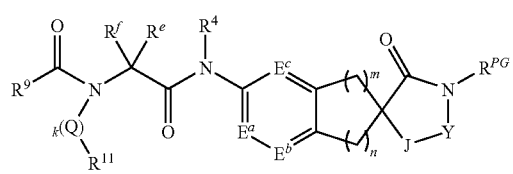

wherein k, m, n, J, Q, R$^4$, R$^e$, R$^f$, E$^a$, E$^b$, E$^c$, R$^9$, R$^{11}$, R$^{PG}$ and Y are defined herein;
and pharmaceutically acceptable salts thereof and individual enantiomers and diastereomers thereof.

Another embodiment of the invention includes compounds of formula Ib:

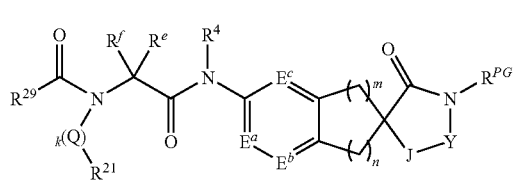

wherein k, m, n, J, Q, R$^4$, R$^e$, R$^f$, E$^a$, E$^b$, E$^c$, R$^{29}$, R$^{21}$, R$^{PG}$ and Y are defined herein;
and pharmaceutically acceptable salts thereof and individual enantiomers and diastereomers thereof.

Another embodiment of the invention includes compounds of formula Ic:

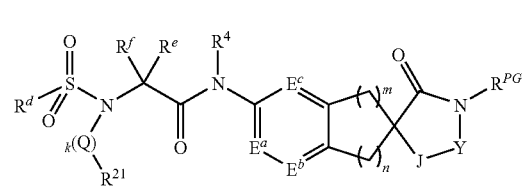

wherein k, m, n, J, Q, R$^4$, R$^d$, R$^e$, R$^f$, E$^a$, E$^b$, E$^c$, R$^{21}$, R$^{PG}$ and Y are defined herein;
and pharmaceutically acceptable salts thereof and individual enantiomers and diastereomers thereof.

An embodiment of the invention includes compounds of formula Id:

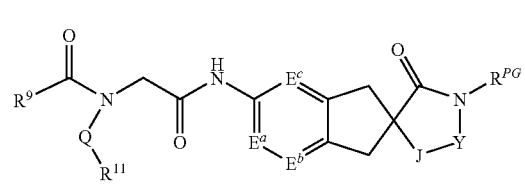

wherein J, Q, E$^a$, E$^b$, E$^c$, R$^9$, R$^{11}$, R$^{PG}$ and Y are defined herein;
and pharmaceutically acceptable salts thereof and individual enantiomers and diastereomers thereof.

Another embodiment of the invention includes compounds of formula Ie:

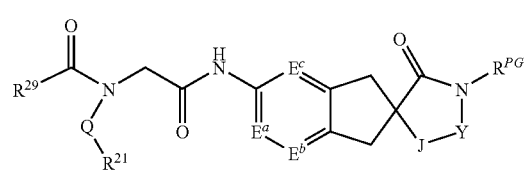

wherein J, Q, E$^a$, E$^b$, E$^c$, R$^{29}$, R$^{21}$, R$^{PG}$ and Y are defined herein;
and pharmaceutically acceptable salts thereof and individual enantiomers and diastereomers thereof.

Another embodiment of the invention includes compounds of formula If:

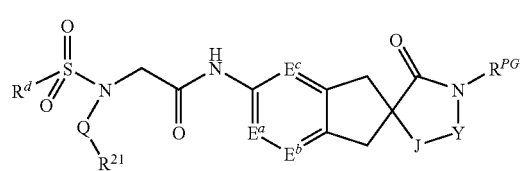

If wherein J, Q, $R^d$, $E^a$, $E^b$, $E^c$, $R^{21}$, $R^{PG}$ and Y are defined herein;
and pharmaceutically acceptable salts thereof and individual enantiomers and diastereomers thereof.

An embodiment of the invention includes compounds of formula Ig:

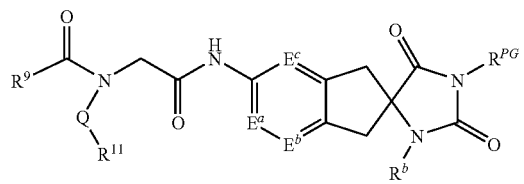

Ig wherein Q, $E^a$, $E^b$, $E^c$, $R^9$, $R^{11}$, $R^{PG}$ and $R^b$ are defined herein;
and pharmaceutically acceptable salts thereof and individual enantiomers and diastereomers thereof.

Another embodiment of the invention includes compounds of formula Ih:

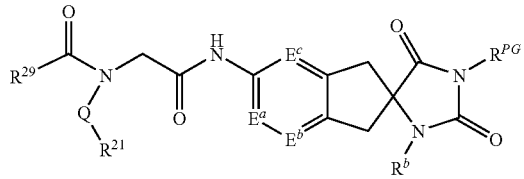

Ih wherein Q, $E^a$, $E^b$, $E^c$, $R^{29}$, $R^{21}$, $R^{PG}$ and $R^b$ are defined herein;
and pharmaceutically acceptable salts thereof and individual enantiomers and diastereomers thereof.

An embodiment of the invention includes compounds of formula Ii:

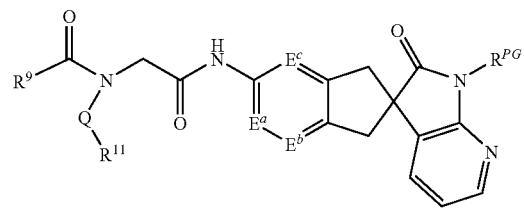

Ii wherein Q, $E^a$, $E^b$, $E^c$, $R^9$, $R^{11}$ and $R^{PG}$ are defined herein;
and pharmaceutically acceptable salts thereof and individual enantiomers and diastereomers thereof.

Another embodiment of the invention includes compounds of formula Ij:

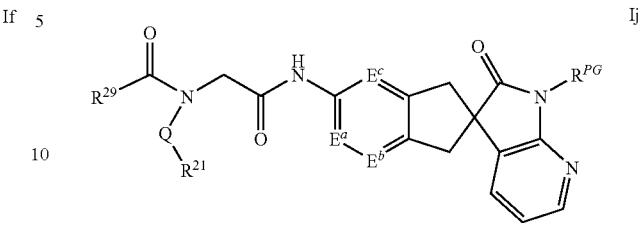

Ij wherein Q, $E^a$, $E^b$, $E^c$, $R^{29}$, $R^{21}$, and $R^{PG}$ are defined herein;
and pharmaceutically acceptable salts thereof and individual enantiomers and diastereomers thereof.

An embodiment of the invention includes compounds of formula Ik:

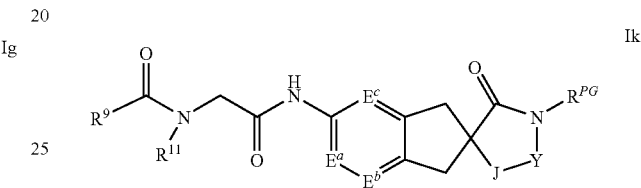

Ik wherein J, $E^a$, $E^b$, $E^c$, $R^9$, $R^{11}$, $R^{PG}$ and Y are defined herein;
and pharmaceutically acceptable salts thereof and individual enantiomers and diastereomers thereof.

Another embodiment of the invention includes compounds of formula Il:

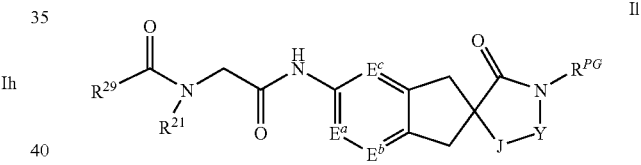

Il wherein J, $E^a$, $E^b$, $E^c$, $R^{29}$, $R^{21}$, $R^{PG}$ and Y are defined herein;
and pharmaceutically acceptable salts thereof and individual enantiomers and diastereomers thereof.

In an embodiment of the present invention Q is independently selected from:
(1) —$CH_2$—,
(2) —$CHR^d$—, and
(3) —$C(R^d)_2$—, wherein $R^d$ is defined herein.

In an embodiment of the present invention Q is —$CH_2$—.
In an embodiment of the present invention Q is —CH($CH_3$)—.
In an embodiment of the present invention $R^4$ is selected from: hydrogen and —$C_{1-6}$alkyl, which is unsubstituted or substituted with 1-5 fluoro.
In an embodiment of the present invention $R^4$ is hydrogen.
In an embodiment of the present invention $E^a$ is selected from:
(1) —$C(R^{5a})$=,
(2) —N=, and
(3) —$(N^+$—$O^-)$=; wherein $R^{5a}$ is defined herein.

In an embodiment of the present invention $E^a$ is —C(H)=.
In an embodiment of the present invention $E^a$ is —N=.
In an embodiment of the present invention $E^b$ is selected from:
(1) —$C(R^{5b})$=,
(2) —N=, and
(3) —$(N^+$—$O^-)$=; wherein $R^{5b}$ is defined herein.

In an embodiment of the present invention $E^b$ is —C(H)=.
In an embodiment of the present invention $E^b$ is —N=.
In an embodiment of the present invention $E^c$ is selected from:
(1) —C($R^{5c}$)=,
(2) —N=, and
(3) —($N^+$—$O^-$)=; wherein $R^{5c}$ is defined herein.
In an embodiment of the present invention $E^c$ is —C(H)=.
In an embodiment of the present invention $E^c$ is —N=.
In an embodiment of the present invention $R^{5a}$ is selected from:
(1) hydrogen,
(2) —$C_{1-6}$alkyl, which is unsubstituted or substituted with 1-6 halo,
(3) halo, and
(4) —O—$C_{1-6}$alkyl, which is unsubstituted or substituted with 1-6 halo.
In an embodiment of the present invention $R^{5a}$ is independently selected from: hydrogen, halo and —$C_{1-3}$alkyl, which is unsubstituted or substituted with 1-5 fluoro.
In an embodiment of the present invention $R^{5a}$ is methyl.
In an embodiment of the present invention $R^{5a}$ is hydrogen.
In an embodiment of the present invention $R^{5b}$ is selected from:
(1) hydrogen,
(2) —$C_{1-6}$alkyl, which is unsubstituted or substituted with 1-6 halo,
(3) halo, and
(4) —O—$C_{1-6}$alkyl, which is unsubstituted or substituted with 1-6 halo.
In an embodiment of the present invention $R^{5b}$ is independently selected from: hydrogen, halo and —$C_{1-3}$alkyl, which is unsubstituted or substituted with 1-5 fluoro.
In an embodiment of the present invention $R^{5b}$ is methyl.
In an embodiment of the present invention $R^{5b}$ is hydrogen.
In an embodiment of the present invention $R^{5c}$ is selected from:
(1) hydrogen,
(2) —$C_{1-6}$alkyl, which is unsubstituted or substituted with 1-6 halo,
(3) halo, and
(4) —O—$C_{1-6}$alkyl, which is unsubstituted or substituted with 1-6 halo.
In an embodiment of the present invention $R^5$ is independently selected from: hydrogen, halo and —$C_{1-3}$alkyl, which is unsubstituted or substituted with 1-5 fluoro.
In an embodiment of the present invention $R^{5c}$ is methyl.
In an embodiment of the present invention $R^{5C}$ is hydrogen.
In an embodiment of the present invention $R^9$ is independently selected from:
(1) —$C_1$alkyl, optionally substituted with 1-2 fluoro, and further substituted with 1-2 substituents which are each independently selected from:
(a) chloro,
(b) bromo,
(c) —$OR^a$,
(d) —CN,
(e) —$CO_2R^a$,
(f) —C(=O)$NR^bR^c$,
(g) —S(O)$_xR^d$;
(h) —$C_{3-6}$cycloalkyl, which is unsubstituted or substituted with 1-6 halo,
(i) —O—$CO_2R^d$,
(j) —C≡C—$R^a$,
(k) —N($R^b$)—$CO_2R^d$,
(l) —O—C(=O)$R^a$,
(m) —N($R^b$)—C(=O)$R^a$, and
(n) heterocycle, wherein heterocycle is selected from; pyridyl, pyrimidinyl, pyrazinyl, pyridazinyl, piperidyl, piperazinyl, pyrrolidinyl, thienyl, morpholinyl, thiazolyl, oxazolyl, isoxazolyl, furanyl, tetrahydrofuranyl, and tetrahydropyranyl, which heterocycle is unsubstituted or substituted with 1-3 substituents each independently selected from:
(i) halo,
(ii) —$OR^a$,
(iii) —CN,
(iv) —$CO_2R^a$,
(v) —$C_{1-6}$alkyl, which is optionally substituted with 1-6 halo,
(vi) —C(=O)$NR^bR^c$,
(vii) —S(O)$_xR^d$;
(vii) —$NR^bR^c$,
(ix) —O—$CO_2R^d$,
(x) —C≡C—$R^a$,
(xii) —N($R^b$)—$CO_2R^d$,
(xiii) —O—C(=O)$R^a$,
(xiv) oxo, and
(xv) —N($R^b$)—C(=O)$R^a$,
(2) —$C_{2-8}$alkyl, optionally substituted with 1-6 fluoro, and further substituted with 1-3 substituents each independently selected from:
(a) chloro,
(b) bromo,
(c) iodo,
(d) —$OR^a$,
(e) —CN,
(f) —$CO_2R^a$,
(g) —C(=O)$NR^bR^c$,
(h) —$NR^bR^c$,
(i) —O—$CO_2R^d$,
(j) —C≡C—$R^a$,
(k) —N($R^b$)—$CO_2R^d$,
(l) —O—C(=O)$R^a$,
(r) —N($R^b$)—C(=O)$R^a$, and
(s) phenyl or heterocycle, wherein heterocycle is selected from: pyridyl, pyrimidinyl, pyrazinyl, pyridazinyl, piperidyl, piperazinyl, pyrrolidinyl, thienyl, morpholinyl, thiazolyl, oxazolyl, isoxazolyl, furanyl, tetrahydrofuranyl, and tetrahydropyranyl, which phenyl or heterocycle is unsubstituted or substituted with 1-3 substituents each independently selected from:
(i) halo,
(ii) —$OR^a$,
(iii) —CN,
(iv) —$CO_2R^a$,
(v) —$C_{1-6}$alkyl, which is optionally substituted with 1-6 halo,
(vi) —C(=O)$NR^bR^c$,
(vii) —S(O)$_xR^d$;
(viii) —$C_{3-6}$cycloalkyl, which optionally substituted with 1-6 halo,
(ix) —$NR^bR^c$,
(x) —O—$CO_2R^d$,
(xi) —C≡C—$R^a$,
(xii) —N($R^b$)—$CO_2R^d$,
(xiii) —O—C(=O)$R^a$,
(xiv) oxo, and
(xv) —N($R^b$)—C(=O)$R^a$, (3) benzyl or phenyl, substituted with 1-3 substituents each independently selected from:
(a) halo,
(b) —OR$^a$,
(c) —CN,
(d) —CO$_2$R$^a$,
(e) —C$_{1-6}$alkyl, which is unsubstituted or substituted with 1-6 halo,
(f) —C(=O)NR$^b$R$^c$,
(g) —S(O)$_v$R$^d$;
(h) —NR$^b$R$^c$,
(i) —O—CO$_2$R$^d$,
(j) —C≡C—R$^a$,
(k) —N(R$^b$)—CO$_2$R$^d$,
(l) —O—C(=O)R$^a$,
(m) —N(R$^b$)—C(=O)R$^a$, and
(n) phenyl or heterocycle, wherein heterocycle is selected from; pyridyl, pyrimidinyl, pyrazinyl, pyridazinyl, piperidyl, piperazinyl, pyrrolidinyl, thienyl, morpholinyl, thiazolyl, oxazolyl, isoxazolyl, furanyl, tetrahydrofuranyl, and tetrahydropyranyl, which phenyl or heterocycle is unsubstituted or substituted with 1-3 substituents each independently selected from:
(i) halo,
(ii) —OR$^a$,
(iii) —CN,
(iv) —CO$_2$R$^a$,
(v) —C$_{1-6}$alkyl, which is optionally substituted with 1-6 halo,
(vi) —C(=O)NR$^b$R$^c$,
(vii) —S(O)$_v$R$^d$;
(viii) —C$_{3-6}$cycloalkyl, which optionally substituted with 1-6 halo,
(ix) —NR$^b$R$^c$,
(x) —O—CO$_2$R$^d$,
(xi) —C≡C—R$^a$,
(xii) —N(R$^b$)—CO$_2$R$^d$,
(xii) —O—C(=O)R$^a$,
(xiv) oxo, and
(xv) —N(R$^b$)—C(=O)R$^a$,
(4) a group independently selected from: naphthyl, tetrahydronaphthyl, indanyl, biphenyl, phenanthryl, anthryl, azepinyl, azepanyl, azetidinyl, benzimidazolyl, benzisoxazolyl, benzofuranyl, benzofurazanyl, benzopyranyl, benzothiopyranyl, benzofuryl, benzothiazolyl, benzothienyl, benzoxazolyl, benzopyrazolyl, benzotriazolyl, chromanyl, cinnolinyl, dibenzofuranyl, dihydrobenzofuryl, dihydrobenzothienyl, dihydrobenzothiopyranyl, dihydrobenzothiopyranyl sulfone, furyl, furanyl, imidazolidinyl, imidazolinyl, imidazolyl, indolinyl, indolyl, isochromanyl, isoindolinyl, isoquinolinyl, isothiazolidinyl, isothiazolyl, morpholinyl, naphthyridinyl, oxadiazolyl, 2-oxoazepinyl, 4-oxonaphthyridinyl, 2-oxopiperazinyl, 2-oxopiperidinyl, 2-oxopyrrolidinyl, 2-oxopyridyl, 2-oxoquinolinyl, piperidyl, piperazinyl, pyrazinyl, pyrazolidinyl, pyrazolyl, pyridazinyl, pyridinyl, pyridyl, pyrimidinyl, pyrimidyl, pyrrolidinyl, pyrrolyl, quinazolinyl, quinolinyl, quinoxalinyl, tetrahydrofuranyl, tetrahydrofuryl, tetrahydroimidazopyridinyl, tetrahydroisoquinolinyl, tetrahydroquinolinyl, tetrazolyl, thiamorpholinyl, thiamorpholinyl sulfoxide, thiamorpholinyl sulfone, thiazolyl, thiazolinyl, thienofuryl, thienothienyl, thienyl, triazolyl, isoxazolyl, tetrahydrothienyl, tetrahydropyranyl, oxetanyl, tetrahydrothiapyranyl, and thietanyl, which group is unsubstituted or substituted with 1-5 substituents each independently selected from:
(a) halo,
(b) —OR$^a$,
(c) —CN,
(d) —CO$_2$R$^a$,
(e) —C$_{1-6}$alkyl, which is unsubstituted or substituted with 1-6 halo,
(f) —C(=O)NR$^b$R$^c$,
(g) —S(O)$_v$R$^d$;
(h) —C$_{3-6}$cycloalkyl, which is unsubstituted or substituted with 1-6 halo,
(i) —NR$^b$R$^c$,
(j) —O—CO$_2$R$^d$,
(k) —C≡C—R$^a$,
(l) —N(R$^b$)—CO$_2$R$^d$,
(m) —O—C(=O)R$^a$,
(n) oxo,
(o) —N(R$^b$)—C(=O)R$^a$, and
(p) phenyl or heterocycle, wherein heterocycle is selected from; pyridyl, pyrimidinyl, pyrazinyl, pyridazinyl, piperidyl, piperazinyl, pyrrolidinyl, thienyl, morpholinyl, thiazolyl, oxazolyl, isoxazolyl, furanyl, tetrahydrofuranyl, and tetrahydropyranyl, which phenyl or heterocycle is unsubstituted or substituted with 1-5 substituents each independently selected from:
(i) halo,
(ii) —OR$^a$,
(iii) —CN,
(iv) —CO$_2$R$^a$,
(v) —C$_{1-6}$alkyl, which is optionally substituted with 1-6 halo,
(vi) —C(=O)NR$^b$R$^c$,
(vii) —S(O)$_v$R$^d$;
(viii) —C$_{3-6}$cycloalkyl, which optionally substituted with 1-6 halo,
(ix) —NR$^b$R$^c$,
(x) —O—CO$_2$R$^d$,
(xi) —C≡C—R$^a$,
(xii) —O—C(=O)R$^a$,
(xiii) oxo, and
(xiv) —N(R$^b$)—C(=O)R$^a$,
(5) —C$_3$cycloalkyl, —C$_4$cycloalkyl or —C$_7$cycloalkyl, unsubstituted or substituted with 1-5 substituents each independently selected from:
(a) halo,
(b) —OR$^a$,
(c) —CN,
(d) —CO$_2$R$^a$,
(e) —C$_{1-6}$alkyl, which is unsubstituted or substituted with 1-6 halo,
(f) —C(=O)NR$^b$R$^c$,
(g) —S(O)$_v$R$^d$;
(h) —NR$^b$R$^c$,
(i) —O—CO$_2$R$^d$,
(j) —C≡C—R$^a$,
(k) —N(R$^b$)—CO$_2$R$^d$,
(l) —N(R$^b$)—SO$_2$R$^d$,
(m) —O—C(=O)R$^a$,
(n) —N(R$^b$)—C(=O)R$^a$, and
(o) phenyl or heterocycle, wherein heterocycle is selected from; pyridyl, pyrimidinyl, pyrazinyl, pyridazinyl, piperidyl, piperazinyl, pyrrolidinyl, thienyl, morpholinyl, thiazolyl, oxazolyl, isoxazolyl, furanyl, tetrahydrofuranyl, and tetrahydropyranyl, which phenyl or heterocycle is unsubstituted or substituted with 1-5 substituents each independently selected from:
(i) halo,
(ii) —$OR^a$,
(iii) —CN,
(iv) —$CO_2R^a$,
(v) —$C_{1-6}$alkyl, which is optionally substituted with 1-6 halo,
(vi) —C(=O)$NR^bR^c$,
(vii) —S(O)$_vR^d$;
(viii) —$NR^bR^c$,
(ix) —O—$CO_2R^d$,
(x) —C≡C—$R^a$,
(xi) —N($R^b$)—$CO_2R^d$,
(xii) —O—C(=O)$R^a$,
(xiii) oxo, and
(xiv) —N($R^b$)—C(=O)$R^a$, (6) —$C_5$cycloalkyl or —$C_6$cycloalkyl substituted with 1-5 substituents each independently selected from:
(a) halo,
(b) —$OR^a$,
(c) —CN,
(d) —$CO_2R^a$,
(e) —$C_{1-6}$alkyl, which is unsubstituted or substituted with 1-6 halo,
(f) —C(=O)$NR^bR^c$,
(g) —S(O)$_vR^d$;
(h) —$NR^bR^c$,
(i) —O—$CO_2R^d$,
(j) —C≡C—$R^a$,
(k) —N($R^b$)—$CO_2R^d$,
(l) —O—C(=O)$R^a$,
(m) oxo,
(n) —N($R^b$)—C(=O)$R^a$, and
(o) phenyl or heterocycle, wherein heterocycle is selected from; pyridyl, pyrimidinyl, pyrazinyl, pyridazinyl, piperidyl, piperazinyl, pyrrolidinyl, thienyl, morpholinyl, thiazolyl, oxazolyl, isoxazolyl, furanyl, tetrahydrofuranyl, and tetrahydropyranyl, which phenyl or heterocycle is unsubstituted or substituted with 1-5 substituents each independently selected from:
(i) halo,
(ii) —$OR^a$,
(iii) —CN,
(iv) —$CO_2R^a$,
(v) —$C_{1-6}$alkyl, which is optionally substituted with 1-6 halo,
(vi) —C(=O)$NR^bR^c$,
(vii) —S(O)$_vR^d$;
(viii) —$NR^bR^c$,
(ix) —O—$CO_2R^d$,
(x) —C≡C—$R^a$,
(xi) —N($R^b$)—$CO_2R^d$,
(xii) —O—C(=O)$R^a$,
(xiii) oxo, and
(xiv) —N($R^b$)—C(=O)$R^a$, (7) —$CO_2R^a$,
(8) —$NR^bR^c$,
(9) —$OR^d$, and
(10) —$C_{4-11}$bicycloalkyl or —$C_{4-15}$tricycloalkyl, where one or two non-bridge head carbons are optionally replaced with and oxygen(s), and one or two carbons may be optionally replaced with nitrogen(s), which bicyclo- or tricyclo-groups are unsubstituted or substituted with 1-4 substituents each independently selected from:
(a) halo,
(b) —$OR^a$,
(c) $CO_2R^a$,
(d) —CN,
(e) oxo, and
(f) —$C_{1-6}$alkyl, which is optionally substituted with 1-6 halo, wherein $R^a$, $R^b$, $R^c$, $R^d$, and v are defined herein.

In an embodiment of the present invention $R^9$ is independently selected from:
(1) —$C_1$alkyl, optionally substituted with 1-2 fluoro, and further substituted with 1-2 substituents which are each independently selected from:
(a) chloro,
(b) bromo,
(c) —$OR^a$,
(d) —CN,
(e) —$CO_2R^a$,
(f) —C(=O)$NR^bR^c$,
(g) —$C_{3-6}$cycloalkyl, which is unsubstituted or substituted with 1-6 halo,
(h) —C≡C—$R^a$,
(i) —N($R^b$)—$CO_2R^d$,
(j) —N($R^b$)—C(=O)$R^a$, and
(k) heterocycle, wherein heterocycle is selected from; pyridyl, pyrimidinyl, pyrazinyl, pyridazinyl, piperidyl, piperazinyl, pyrrolidinyl, thienyl, morpholinyl, thiazolyl, oxazolyl, isoxazolyl, furanyl, tetrahydrofuranyl, and tetrahydropyranyl, which heterocycle is unsubstituted or substituted with 1-3 substituents each independently selected from:
(i) halo,
(ii) —$OR^a$,
(iii) —CN,
(iv) —$CO_2R^a$,
(v) —$C_{1-6}$alkyl, which is optionally substituted with 1-6 halo,
(vi) —C(=O)$NR^bR^c$,
(vii) —$NR^bR^c$, and
(vii) —O—$CO_2R^d$, (2) —$C_{2-8}$alkyl, optionally substituted with 1-6 fluoro, and further substituted with 1-3 substituents each independently selected from:
(a) chloro,
(b) bromo,
(c) iodo,
(d) —$OR^a$,
(e) —CN,
(f) —$CO_2R^a$,
(g) —C(=O)$NR^bR^c$,
(h) —$NR^bR^c$,
(i) —C≡C—$R^a$,
(j) —N($R^b$)—C(=O)$R^a$, and
(k) phenyl or heterocycle, wherein heterocycle is selected from: pyridyl, pyrimidinyl, pyrazinyl, pyridazinyl, piperidyl, piperazinyl, pyrrolidinyl, thienyl, morpholinyl, thiazolyl, oxazolyl, isoxazolyl, furanyl, tetrahydrofuranyl, and tetrahydropyranyl, which phenyl or heterocycle is unsubstituted or substituted with 1-3 substituents each independently selected from:
(i) halo,
(ii) —$OR^a$,
(iii) —CN,
(iv) —$CO_2R^a$, (v) —$C_{1-6}$alkyl, which is optionally substituted with 1-6 halo,
(vi) —C(=O)NR$^b$R$^c$,
(vii) —NR$^b$R$^c$, and
(viii) —O—C(=O)R$^a$,
(3) benzyl or phenyl, substituted with 1-3 substituents each independently selected from:
(a) halo,
(b) —OR$^a$,
(c) —CN,
(d) —CO$_2$R$^a$,
(e) —$C_{1-6}$alkyl, which is unsubstituted or substituted with 1-6 halo,
(f) —C(=O)NR$^b$R$^c$,
(g) —NR$^b$R$^c$,
(h) —C≡C—R$^a$,
(i) —N(R$^b$)—C(=O)R$^a$, and
(j) phenyl or heterocycle, wherein heterocycle is selected from; pyridyl, pyrimidinyl, pyrazinyl, pyridazinyl, piperidyl, piperazinyl, pyrrolidinyl, thienyl, morpholinyl, thiazolyl, oxazolyl, isoxazolyl, furanyl, tetrahydrofuranyl, and tetrahydropyranyl, which phenyl or heterocycle is unsubstituted or substituted with 1-3 substituents each independently selected from:
(i) halo,
(ii) —OR$^a$,
(iii) —CN,
(iv) —CO$_2$R$^a$,
(v) —$C_{1-6}$alkyl, which is optionally substituted with 1-6 halo,
(vi) —NR$^b$R$^c$,
(vii) —O—C(=O)R$^a$,
(4) a group independently selected from: naphthyl, tetrahydronaphthyl, indanyl, biphenyl, phenanthryl, anthryl, azepinyl, azepanyl, azetidinyl, benzimidazolyl, benzisoxazolyl, benzofuranyl, benzofurazanyl, benzopyranyl, benzothiopyranyl, benzofuryl, benzothiazolyl, benzothienyl, benzoxazolyl, benzopyrazolyl, benzotriazolyl, chromanyl, cinnolinyl, dibenzofuranyl, dihydrobenzofuryl, dihydrobenzothienyl, dihydrobenzothiopyranyl, dihydrobenzothiopyranyl sulfone, furyl, furanyl, imidazolidinyl, imidazolinyl, imidazolyl, indolinyl, indolyl, isochromanyl, isoindolinyl, isoquinolinyl, isothiazolidinyl, isothiazolyl, morpholinyl, naphthyridinyl, oxadiazolyl, 2-oxoazepinyl, 4-oxonaphthyridinyl, 2-oxopiperazinyl, 2-oxopiperidinyl, 2-oxopyrrolidinyl, 2-oxopyridyl, 2-oxoquinolinyl, piperidyl, piperazinyl, pyrazinyl, pyrazolidinyl, pyrazolyl, pyridazinyl, pyridinyl, pyridyl, pyrimidinyl, pyrimidyl, pyrrolidinyl, pyrrolyl, quinazolinyl, quinolinyl, quinoxalinyl, tetrahydrofuranyl, tetrahydrofuryl, tetrahydroimidazopyridinyl, tetrahydroisoquinolinyl, tetrahydroquinolinyl, tetrazolyl, thiamorpholinyl, thiamorpholinyl sulfoxide, thiamorpholinyl sulfone, thiazolyl, thiazolinyl, thienofuryl, thienothienyl, thienyl, triazolyl, isoxazolyl, tetrahydrothienyl, tetrahydropyranyl, oxetanyl, tetrahydrothiapyranyl, and thietanyl, which group is unsubstituted or substituted with 1-5 substituents each independently selected from:
(a) halo,
(b) —OR$^a$,
(c) —CN,
(d) —CO$_2$R$^a$,
(e) —$C_{1-6}$alkyl, which is unsubstituted or substituted with 1-6 halo,
(f) —C(=O)NR$^b$R$^c$,
(g) —NR$^b$R$^c$,
(h) oxo, and
(i) phenyl or heterocycle, wherein heterocycle is selected from; pyridyl, pyrimidinyl, pyrazinyl, pyridazinyl, piperidyl, piperazinyl, pyrrolidinyl, thienyl, morpholinyl, thiazolyl, oxazolyl, isoxazolyl, furanyl, tetrahydrofuranyl, and tetrahydropyranyl, which phenyl or heterocycle is unsubstituted or substituted with 1-5 substituents each independently selected from:
(i) halo,
(ii) —OR$^a$,
(iii) —CN,
(iv) —CO$_2$R$^a$,
(v) —$C_{1-6}$alkyl, which is optionally substituted with 1-6 halo,
(vi) —C(=O)NR$^b$R$^c$,
(ix) —NR$^b$R$^c$, and
(x) —O—CO$_2$R$^d$,
(5) —$C_3$cycloalkyl, —$C_4$cycloalkyl or —$C_7$cycloalkyl, unsubstituted or substituted with 1-5 substituents each independently selected from:
(a) halo,
(b) —OR$^a$,
(c) —CN,
(d) —CO$_2$R$^a$,
(e) —$C_{1-6}$alkyl, which is unsubstituted or substituted with 1-6 halo,
(f) —C(=O)NR$^b$R$^c$,
(g) —NR$^b$R$^c$,
(h) —O—CO$_2$R$^d$,
(i) —C≡C—R$^a$,
(j) —O—C(=O)R$^a$, and
(k) phenyl or heterocycle, wherein heterocycle is selected from; pyridyl, pyrimidinyl, pyrazinyl, pyridazinyl, piperidyl, piperazinyl, pyrrolidinyl, thienyl, morpholinyl, thiazolyl, oxazolyl, isoxazolyl, furanyl, tetrahydrofuranyl, and tetrahydropyranyl, which phenyl or heterocycle is unsubstituted or substituted with 1-5 substituents each independently selected from:
(i) halo,
(ii) —OR$^a$,
(iii) —CN,
(iv) —CO$_2$R$^a$,
(v) —$C_{1-6}$alkyl, which is optionally substituted with 1-6 halo,
(vi) —C(=O)NR$^b$R$^c$,
(viii) —NR$^b$R$^c$,
(ix) —O—CO$_2$R$^d$, and
(xii) —O—C(=O)R$^a$,
(6) —$C_5$cycloalkyl or —$C_6$cycloalkyl substituted with 1-5 substituents each independently selected from:
(a) halo,
(b) —OR$^a$,
(c) —CN,
(d) —CO$_2$R$^a$,
(e) —$C_{1-6}$alkyl, which is unsubstituted or substituted with 1-6 halo,
(f) —NR$^b$R$^c$,
(g) —O—CO$_2$R$^d$,
(h) —C≡C—R$^a$,
(i) —O—C(=O)R$^a$, and
(j) phenyl or heterocycle, wherein heterocycle is selected from; pyridyl, pyrimidinyl, pyrazinyl, pyridazinyl, piperidyl, piperazinyl, pyrrolidinyl, thienyl, morpholinyl, thiazolyl, oxazolyl, isoxazolyl, furanyl, tetrahydropyranyl, and tetrahydropyranyl, which phenyl or heterocycle is unsubstituted or substituted with 1-5 substituents each independently selected from:
(i) halo,
(ii) —OR$^a$,
(iii) —CN,
(iv) —CO$_2$R$^a$,
(v) —C$_{1-6}$alkyl, which is optionally substituted with 1-6 halo,
(vi) —C(=O)NR$^b$R$^c$,
(viii) —NR$^b$R$^c$, and
(xii) —O—C(=O)R$^a$,
(7) —CO$_2$R$^a$,
(8) —NR$^b$R$^c$,
(9) —OR$^d$, and
(10) —C$_{4-11}$bicycloalkyl or —C$_{4-15}$tricycloalkyl, where one or two non-bridge head carbons
are optionally replaced with and oxygen(s), and one or two carbons may be optionally replaced with nitrogen(s), which bicyclo- or tricyclo-groups are unsubstituted or substituted with 1-4 substituents each independently selected from:
(a) halo,
(b) —OR$^a$,
(c) CO$_2$R$^a$,
(d) —CN,
(e) oxo, and
(f) —C$_{1-6}$alkyl, which is optionally substituted with 1-6 halo, wherein R$^a$, R$^c$, and R$^d$ are defined herein.

In an embodiment of the present invention R$^9$ is independently selected from:
(1) —C$_1$alkyl, optionally substituted with 1-2 fluoro, and further substituted with 1-2 substituents which are each independently selected from:
(a) chloro,
(b) bromo,
(c) —OR$^a$,
(d) —CN,
(e) —CO$_2$R$^a$,
(f) —C$_{3-6}$cycloalkyl, which is unsubstituted or substituted with 1-6 halo,
(g) —C≡C—R$^a$, and
(h) heterocycle, wherein heterocycle is selected from; pyridyl, pyrimidinyl, pyrazinyl, pyridazinyl, piperidyl, piperazinyl, pyrrolidinyl, thienyl, morpholinyl, thiazolyl, oxazolyl, isoxazolyl, furanyl, tetrahydrofuranyl, and tetrahydropyranyl, which heterocycle is unsubstituted or substituted with 1-3 substituents each independently selected from:
(i) halo,
(ii) —OR$^a$,
(iii) —CN,
(iv) —CO$_2$R$^a$,
(v) —C$_{1-6}$alkyl, which is optionally substituted with 1-6 halo,
(2) —C$_{2-8}$alkyl, optionally substituted with 1-6 fluoro, and further substituted with 1-3 substituents each independently selected from:
(a) chloro,
(b) bromo,
(c) iodo,
(d) —OR$^a$,
(e) —CN,
(f) —NR$^b$R$^c$,
(g) —C≡C—R$^a$, and
(h) phenyl or heterocycle, wherein heterocycle is selected from: pyridyl, pyrimidinyl, pyrazinyl, pyridazinyl, piperidyl, piperazinyl, pyrrolidinyl, thienyl, morpholinyl, thiazolyl, oxazolyl, isoxazolyl, furanyl, tetrahydrofuranyl, and tetrahydropyranyl, which phenyl or heterocycle is unsubstituted or substituted with 1-3 substituents each independently selected from:
(i) halo,
(ii) —OR$^a$,
(iii) —CN,
(iv) —CO$_2$R$^a$, and
(v) —C$_{1-6}$alkyl, which is optionally substituted with 1-6 halo,
(3) benzyl or phenyl, substituted with 1-3 substituents each independently selected from:
(a) halo,
(b) —OR$^a$,
(c) —CN,
(d) —CO$_2$R$^a$,
(e) —C$_{1-6}$alkyl, which is unsubstituted or substituted with 1-6 halo,
(f) —NR$^b$R$^c$, and
(g) phenyl or heterocycle, wherein heterocycle is selected from; pyridyl, pyrimidinyl, pyrazinyl, pyridazinyl, piperidyl, piperazinyl, pyrrolidinyl, thienyl, morpholinyl, thiazolyl, oxazolyl, isoxazolyl, furanyl, tetrahydrofuranyl, and tetrahydropyranyl, which phenyl or heterocycle is unsubstituted or substituted with 1-3 substituents each independently selected from:
(i) halo,
(ii) —OR$^a$,
(iii) —CN, and
(iv) —C$_{1-6}$alkyl, which is optionally substituted with 1-6 halo,
(4) a group independently selected from: naphthyl, tetrahydronaphthyl, indanyl, biphenyl, phenanthryl, anthryl, azepinyl, azepanyl, azetidinyl, benzimidazolyl, benzisoxazolyl, benzofuranyl, benzofurazanyl, benzopyranyl, benzothiopyranyl, benzofuryl, benzothiazolyl, benzothienyl, benzoxazolyl, benzopyrazolyl, benzotriazolyl, chromanyl, cinnolinyl, dibenzofuranyl, dihydrobenzofuryl, dihydrobenzothienyl, dihydrobenzothiopyranyl, dihydrobenzothiopyranyl sulfone, furyl, furanyl, imidazolidinyl, imidazolinyl, imidazolyl, indolinyl, indolyl, isochromanyl, isoindolinyl, isoquinolinyl, isothiazolidinyl, isothiazolyl, morpholinyl, naphthyridinyl, oxadiazolyl, 2-oxoazepinyl, 4-oxonaphthyridinyl, 2-oxopiperazinyl, 2-oxopiperidinyl, 2-oxopyrrolidinyl, 2-oxopyridyl, 2-oxoquinolinyl, piperidyl, piperazinyl, pyrazinyl, pyrazolidinyl, pyrazolyl, pyridazinyl, pyridinyl, pyridyl, pyrimidinyl, pyrimidyl, pyrrolidinyl, pyrrolyl, quinazolinyl, quinolinyl, quinoxalinyl, tetrahydrofuranyl, tetrahydrofuryl, tetrahydroimidazopyridinyl, tetrahydroisoquinolinyl, tetrahydroquinolinyl, tetrazolyl, thiamorpholinyl, thiamorpholinyl sulfoxide, thiamorpholinyl sulfone, thiazolyl, thiazolinyl, thienofuryl, thienothienyl, thienyl, triazolyl, isoxazolyl, tetrahydrothienyl, tetrahydropyranyl, oxetanyl, tetrahydrothiapyranyl, and thietanyl, which group is unsubstituted or substituted with 1-5 substituents each independently selected from:
(a) halo,
(b) —OR$^a$,
(c) —CN,
(d) —CO$_2$R$^a$, (e) —$C_{1-6}$alkyl, which is unsubstituted or substituted with 1-6 halo,
(f) —$NR^bR^c$,
(h) oxo, and
(i) phenyl or heterocycle, wherein heterocycle is selected from; pyridyl, pyrimidinyl, pyrazinyl, pyridazinyl, piperidyl, piperazinyl, pyrrolidinyl, thienyl, morpholinyl, thiazolyl, oxazolyl, isoxazolyl, furanyl, tetrahydrofuranyl, and tetrahydropyranyl, which phenyl or heterocycle is unsubstituted or substituted with 1-5 substituents each independently selected from:
(i) halo,
(ii) —$OR^a$,
(iii) —CN,
(iv) —$CO_2R^a$, and
(v) —$C_{1-6}$alkyl, which is optionally substituted with 1-6 halo,
(5) —$C_3$cycloalkyl, or —$C_4$cycloalkyl, unsubstituted or substituted with 1-5 substituents each independently selected from:
(a) halo,
(b) —$OR^a$,
(c) —CN,
(d) —$CO_2R^a$,
(e) —$C_{1-6}$alkyl, which is unsubstituted or substituted with 1-6 halo,
(f) —$NR^bR^c$,
(g) —C≡C—$R^a$, and
(h) phenyl or heterocycle, wherein heterocycle is selected from; pyridyl, pyrimidinyl, pyrazinyl, pyridazinyl, piperidyl, piperazinyl, pyrrolidinyl, thienyl, morpholinyl, thiazolyl, oxazolyl, isoxazolyl, furanyl, tetrahydrofuranyl, and tetrahydropyranyl, which phenyl or heterocycle is unsubstituted or substituted with 1-5 substituents each independently selected from:
(i) halo,
(ii) —$OR^a$,
(iii) —CN,
(iv) —$CO_2R^a$, and
(v) —$C_{1-6}$alkyl, which is optionally substituted with 1-6 halo,
(6) —$C_5$cycloalkyl or —$C_6$cycloalkyl substituted with 1-5 substituents each independently selected from:
(a) halo,
(b) —$OR^a$,
(c) —CN,
(d) —$CO_2R^a$,
(e) —$C_{1-6}$alkyl, which is unsubstituted or substituted with 1-6 halo,
(f) —$NR^bR^c$, and
(g) phenyl or heterocycle, wherein heterocycle is selected from; pyridyl, pyrimidinyl, pyrazinyl, pyridazinyl, piperidyl, piperazinyl, pyrrolidinyl, thienyl, morpholinyl, thiazolyl, oxazolyl, isoxazolyl, furanyl, tetrahydrofuranyl, and tetrahydropyranyl, which phenyl or heterocycle is unsubstituted or substituted with 1-5 substituents each independently selected from:
(i) halo,
(ii) —$OR^a$,
(iii) —CN,
(iv) —$CO_2R^a$, and
(v) —$C_{1-6}$alkyl, which is optionally substituted with 1-6 halo,
(7) —$NR^bR^c$, and
(8) —$C_{4-11}$bicycloalkyl or —$C_{4-15}$tricycloalkyl, where one or two non-bridge head carbons
are optionally replaced with and oxygen(s), and one or two carbons may be optionally replaced with nitrogen(s), which bicyclo- or tricyclo-groups are unsubstituted or substituted with 1-4 substituents each independently selected from:
(a) halo,
(b) —$OR^a$,
(c) $CO_2R^a$,
(d) —CN,
(e) oxo, and
(f) —$C_{1-6}$alkyl, which is optionally substituted with 1-6 halo, wherein $R^a$, $R^c$, and $R^d$ are defined herein.

In an embodiment of the present invention $R^9$ is independently selected from the group consisting of:
naphthyl, tetrahydronaphthyl, indanyl, biphenyl, phenanthryl, anthryl, azepinyl, azepanyl, azetidinyl, benzimidazolyl, benzisoxazolyl, benzofuranyl, benzofurazanyl, benzopyranyl, benzothiopyranyl, benzofuryl, benzothiazolyl, benzothienyl, benzoxazolyl, benzopyrazolyl, benzotriazolyl, chromanyl, cinnolinyl, dibenzofuranyl, dihydrobenzofuryl, dihydrobenzothienyl, dihydrobenzothiopyranyl, dihydrobenzothiopyranyl sulfone, furyl, furanyl, imidazolidinyl, imidazolinyl, imidazolyl, indolinyl, indolyl, isochromanyl, isoindolinyl, isoquinolinyl, isothiazolidinyl, isothiazolyl, morpholinyl, naphthyridinyl, oxadiazolyl, 2-oxoazepinyl, 4-oxonaphthyridinyl, 2-oxopiperazinyl, 2-oxopiperidinyl, 2-oxopyrrolidinyl, 2-oxopyridyl, 2-oxoquinolinyl, piperidyl, piperazinyl, pyrazinyl, pyrazolidinyl, pyrazolyl, pyridazinyl, pyridinyl, pyridyl, pyrimidinyl, pyrimidyl, pyrrolidinyl, pyrrolyl, quinazolinyl, quinolinyl, quinoxalinyl, tetrahydrofuranyl, tetrahydrofuryl, tetrahydroimidazopyridinyl, tetrahydroisoquinolinyl, tetrahydroquinolinyl, tetrazolyl, thiamorpholinyl, thiamorpholinyl sulfoxide, thiamorpholinyl sulfone, thiazolyl, thiazolinyl, thienofuryl, thienothienyl, thienyl, triazolyl, isoxazolyl, tetrahydrothienyl, tetrahydropyranyl, oxetanyl, tetrahydrothiapyranyl, and thietanyl, which group is unsubstituted or substituted with 1-5 substituents each independently selected from:
(a) halo,
(b) —$OR^a$,
(c) —CN,
(d) —$CO_2R^a$,
(e) —$C_{1-6}$alkyl, which is unsubstituted or substituted with 1-6 halo,
(f) —$NR^bR^c$,
(h) oxo, and
(i) phenyl or heterocycle, wherein heterocycle is selected from; pyridyl, pyrimidinyl, pyrazinyl, pyridazinyl, piperidyl, piperazinyl, pyrrolidinyl, thienyl, morpholinyl, thiazolyl, oxazolyl, isoxazolyl, furanyl, tetrahydrofuranyl, and tetrahydropyranyl, which phenyl or heterocycle is unsubstituted or substituted with 1-5 substituents each independently selected from:
(i) halo,
(ii) —$OR^d$,
(iii) —CN,
(iv) —$CO_2R^a$, and
(v) —$C_{1-6}$alkyl, which is optionally substituted with 1-6 halo, wherein $R^a$, $R^b$,
and $R^c$, are defined herein.

In an embodiment of the present invention $R^9$ is —$C_3$cycloalkyl, or —$C_4$cycloalkyl, unsubstituted or substituted with 1-5 substituents each independently selected from:
(a) halo,
(b) —$OR^a$,
(c) —CN,
(d) —$CO_2R^a$,
(e) —$C_{1-6}$alkyl, which is unsubstituted or substituted with 1-6 halo,
(f) —$NR^bR^c$,
(g) —C≡C—$R^a$, and
(h) phenyl or heterocycle, wherein heterocycle is selected from; pyridyl, pyrimidinyl, pyrazinyl, pyridazinyl, piperidyl, piperazinyl, pyrrolidinyl, thienyl, morpholinyl, thiazolyl, oxazolyl, isoxazolyl, furanyl, tetrahydrofuranyl, and tetrahydropyranyl, which phenyl or heterocycle is unsubstituted or substituted with 1-5 substituents each independently selected from:
(i) halo,
(ii) —$OR^a$,
(iii) —CN,
(iv) —$CO_2R^a$, and
(v) —$C_{1-6}$alkyl, which is optionally substituted with 1-6 halo, wherein $R^a$, $R^b$, and $R^c$, are defined herein.

In an embodiment of the present invention $R^9$ is —$C_{4-11}$bicycloalkyl or —$C_{4-15}$tricycloalkyl, where one or two non-bridge head carbons are optionally replaced with and oxygen(s), and one or two carbons may be optionally replaced with nitrogen(s), which bicyclo- or tricyclo-groups are unsubstituted or substituted with 1-4 substituents each independently selected from:
(a) halo,
(b) —$OR^a$,
(c) $CO_2R^a$,
(d) —CN,
(e) oxo, and
(f) $C_{1-6}$alkyl, which is optionally substituted with 1-6 halo, wherein $R^a$ is defined herein.

In an embodiment of the present invention $R^{11}$ is independently selected from the group consisting of:
$C_{3-10}$cycloalkyl, phenyl, naphthyl, tetrahydronaphthyl, indanyl, biphenyl, phenanthryl, anthryl, azepinyl, azetidinyl, benzimidazolyl, benzisoxazolyl, benzofuranyl, benzofurazanyl, benzopyranyl, benzothiopyranyl, benzofuryl, benzothiazolyl, benzothienyl, benzoxazolyl, benzopyrazolyl, benzotriazolyl, chromanyl, cinnolinyl, dibenzofuranyl, dihydrobenzofuryl, dihydrobenzothienyl, dihydrobenzothiopyranyl, dihydrobenzothiopyranyl sulfone, furyl, furanyl, imidazolidinyl, imidazolinyl, imidazolyl, indolinyl, indolyl, isochromanyl, isoindolinyl, isoquinolinyl, isothiazolidinyl, isothiazolyl, morpholinyl, naphthyridinyl, oxadiazolyl, 2-oxoazepinyl, 4-oxonaphthyridinyl, 2-oxopiperazinyl, 2-oxopiperidinyl, 2-oxopyrrolidinyl, 2-oxopyridyl, 2-oxoquinolinyl, piperidyl, piperazinyl, pyrazinyl, pyrazolidinyl, pyrazolyl, pyridazinyl, pyridinyl, pyridyl, pyrimidinyl, pyrimidyl, pyrrolidinyl, pyrrolyl, quinazolinyl, quinolinyl, quinoxalinyl, tetrahydrofuranyl, tetrahydrofuryl, tetrahydroimidazopyridinyl, tetrahydroisoquinolinyl, tetrahydroquinolinyl, tetrazolyl, thiazolyl, thiamorpholinyl sulfoxide, thiazolyl, thiazolinyl, thienofuryl, thienothienyl, thienyl, and triazolyl, where $R^{11}$ is unsubstituted or substituted with 1-5 substituents each independently selected from $R^{12}$, $R^{13}$, $R^{14}$, $R^{15a}$ and $R^{15b}$, wherein $R^{12}$, $R^{13}$, $R^{14}$, $R^{15a}$ and $R^{15b}$ are defined herein.

In an embodiment of the present invention $R^{11}$ is independently selected from the group consisting of:
$C_{3-10}$cycloalkyl, phenyl, naphthyl, tetrahydronaphthyl, indanyl, biphenyl, benzimidazolyl, benzisoxazolyl, furyl, furanyl, imidazolidinyl, imidazolinyl, imidazolyl, indolinyl, indolyl, morpholinyl, naphthyridinyl, piperidyl, piperazinyl, pyrazinyl, pyrazolidinyl, pyrazolyl, pyridazinyl, pyridinyl, pyridyl, pyrimidinyl, pyrimidyl, pyrrolidinyl, pyrrolyl, quinazolinyl, quinolinyl, tetrahydrofuranyl, tetrahydroisoquinolinyl, tetrahydroquinolinyl, thiazolinyl, thienyl, and triazolyl, where $R^{11}$ is unsubstituted or substituted with 1-5 substituents each independently selected from $R^{12}$, $R^{13}$, $R^{14}$, $R^{15a}$ and $R^{15b}$, wherein $R^{12}$, $R^{13}$, $R^{14}$, $R^{15a}$ and $R^{15b}$ are defined herein.

In an embodiment of the present invention $R^{11}$ is independently selected from the group consisting of:
$C_{4-9}$cycloalkyl, phenyl, tetrahydronaphthyl, indanyl, indolinyl, indolyl, morpholinyl, pyridyl, pyrimidinyl, pyrimidyl, pyrrolidinyl, pyrrolyl, quinazolinyl, quinolinyl, tetrahydrofuranyl, thienyl, and triazolyl, where $R^{11}$ is unsubstituted or substituted with 1-5 substituents each independently selected from $R^{12}$, $R^{13}$, $R^{14}$, $R^{15a}$ and $R^{15b}$, wherein $R^{12}$, $R^{13}$, $R^{14}$, $R^{15a}$ and $R^{15b}$ are defined herein.

In an embodiment of the present invention $R^H$ is independently selected from the group consisting of:
$C_{5-8}$cycloalkyl, phenyl, tetrahydronaphthyl, indanyl, indolinyl, indolyl, tetrahydrofuranyl, and thienyl, where $R^{11}$ is unsubstituted or substituted with 1-5 substituents each independently selected from $R^{12}$, $R^{13}$, $R^{14}$, $R^{15a}$ and $R^{15b}$, wherein $R^{12}$, $R^{13}$, $R^{14}$, $R^{15a}$ and $R^{15b}$ are defined herein.

In an embodiment of the present invention $R^{11}$ is independently selected from the group consisting of:
$C_{5-8}$cycloalkyl, phenyl, tetrahydronaphthyl, and indanyl, where $R^{11}$ is unsubstituted or substituted with 1-5 substituents each independently selected from $R^{12}$, $R^{13}$, $R^{14}$, $R^{15a}$ and $R^{15b}$, wherein $R^{12}$, $R^{13}$, $R^{14}$, $R^{15a}$ and $R^{15b}$ are defined herein.

In an embodiment of the present invention $R^{PG}$ is selected from:
(1) hydrogen,
(2) —$CH_2OR^a$,
(3) —$CH_2$—O—$CH_2CH_2Si(CH_3)_3$,
(4) —$C_{1-6}$alkyl which is unsubstituted or substituted with 1-5 halo,
(5) —$CH_2$—O—$P(=O)(OR^a)_2$, wherein $R^a$ is defined herein.

In an embodiment of the present invention $R^{PG}$ is selected from:
(1) hydrogen,
(2) —$C_{1-6}$alkyl which is unsubstituted or substituted with 1-5 halo,
(3) —$CH_2$—O—$P(=O)(OR^a)_2$, wherein $R^a$ is defined herein.

In an embodiment of the present invention $R^{PG}$ is hydrogen.

In an embodiment of the present invention $R^{PG}$ is methyl.

In an embodiment of the present invention $R^{PG}$ is —$CH_2$—O—$P(=O)(OH)_2$.

In an embodiment of the present invention J is =$C(R^{16a})$—, —$CR^{17}R^{18}$— or —$N(R^b)$—, wherein $R^{16a}$, $R^{17}$, $R^{18}$ and $R^b$ are defined herein.

In an embodiment of the present invention J is =C($R^{16a}$)—, wherein $R^{16a}$ is defined herein.

In an embodiment of the present invention J is —C$R^{17}R^{18}$—, wherein $R^{17}$ and $R^{18}$ are defined herein.

In an embodiment of the present invention J is —CH$_2$—.

In an embodiment of the present invention J is —N($R^b$)—, wherein $R^b$ is defined herein.

In an embodiment of the present invention J is —N(CH$_3$)—.

In an embodiment of the present invention Y is =C($R^{16b}$)—, —C$R^{17}R^{18}$— or —C(=O)—, wherein $R^{16b}$, $R^{17}$ and $R^{18}$ are defined herein.

In an embodiment of the present invention Y is =C($R^{16b}$)—, wherein $R^{16b}$ is defined herein.

In an embodiment of the present invention Y is —C(=O)—.

In an embodiment of the present invention $R^{16a}$ and $R^{16b}$ are independently selected from:
(1) hydrogen,
(2) —C$_{1-4}$alkyl, which is unsubstituted or substituted with 1-3 substituents each independently selected from: halo, —O$R^a$, —C$_{3-6}$cycloalkyl, and phenyl,
(3) phenyl or heterocycle, wherein heterocycle is selected from: pyridyl, pyrimidinyl, pyrazinyl, thiazolyl, thienyl, triazolyl, isoxazolyl and morpholinyl, which phenyl or heterocycle is unsubstituted or substituted with 1-3 substituents each independently selected from: —C$_{1-4}$alkyl which is unsubstituted or substituted with 1-3 halo, —O$R^a$, and halo,
(4) halo,
(5) O$R^a$, and
(6) —N$R^bR^c$, wherein $R^a$, $R^b$ and $R^c$ are defined herein.

In an embodiment of the present invention $R^{16a}$ and $R^{16b}$ are independently selected from:
(1) hydrogen,
(2) —C$_{1-4}$alkyl, which is unsubstituted or substituted with 1-3 fluoro, and
(3) phenyl or heterocycle, wherein heterocycle is selected from: pyridyl, pyrimidinyl, pyrazinyl, thiazolyl, thienyl, triazolyl, isoxazolyl and morpholinyl.

In an embodiment of the present invention $R^{16a}$ and $R^{16b}$ and the atom(s) to which they are attached join to form a ring selected from cyclohexenyl, phenyl, pyridyl, pyrimidinyl, pyrazinyl, pyridazinyl, furanyl, oxazolyl, isoxazolyl, imidazolyl, and thienyl, which ring is unsubstituted or substituted with 1-3 substituents each independently selected from:
(1) —C$_{1-6}$alkyl, which is unsubstituted or substituted with 1-3 substituents each independently selected from: halo, O$R^a$, —CO$_2R^a$, —N$R^bR^c$, and CON$R^bR^c$,
(2) phenyl or heterocycle, wherein heterocycle is selected from pyridyl, pyrimidinyl, pyrazinyl, pyridazinyl, piperidinyl, azetidinyl, piperazinyl, pyrrolidinyl, thienyl and morpholinyl, which phenyl or heterocycle is unsubstituted or substituted with 1-3 substituents each independently selected from: halo, O$R^a$ and —C$_{1-4}$alkyl, which is unsubstituted or substituted with 1-3 fluoro,
(3) halo,
(4) O$R^a$,
(5) —CN,
(6) —N$R^bR^c$,
(7) CON$R^bR^c$, and
(8) oxo, wherein $R^a$, $R^b$ and $R^c$ are defined herein.

In an embodiment of the present invention $R^{16a}$ and $R^{16b}$ and the atom(s) to which they are attached join to form a ring selected from phenyl, pyridyl, and pyrimidinyl, which ring is unsubstituted or substituted with 1-3 substituents independently selected from: halo, O$R^a$ and —C$_{1-4}$alkyl, which is unsubstituted or substituted with 1-3 fluoro, wherein $R^a$ is defined herein.

In an embodiment of the present invention $R^{16a}$ and $R^{16b}$ and the atom(s) to which they are attached join to form a ring selected from pyridyl, and pyrimidinyl.

In an embodiment of the present invention $R^{21}$ is independently selected from:
(1) —C≡C—$R^a$,
(2) —C$_{1-7}$alkyl, which is unsubstituted or substituted with 1-5 substituents each independently selected from:
   (a) halo,
   (b) —O$R^a$,
   (c) —CN,
   (d) —CO$_2R^a$,
   (e) —C$_{1-6}$alkyl, which is unsubstituted or substituted with 1-6 halo,
   (f) —N$R^bR^c$,
   (g) —N($R^b$)—CO$_2R^d$,
   (h) —O—C(=O)$R^a$,
   (i) oxo, and
   (j) —N($R^b$)—C(=O)$R^a$,
(3) a group independently selected from: isoxazolyl, tetrahydrothienyl, thiamorpholinyl sulfone, thiadiazolyl, quinuclidinyl, norbornyl, adamantyl, tetrahydropyranyl, and azepanyl, which is unsubstituted or substituted with 1-5, substituents each independently selected from $R^{12}$, $R^{13}$, $R^{14}$, $R^{15a}$, and $R^{15b}$ wherein $R^a$, $R^b$, $R^c$, $R^d$, $R^{12}$, $R^{13}$, $R^{14}$, $R^{15a}$, and $R^{15b}$ are defined herein.

In an embodiment of the present invention $R^{21}$ is independently selected from:
(1) —C≡C—$R^a$,
(2) —C$_{1-7}$alkyl, which is unsubstituted or substituted with 1-5 substituents each independently selected from:
   (a) halo,
   (b) —O$R^a$,
   (c) —CN, and
   (d) —C$_{1-6}$alkyl, which is unsubstituted or substituted with 1-6 halo,
(3) a group independently selected from: norbornyl, adamantyl, tetrahydropyranyl, and azepanyl, which is unsubstituted or substituted with 1-5 substituents each independently selected from $R^{12}$, $R^{13}$, $R^{14}$, $R^{15a}$, and $R^{15b}$, wherein $R^a$, $R^{12}$, $R^{13}$, $R^{14}$, $R^{15a}$, and $R^{15b}$ are defined herein.

In an embodiment of the present invention $R^{21}$ is —C≡C—$R^a$, wherein $R^a$ is defined herein.

In an embodiment of the present invention $R^{21}$ is adamantly or tetrahydropyranyl, which is unsubstituted or substituted with 1-5 substituents each independently selected from $R^{12}$, $R^{13}$, $R^{14}$, $R^{15a}$, and $R^{15b}$, wherein $R^{12}$, $R^{13}$, $R^{14}$, $R^{15a}$, and $R^{15b}$ are defined herein.

In an embodiment of the present invention $R^{29}$ is independently selected from:
(1) —C$_{1-6}$alkyl, which is unsubstituted or substituted with 1-5 substituents each independently selected from:
   (a) halo,
   (b) —O$R^a$,
   (c) —CN,
   (d) —CO$_2R^a$,
   (e) —C$_{1-6}$alkyl, which is unsubstituted or substituted with 1-6 halo,
   (f) —C(=O)N$R^bR^c$,
   (g) —C$_{3-6}$cycloalkyl, which is unsubstituted or substituted with 1-6 halo,
   (h) —N$R^bR^c$,
   (i) —O—CO$_2R^d$, (j) —C≡C—R$^a$,
(k) oxo,
(l) —N(R$^b$)—C(=O)R$^a$, and
(m) phenyl or heterocycle, wherein heterocycle is selected from; pyridyl, pyrimidinyl, pyrazinyl, pyridazinyl, piperidyl, piperazinyl, pyrrolidinyl, thienyl, morpholinyl, thiazolyl, oxazolyl, isoxazolyl, furanyl, tetrahydrofuranyl, or tetrahydropyranyl, which phenyl or heterocycle is unsubstituted or substituted with 1-5 substituents each independently selected from:
  (i) halo,
  (ii) —OR$^a$,
  (iii) —CN,
  (iv) —CO$_2$R$^a$,
  (v) —C$_{1-6}$alkyl, which is optionally substituted with 1-6 halo,
  (vi) —C(=O)NR$^b$R$^c$,
  (vii) —C$_{3-6}$cycloalkyl, which optionally substituted with 1-6 halo,
  (viii) —NR$^b$R$^c$,
  (xiv) oxo, and
  (x) —N(R$^b$)—C(=O)R$^a$,
(2) a group independently selected from: C$_{3-10}$cycloalkyl, phenyl, naphthyl, tetrahydronaphthyl, indanyl, biphenyl, phenanthryl, anthryl, azepinyl, azepanyl, azetidinyl, benzimidazolyl, benzisoxazolyl, benzofuranyl, benzofurazanyl, benzopyranyl, benzothiopyranyl, benzofuryl, benzothiazolyl, benzothienyl, benzoxazolyl, benzopyrazolyl, benzotriazolyl, chromanyl, cinnolinyl, dibenzofuranyl, dihydrobenzofuryl, dihydrobenzothienyl, dihydrobenzothiopyranyl, dihydrobenzothiopyranyl sulfone, furyl, furanyl, imidazolidinyl, imidazolinyl, imidazolyl, indolinyl, indolyl, isochromanyl, isoindolinyl, isoquinolinyl, isothiazolidinyl, isothiazolyl, morpholinyl, naphthyridinyl, oxadiazolyl, 2-oxoazepinyl, 4-oxonaphthyridinyl, 2-oxopiperazinyl, 2-oxopiperidinyl, 2-oxopyrrolidinyl, 2-oxopyridyl, 2-oxoquinolinyl, piperidyl, piperazinyl, pyrazinyl, pyrazolidinyl, pyrazolyl, pyridazinyl, pyridinyl, pyridyl, pyrimidinyl, pyrimidyl, pyrrolidinyl, pyrrolyl, quinazolinyl, quinolinyl, quinoxalinyl, tetrahydrofuranyl, tetrahydrofuryl, tetrahydroimidazopyridinyl, tetrahydroisoquinolinyl, tetrahydroquinolinyl, tetrazolyl, thiamorpholinyl, thiamorpholinyl sulfoxide, thiamorpholinyl sulfone, thiazolyl, thiazolinyl, thienofuryl, thienothienyl, thienyl, triazolyl, isoxazolyl, tetrahydrothienyl, tetrahydropyranyl, oxetanyl, tetrahydrothiapyranyl, and thietanyl, which group is unsubstituted or substituted with 1-5 substituents each independently selected from:
  (a) halo,
  (b) —OR$^a$,
  (c) —CN,
  (d) —CO$_2$R$^a$,
  (e) —C$_{1-6}$alkyl, which is unsubstituted or substituted with 1-6 halo,
  (f) —C(=O)NR$^b$R$^c$,
  (g) —C$_{3-6}$cycloalkyl, which is unsubstituted or substituted with 1-6 halo,
  (h) —NR$^b$R$^c$,
  (i) —O—C(=O)R$^a$,
  (j) oxo,
  (k) —N(R$^b$)—C(=O)R$^a$, and
  (l) phenyl or heterocycle, wherein heterocycle is selected from; pyridyl, pyrimidinyl, pyrazinyl, pyridazinyl, piperidyl, piperazinyl, pyrrolidinyl, thienyl, morpholinyl, thiazolyl, oxazolyl, isoxazolyl, furanyl, tetrahydrofuranyl, or tetrahydropyranyl, which phenyl or heterocycle is unsubstituted or substituted with 1-5 substituents each independently selected from:
    (i) halo,
    (ii) —OR$^a$,
    (iii) —CN,
    (iv) —CO$_2$R$^a$,
    (v) —C$_{1-6}$alkyl, which is optionally substituted with 1-6 halo,
    (vi) —C(=O)NR$^b$R$^c$,
    (vii) —NR$^b$R$^c$,
    (viii) —O—C(=O)R$^a$,
    (xiv) oxo, and
    (x) —N(R$^b$)—C(=O)R$^a$,
(3) —CO$_2$R$^a$,
(4) —NR$^b$R$^c$,
(5) hydrogen,
(6) —OR$^d$, and
(7) —C$_{4-11}$bicycloalkyl or —C$_{4-15}$-tricycloalkyl, where one or two non-bridge head carbons
  are optionally replaced with and oxygen(s), and one or two carbons may be optionally replaced with nitrogen(s), which bicyclo- or tricyclo-groups are unsubstituted or substituted with 1-4 substituents each independently selected from:
  (a) halo,
  (b) —OR$^a$,
  (c) CO$_2$R$^a$,
  (d) oxo,
  (e) —CN, and
  (f) —C$_{1-6}$alkyl, which is optionally substituted with 1-6 halo, wherein R$^a$, R$^b$, R$^c$, and R$^d$ are defined herein.

In an embodiment of the present invention R$^{29}$ is independently selected from:
(1) —C$_{1-6}$alkyl, which is unsubstituted or substituted with 1-5 substituents each independently selected from:
  (a) halo,
  (b) —OR$^a$,
  (c) —CN,
  (d) —CO$_2$R$^a$,
  (e) —C$_{1-6}$alkyl, which is unsubstituted or substituted with 1-6 halo,
  (f) —C$_{3-6}$cycloalkyl, which is unsubstituted or substituted with 1-6 halo,
  (g) —C≡C—R$^a$, and
  (h) phenyl or heterocycle, wherein heterocycle is selected from; pyridyl, pyrimidinyl, pyrazinyl, pyridazinyl, piperidyl, piperazinyl, pyrrolidinyl, thienyl, morpholinyl, furanyl, tetrahydrofuranyl, or tetrahydropyranyl, which phenyl or heterocycle is unsubstituted or substituted with 1-5 substituents each independently selected from:
    (i) halo,
    (ii) —OR$^a$,
    (iii) —CN,
    (iv) —CO$_2$R$^a$,
    (v) —C$_{1-6}$alkyl, which is optionally substituted with 1-6 halo, and
    (vi) —C$_{3-6}$cycloalkyl, which optionally substituted with 1-6 halo,
(2) a group independently selected from: C$_{3-6}$cycloalkyl, phenyl, naphthyl, tetrahydronaphthyl, azepinyl, azepanyl, azetidinyl, cinnolinyl, furyl, furanyl, imidazolyl, indolinyl, indolyl, isoindolinyl, isoquinolinyl, morpholinyl, naphthyridinyl, piperidyl, piperazinyl, pyridinyl, pyridyl, pyrrolidinyl, pyrrolyl, quinolinyl, tetrahydrofuranyl, tetrahydrofuryl, tetrahydroisoquinolinyl, tetrahydroquinolinyl, tetrazolyl, thiamorpholinyl, thienyl, triazolyl, isoxazolyl, tetrahydrothienyl, tetrahydropyranyl, oxetanyl, tetrahydrothiapyranyl, and thietanyl, which group is unsubstituted or substituted with 1-5 substituents each independently selected from:
(a) halo,
(b) —$OR^a$,
(c) —CN,
(d) —$CO_2R^a$,
(e) —$C_{1-6}$alkyl, which is unsubstituted or substituted with 1-6 halo,
(f) —$C_{3-6}$cycloalkyl, which is unsubstituted or substituted with 1-6 halo,
(g) —$NR^bR^c$, and
(h) phenyl or heterocycle, wherein heterocycle is selected from; pyridyl, pyrimidinyl, pyrazinyl, pyridazinyl, piperidyl, piperazinyl, pyrrolidinyl, thienyl, morpholinyl, thiazolyl, oxazolyl, isoxazolyl, furanyl, tetrahydrofuranyl, or tetrahydropyranyl, which phenyl or heterocycle is unsubstituted or substituted with 1-5 substituents each independently selected from:
(i) halo,
(ii) —$OR^a$,
(iii) —CN,
(iv) —$CO_2R^a$,
(v) —$C_{1-6}$alkyl, which is optionally substituted with 1-6 halo, and
(vi) —$NR^bR^c$,
(3) —$NR^bR^c$,
(4) —$OR^d$, and
(5) —$C_{4-11}$bicycloalkyl or —$C_{4-15}$tricycloalkyl, where one or two non-bridge head carbons are optionally replaced with and oxygen(s), and one or two carbons may be optionally replaced with nitrogen(s), which bicyclo- or tricyclo-groups are unsubstituted or substituted with 1-4 substituents each independently selected from:
(a) halo,
(b) —$OR^a$,
(c) $CO_2R^a$,
(d) oxo,
(e) —CN, and
(f) —$C_{1-6}$alkyl, which is optionally substituted with 1-6 halo, wherein $R^a$, $R^b$, and $R^c$ are defined herein.

In an embodiment of the present invention $R^{29}$ is —$C_{1-6}$alkyl, which is unsubstituted or substituted with 1-5 substituents each independently selected from:
(a) halo,
(b) —$OR^a$,
(c) —CN,
(d) —$CO_2R^a$,
(e) —$C_{1-6}$alkyl, which is unsubstituted or substituted with 1-6 halo,
(f) —$C_{3-6}$cycloalkyl, which is unsubstituted or substituted with 1-6 halo,
(g) —C≡C—$R^a$, and
(h) phenyl or heterocycle, wherein heterocycle is selected from; pyridyl, pyrimidinyl, pyrazinyl, pyridazinyl, piperidyl, piperazinyl, pyrrolidinyl, thienyl, morpholinyl, (uranyl, tetrahydrofuranyl, or tetrahydropyranyl, which phenyl or heterocycle is unsubstituted or substituted with 1-5 substituents each independently selected from:
(i) halo,
(ii) —$OR^a$,
(iii) —CN,
(iv) —$CO_2R^a$,
(v) —$C_{1-6}$alkyl, which is optionally substituted with 1-6 halo, and
(vi) —$C_{3-6}$cycloalkyl, which optionally substituted with 1-6 halo wherein $R^a$, $R^b$, and $R^c$ are defined herein.

In an embodiment of the present invention $R^{29}$ is independently selected from: $C_{3-6}$cycloalkyl, phenyl, furanyl, indolinyl, indolyl, morpholinyl, piperidyl, pyridyl, pyrrolidinyl, pyrrolyl, quinolinyl, tetrahydrofuranyl, and thienyl, which group is unsubstituted or substituted with 1-5 substituents each independently selected from:
(a) halo,
(b) —$OR^a$,
(c) —CN,
(d) —$CO_2R^a$,
(e) —$C_{1-6}$alkyl, which is unsubstituted or substituted with 1-6 halo,
(f) —$C_{3-6}$cycloalkyl, which is unsubstituted or substituted with 1-6 halo,
(g) —$NR^bR^c$, and
(h) phenyl or heterocycle, wherein heterocycle is selected from; pyridyl, pyrimidinyl, pyrazinyl, piperidyl, piperazinyl, pyrrolidinyl, morpholinyl, thiazolyl, tetrahydrofuranyl, or tetrahydropyranyl, which phenyl or heterocycle is unsubstituted or substituted with 1-5 substituents each independently selected from:
(i) halo,
(ii) —$OR^a$,
(iii) —CN,
(iv) —$CO_2R^a$,
(v) —$C_{1-6}$alkyl, which is optionally substituted with 1-6 halo, and
(vi) —$NR^bR^c$, wherein $R^a$, $R^b$, and $R^c$ are defined herein.

In an embodiment of the present invention $R^{29}$ is —$C_{4-11}$bicycloalkyl or —$C_{4-15}$tricycloalkyl, where one or two non-bridge head carbons are optionally replaced with and oxygen(s), and one or two carbons may be optionally replaced with nitrogen(s), which bicyclo- or tricyclo-groups are unsubstituted or substituted with 1-4 substituents each independently selected from:
(a) halo,
(b) —$OR^a$,
(c) $CO_2R^a$,
(d) oxo,
(e) —CN, and
(f) —$C_{1-6}$alkyl, which is optionally substituted with 1-6 halo, wherein $R^a$ is defined herein.

In an embodiment of the present invention m is 1.
In an embodiment of the present invention n is 1.
In an embodiment of the present invention n is 2.
In an embodiment of the present invention k is 1.
In an embodiment of the present invention k is 0.

It is to be understood that where one or more of the above recited structures or substructures recite multiple substituents having the same designation each such variable may be the same or different from each similarly designated variable. For example, if $R^{12}$ is recited four times in a particular embodiment formula I, each $R^{12}$ in formula I may independently be any of the substructures defined under $R^{12}$. As another example, in Formula I the radical —$C(halo)_2$- is recired, and each of the two halogen may be different, such that —$C(halo)_2$- may represent —CFCl—. Thus, the invention is not limited to structures and substructures wherein each multiply recited variable must be the same for a given structure. The same is true with respect to any variable appearing multiple times in a structure or substructure.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds.

Some of the compounds described herein contain olefinic double bonds, and unless specified otherwise, are meant to include both E and Z geometric isomers.

The present invention includes compounds of formula I wherein on or more hydrogen atoms are replaced by deuterium.

Tautomers of compounds defined in Formula I are also included within the scope of the present invention. For example, compounds including carbonyl —CH$_2$C(O)— groups (keto forms) may undergo tautomerism to form hydroxyl —CH=C(OH)— groups (enol forms). Both keto and enol forms are included within the scope of the present invention.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

As will be appreciated by those of skill in the art, not all of the $R^{10}$ and $R^{11}$ substituents are capable of forming a ring structure. Moreover, even those substituents capable of ring formation may or may not form a ring structure.

Also as appreciated by those of skill in the art, halo or halogen as used herein are intended to include chloro, fluoro, bromo and iodo.

As used herein, "alkyl" is intended to mean linear, branched and cyclic structures having no carbon-to-carbon double or triple bonds. Thus $C_{1-6}$alkyl is defined to identify the group as having 1, 2, 3, 4, 5 or 6 carbons in a linear or branched arrangement, such that $C_{1-6}$alkyl specifically includes, but is not limited to, methyl, ethyl, n-propyl, iso-propyl, n-butyl, iso-butyl, tert-butyl, pentyl and hexyl. "Cycloalkyl" is an alkyl, part or all of which forms a ring of three or more atoms. $C_0$ or $C_0$alkyl is defined to identify the presence of a direct covalent bond.

The term "alkenyl" means linear or branched structures and combinations thereof, of the indicated number of carbon atoms, having at least one carbon-to-carbon double bond, wherein hydrogen may be replaced by an additional carbon-to-carbon double bond. $C_{2-6}$alkenyl, for example, includes ethenyl, propenyl, 1-methylethenyl, butenyl and the like.

The term "alkynyl" means linear or branched structures and combinations thereof, of the indicated number of carbon atoms, having at least one carbon-to-carbon triple bond. Thus $C_{2-6}$alkynyl is defined to identify the group as having 2, 3, 4, 5 or 6 carbons in a linear or branched arrangement, such that $C_{2-6}$alkynyl specifically includes 2-hexynyl and 2-pentynyl.

As used herein, "aryl" is intended to mean any stable monocyclic or bicyclic carbon ring of up to 7 members in each ring, wherein at least one ring is aromatic. Examples of such aryl elements include phenyl, napthyl, tetrahydronaphthyl, indanyl, or biphenyl.

The term "heterocycle" or "heterocyclic", as used herein except where noted, represents a stable 5- to 7-membered monocyclic- or stable 8- to 11-membered bicyclic heterocyclic ring system which is either saturated or unsaturated, and which consists of carbon atoms and from one to six heteroatoms selected from the group consisting of N, O, S, P and Si, and wherein the nitrogen, sulfur and phosphorus heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heterocyclic groups include, but are not limited to, azetidine, chroman, dihydrofuran, dihydropyran, dioxane, dioxolane, hexahydroazepine, imidazolidine, imidazolidinone, imidazoline, imidazolinone, indoline, isochroman, isoindoline, isothiazoline, isothiazolidine, isoxazoline, isoxazolidine, morpholine, morpholinone, oxazoline, oxazolidine, oxazolidinone, oxetane, 2-oxohexahydroazepin, 2-oxopiperazine, 2-oxopiperidine, 2-oxopyrrolidine, piperazine, piperidine, pyran, pyrazolidine, pyrazoline, pyrrolidine, pyrroline, quinuclidine, tetrahydrofuran, tetrahydropyran, thiamorpholine, thiazoline, thiazolidine, thiomorpholine and N-oxides thereof.

The term "heteroaryl", as used herein except where noted, represents a stable 5- to 7-membered monocyclic- or stable 9- to 10-membered fused bicyclic heterocyclic ring system which contains an aromatic ring, any ring of which may be saturated, such as piperidinyl, partially saturated, or unsaturated, such as pyridinyl, and which consists of carbon atoms and from one to six heteroatoms selected from the group consisting of N, O, S, P and Si, and wherein the nitrogen, sulfur and phosphorus heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heteroaryl groups include, but are not limited to, benzimidazole, benzisothiazole, benzisoxazole, benzofuran, benzothiazole, benzothiophene, benzotriazole, benzoxazole, carboline, cinnoline, furan, furazan, imidazole, indazole, indole, indolizine, isoquinoline, isothiazole, isoxazole, naphthyridine, oxadiazole, oxazole, phthalazine, pteridine, purine, pyran, pyrazine, pyrazole, pyridazine, pyridine, pyrimidine, pyrrole, quinazoline, quinoline, quinoxaline, tetrazole, thiadiazole, thiazole, thiophene, triazine, triazole, and N-oxides thereof.

The term "alkoxy," as in $C_1$-$C_6$ alkoxy, is intended to refer to include alkoxy groups of from 1 to 6 carbon atoms of a straight, branched and cyclic configuration. Examples include methoxy, ethoxy, propoxy, isopropoxy, cyclopropyloxy, cyclohexyloxy and the like.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. In one aspect of the invention the salts are citric, hydrobromic, hydrochloric, maleic, phosphoric, sulfuric, fumaric, and tartaric acids. It will be understood that, as used herein, references to the compounds of Formula I are meant to also include the pharmaceutically acceptable salts.

Exemplifying the invention is the use of the compounds disclosed in the Examples and herein. Specific compounds within the present invention include a compound which selected from the group consisting of the compounds disclosed in the following Examples and pharmaceutically acceptable salts thereof and individual diastereomers thereof.

The subject compounds are useful in a method of antagonism of CGRP receptors in a patient such as a mammal in need of such antagonism comprising the administration of an effective amount of the compound. The present invention is directed to the use of the compounds disclosed herein as antagonists of CGRP receptors. In addition to primates, especially humans, a variety of other mammals can be treated according to the method of the present invention.

Another embodiment of the present invention is directed to a method for the treatment, control, amelioration, or reduction of risk of a disease or disorder in which the CGRP receptor is involved in a patient that comprises administering to the patient a therapeutically effective amount of a compound that is an antagonist of CGRP receptors.

The present invention is further directed to a method for the manufacture of a medicament for antagonism of CGRP receptors activity in humans and animals comprising combining a compound of the present invention with a pharmaceutical carrier or diluent.

The subject treated in the present methods is generally a mammal, for example a human being, male or female, in whom antagonism of CGRP receptor activity is desired. The term "therapeutically effective amount" means the amount of the subject compound that will elicit the biological or medical response of a tissue, system, animal or human that is being sought by the researcher, veterinarian, medical doctor or other clinician. As used herein, the term "treatment" refers both to the treatment and to the prevention or prophylactic therapy of the mentioned conditions, particularly in a patient who is predisposed to such disease or disorder.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The present invention includes within its scope prodrugs of the compounds of this invention. In general, such prodrugs will be functional derivatives of the compounds of this invention which are readily convertible in vivo into the required compound. Thus, in the methods of treatment of the present invention, the terms "administration of" or "administering a" compound shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985. Metabolites of these compounds include active species produced upon introduction of compounds of this invention into the biological milieu.

The utility of the compounds in accordance with the present invention as antagonists of CGRP receptor activity may be demonstrated by methodology known in the art. Inhibition of the binding of $^{125}$I-CGRP to receptors and functional antagonism of CGRP receptors were determined as follows:

NATIVE RECEPTOR BINDING ASSAY: The binding of $^{125}$I-CGRP to receptors in SK-N-MC cell membranes was carried out essentially as described (Edvinsson et al. (2001) *Eur. J. Pharmacol.* 415, 39-44). Briefly, membranes (25 µg) were incubated in 1 mL of binding buffer [10 mM HEPES, pH 7.4, 5 mM $MgCl_2$ and 0.2% bovine serum albumin (BSA)] containing 10 pM $^{125}$I-CGRP and antagonist. After incubation at room temperature for 3 h, the assay was terminated by filtration through GFB glass fibre filter plates (PerkinElmer) that had been blocked with 0.5% polyethyleneimine for 3 h.

The filters were washed three times with ice-cold assay buffer (10 mM HEPES, pH 7.4 and 5 mM $MgCl_2$), then the plates were air dried. Scintillation fluid (50 µL) was added and the radioactivity was counted on a Topcount (Packard Instrument). Data analysis was carried out by using Prism and the $K_i$ was determined by using the Cheng-Prusoff equation (Cheng & Prusoff (1973) *Biochem. Pharmacol.* 22, 3099-3108).

RECOMBINANT RECEPTOR: Human CL receptor (Genbank accession number L76380) was subcloned into the expression vector pIREShyg2 (BD Biosciences Clontech) as a 5'NheI and 3' PmeI fragment. Human RAMP1 (Genbank accession number AJ001014) was subcloned into the expression vector pIRESpuro2 (BD Biosciences Clontech) as a 5'NheI and 3'NotI fragment. HEK 293 cells (human embryonic kidney cells; ATCC #CRL-1573) were cultured in DMEM with 4.5 g/L glucose, 1 mM sodium pyruvate and 2 mM glutamine supplemented with 10% fetal bovine serum (FBS), 100 units/mL penicillin and 100 µg/mL streptomycin, and maintained at 37° C. and 95% humidity. Cells were subcultured by treatment with 0.25% trypsin with 0.1% EDTA in HBSS. Stable cell line generation was accomplished by co-transfecting 10 µg of DNA with 30 µg Lipofectamine 2000 (Invitrogen) in 75 $cm^2$ flasks. CL receptor and RAMP1 expression constructs were co-transfected in equal amounts. Twenty-four hours after transfection the cells were diluted and selective medium (growth medium+300 µg/mL hygromycin and 1 µg/mL puromycin) was added the following day. A clonal cell line was generated by single cell deposition utilizing a FACS Vantage SE (Becton Dickinson). Growth medium was adjusted to 150 µg/mL hygromycin and 0.5 µg/mL puromycin for cell propagation.

RECOMBINANT RECEPTOR BINDING ASSAY: Cells expressing recombinant human CL receptor/RAMP1 were washed with PBS and harvested in harvest buffer containing 50 mM HEPES, 1 mM EDTA and Complete protease inhibitors (Roche). The cell suspension was disrupted with a laboratory homogenizer and centrifuged at 48,000 g to isolate membranes. The pellets were resuspended in harvest buffer plus 250 mM sucrose and stored at -70° C. For binding assays, 20 µg of membranes were incubated in 1 ml binding buffer (10 mM HEPES, pH 7.4, 5 mM $MgCl_2$, and 0.2% BSA) for 3 hours at room temperature containing 10 µM $^{125}$I-hCGRP (GE Healthcare) and antagonist. The assay was terminated by filtration through 96-well GFB glass fiber filter plates (PerkinElmer) that had been blocked with 0.05% polyethyleneimine. The filters were washed 3 times with ice-cold assay buffer (10 mM HEPES, pH 7.4 and 5 mM $MgCl_2$). Scintillation fluid was added and the plates were counted on a Topcount (Packard). Non-specific binding was determined and the data analysis was carried out with the apparent dissociation constant ($K_i$) determined by using a non-linear least squares fitting the bound CPM data to the equation below:

$$Y_{obsd} = \frac{Y_{min} + (Y_{max} - Y_{min})(100 - \% I_{max}/100) + (Y_{max} - Y_{min})(\% I_{max} - \% I_{min}/100)}{1 + ([Drug]/K_i(1 + [Radiolabel]/K_d)^{nH}}$$

Where Y is observed CPM bound, $Y_{max}$ is total bound counts, $Y_{min}$ is non specific bound counts, ($Y_{max}-Y_{min}$) is specific bound counts, $\% I_{max}$ is the maximum percent inhibition, % I min is the minimum percent inhibition, radiolabel is the probe, and the $K_d$ is the apparent dissociation constant for the radioligand for the receptor as determined by Hot saturation experiments.

RECOMBINANT RECEPTOR FUNCTIONAL ASSAY: Cells were plated in complete growth medium at 85,000 cells/well in 96-well poly-D-lysine coated plates (Corning) and cultured for ~19 h before assay. Cells were washed with PBS and then incubated with inhibitor for 30 min at 37° C. and 95% humidity in Cellgro Complete Serum-Free/Low-Protein medium (Mediatech, Inc.) with L-glutamine and 1 g/L BSA. Isobutyl-methylxanthine was added to the cells at a concentration of 300 µM and incubated for 30 min at 37° C. Human α-CGRP was added to the cells at a concentration of 0.3 nM and allowed to incubate at 37° C. for 5 min. After α-CGRP stimulation the cells were washed with PBS and processed for cAMP determination utilizing the two-stage assay procedure according to the manufacturer's recommended protocol (cAMP SPA direct screening assay system; RPA 559; GE Healthcare). Dose response curves were plotted and $IC_{50}$ values determined from a 4-parameter logistic fit as defined by the equation $y=((a-d)/(1+(x/c)^b)+d$, where y=response, x=dose, a=max response, d=min response, c=inflection point and b=slope.

In particular, the compounds of the following examples had activity as antagonists of the CGRP receptor in the aforementioned assays, generally with a $K_i$ or $IC_{50}$ value of less than about 50 µM. Such a result is indicative of the intrinsic activity of the compounds in use as antagonists of CGRP receptors.

The ability of the compounds of the present invention to act as CGRP antagonists makes them useful pharmacological agents for disorders that involve CGRP in humans and animals, but particularly in humans.

The compounds of the present invention have utility in treating, preventing, ameliorating, controlling or reducing the risk of one or more of the following conditions or diseases: headache; migraine; cluster headache; chronic tension type headache; pain; chronic pain; neurogenic inflammation and inflammatory pain; neuropathic pain; eye pain; tooth pain; diabetes; non-insulin dependent diabetes mellitus; vascular disorders; inflammation; arthritis; bronchial hyperreactivity, asthma; shock; sepsis; opiate withdrawal syndrome; morphine tolerance; hot flashes in men and women; allergic dermatitis; psoriasis; encephalitis; brain trauma; epilepsy; neurodegenerative diseases; skin diseases; neurogenic cutaneous redness, skin rosaceousness and erythema; inflammatory bowel disease, irritable bowel syndrome, cystitis; and other conditions that may be treated or prevented by antagonism of CGRP receptors. Of particular importance is the acute or prophylactic treatment of headache, including migraine and cluster headache.

The subject compounds are further useful in a method for the prevention, treatment, control, amelioration, or reduction of risk of the diseases, disorders and conditions noted herein.

The subject compounds are further useful in a method for the prevention, treatment, control, amelioration, or reduction of risk of the aforementioned diseases, disorders and conditions in combination with other agents.

The compounds of the present invention may be used in combination with one or more other drugs in the treatment, prevention, control, amelioration, or reduction of risk of diseases or conditions for which compounds of Formula I or the other drugs may have utility, where the combination of the drugs together are safer or more effective than either drug alone. Such other drug(s) may be administered, by a route and in an amount commonly used therefor, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy may also include therapies in which the compound of Formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula I.

For example, the present compounds may be used in conjunction with an anti-migraine agent, such as ergotamine and dihydroergotamine, or other serotonin agonists, especially a 5-HT$_{1B/1D}$ agonist, for example sumatriptan, naratriptan, zolmitriptan, eletriptan, almotriptan, frovatriptan, donitriptan, and rizatriptan, a 5-HT$_{1D}$ agonist such as PNU-142633 and a 5-HT$_{1F}$ agonist such as LY334370; a cyclooxygenase inhibitor, such as a selective cyclooxygenase-2 inhibitor, for example rofecoxib, etoricoxib, celecoxib, valdecoxib or paracoxib; a non-steroidal anti-inflammatory agent or a cytokine-suppressing anti-inflammatory agent, for example with a compound such as ibuprofen, ketoprofen, fenoprofen, naproxen, indomethacin, sulindac, meloxicam, piroxicam, tenoxicam, lornoxicam, ketorolac, etodolac, mefenamic acid, meclofenamic acid, flufenamic acid, tolfenamic acid, diclofenac, oxaprozin, apazone, nimesulide, nabumetone, tenidap, etanercept, tolmetin, phenylbutazone, oxyphenbutazone, diflunisal, salsalate, olsalazine or sulfasalazine and the like; or glucocorticoids. Similarly, the instant compounds may be administered with an analgesic such as aspirin, acetaminophen, phenacetin, fentanyl, sufentanil, methadone, acetyl methadol, buprenorphine or morphine.

Additionally, the present compounds may be used in conjunction with an interleukin inhibitor, such as an interleukin-1 inhibitor; an NK-1 receptor antagonist, for example aprepitant; an NMDA antagonist; an NR2B antagonist; a bradykinin-1 receptor antagonist; an adenosine A1 receptor agonist; a sodium channel blocker, for example lamotrigine; an opiate agonist such as levomethadyl acetate or methadyl acetate; a lipoxygenase inhibitor, such as an inhibitor of 5-lipoxygenase; an alpha receptor antagonist, for example indoramin; an alpha receptor agonist; a vanilloid receptor antagonist; a renin inhibitor; a granzyme B inhibitor; a substance P antagonist; an endothelin antagonist; a norepinephrin precursor; anti-anxiety agents such as diazepam, alprazolam, chlordiazepoxide and chlorazepate; serotonin 5HT$_2$ receptor antagonists; opiod agonists such as codeine, hydrocodone, tramadol, dextropropoxyphene and febtanyl; an mGluR5 agonist, antagonist or potentiator; a GABA A receptor modulator, for example acamprosate calcium; nicotinic antagonists or agonists including nicotine; muscarinic agonists or antagonists; a selective serotonin reuptake inhibitor, for example fluoxetine, paroxetine, sertraline, duloxetine, escitalopram, or citalopram; an antidepressant, for example amitriptyline, nortriptyline, clomipramine, imipramine, venlafaxine, doxepin, protriptyline, desipramine, trimipramine, or imipramine; a leukotriene antagonist, for example montelukast or zafirlukast; an inhibitor of nitric oxide or an inhibitor of the synthesis of nitric oxide.

Also, the present compounds may be used in conjunction with gap junction inhibitors; neuronal calcium channel blockers such as civamide; AMPA/KA antagonists such as LY293558; sigma receptor agonists; and vitamin B2.

Also, the present compounds may be used in conjunction with ergot alkaloids other than ergotamine and dihydroergotamine, for example ergonovine, ergonovine, methylergonovine, metergoline, ergoloid mesylates, dihydroergocornine, dihydroergocristine, dihydroergocryptine, dihydro-α-ergocryptine, dihydro-β-ergocryptine, ergotoxine, ergocornine, ergocristine, ergocryptine, α-ergocryptine, β-ergocryptine, ergosine, ergostane, bromocriptine, or methysergide.

Additionally, the present compounds may be used in conjunction with a beta-adrenergic antagonist such as timolol, propanolol, atenolol, metoprolol or nadolol, and the like; a MAO inhibitor, for example phenelzine; a calcium channel blocker, for example flunarizine, diltiazem, amlodipine, felodipine, nisolipine, isradipine, nimodipine, lomerizine, verapamil, nifedipine, or prochlorperazine; neuroleptics such as olanzapine, droperidol, prochlorperazine, chlorpromazine and quetiapine; an anticonvulsant such as topiramate, zonisamide, tonabersat, carabersat, levetiracetam, lamotrigine, tiagabine, gabapentin, pregabalin or divalproex sodium; an anti-hypertensive such as an angiotensin II antagonist, for example losartan, irbesartin, valsartan, eprosartan, telmisartan, olmesartan, medoxomil, candesartan and candesartan cilexetil, an angiotensin I antagonist, an angiotensin converting enzyme inhibitor such as lisinopril, enalapril, captopril, benazepril, quinapril, perindopril, ramipril and trandolapril; or botulinum toxin type A or B.

The present compounds may be used in conjunction with a potentiator such as caffeine, an H2-antagonist, simethicone, aluminum or magnesium hydroxide; a decongestant such as oxymetazoline, epinephrine, naphazoline, xylometazoline, propylhexedrine, or levo-desoxy-ephedrine; an antitussive such as caramiphen, carbetapentane, or dextromethorphan; a diuretic; a prokinetic agent such as metoclopramide or domperidone; a sedating or non-sedating antihistamine such as acrivastine, azatadine, bromodiphenhydramine, brompheniramine, carbinoxamine, chlorpheniramine, clemastine, dexbrompheniramine, dexchlorpheniramine, diphenhydramine, doxylamine, loratadine, phenindamine, pheniramine, phenyltoloxamine, promethazine, pyrilamine, terfenadine, triprolidine, phenylephrine, phenylpropanolamine, or pseudoephedrine. The present compounds also may be used in conjunction with anti-emetics.

In a particularly preferred embodiment the present compounds are used in conjunction with an anti-migraine agent, such as: ergotamine or dihydroergotamine; a 5-HT$_1$ agonist, especially a 5-HT$_{1B/1D}$ agonist, in particular, sumatriptan, naratriptan, zolmitriptan, eletriptan, almotriptan, frovatriptan, donitriptan, avitriptan and rizatriptan, and other serotonin agonists; and a cyclooxygenase inhibitor, such as a selective cyclooxygenase-2 inhibitor, in particular, rofecoxib, etoricoxib, celecoxib, valdecoxib or paracoxib.

The above combinations include combinations of a compound of the present invention not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the compound of the present invention to the other active ingredient(s) may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, or from about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s), and via the same or different routes of administration.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, solutions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release. Oral tablets may also be formulated for immediate release, such as fast melt tablets or wafers, rapid dissolve tablets or fast dissolve films.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions and the like, containing the compounds of the present invention are employed. Similarly, transdermal patches may also be used for topical administration.

The pharmaceutical composition and method of the present invention may further comprise other therapeutically active compounds as noted herein which are usually applied in the treatment of the above mentioned pathological conditions.

In the treatment, prevention, control, amelioration, or reduction of risk of conditions which require antagonism of CGRP receptor activity an appropriate dosage level will generally be about 0.01 to 500 mg per kg patient body weight per day which can be administered in single or multiple doses. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are may be provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, or may be administered once or twice per day.

When treating, preventing, controlling, ameliorating, or reducing the risk of headache, migraine, cluster headache, or other diseases for which compounds of the present invention are indicated, generally satisfactory results are obtained when the compounds of the present invention are administered at a daily dosage of from about 0.1 milligram to about 100 milligram per kilogram of animal body weight, given as a single daily dose or in divided doses two to six times a day, or in sustained release form. For most large mammals, the total daily dosage is from about 1.0 milligrams to about 1000 milligrams, or from about 1 milligrams to about 50 milligrams. In the case of a 70 kg adult human, the total daily dose will generally be from about 7 milligrams to about 350 milligrams. This dosage regimen may be adjusted to provide the optimal therapeutic response.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Several methods for preparing the compounds of this invention are illustrated in the following Schemes and Examples. Starting materials are made according to procedures known in the art or as illustrated herein.

The compounds of the present invention can be prepared readily according to the following Schemes and specific examples, or modifications thereof, using readily available starting materials, reagents and conventional synthesis procedures. In these reactions, it is also possible to make use of variants which are themselves known to those of ordinary skill in this art but are not mentioned in greater detail. The general procedures for making the compounds claimed in this invention can be readily understood and appreciated by one skilled in the art from viewing the following Schemes.

SCHEME 1

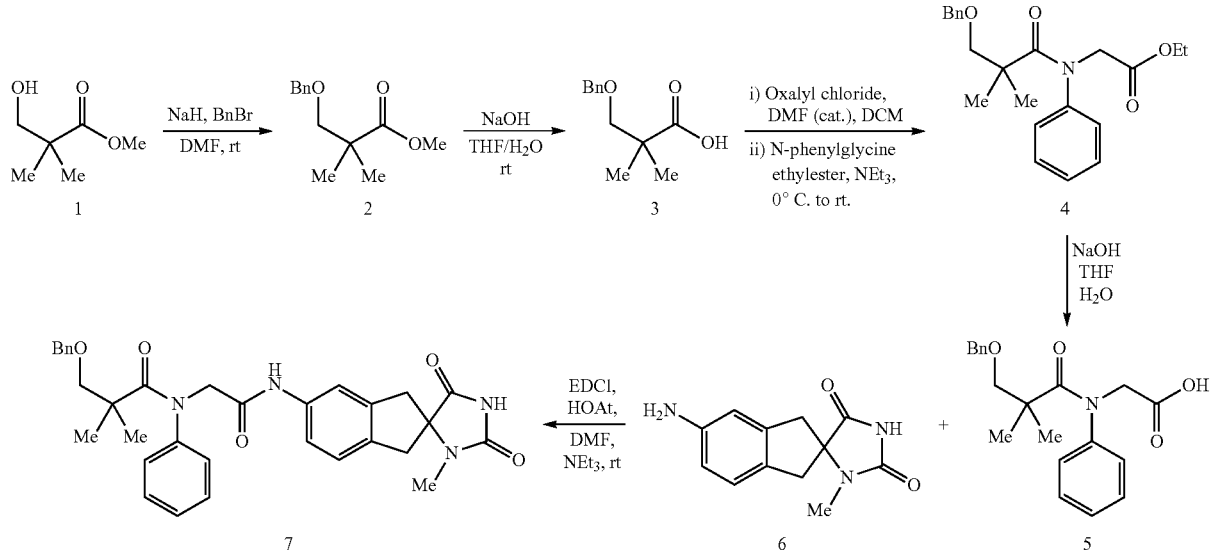

Alcohol 1 can be deprotonated with the strong base sodium hydride, in DMF, to provide the alkoxy anion which smoothly reacts with the electrophilic benzyl bromide to provide ether 2. Subsequent treatment of this ether product, in THF, with aqueous sodium hydroxide gives the acid 3. Acid 3 can be coupled to N-phenylglycine ethylester after the carboxylic has been converted to the corresponding acid chloride using oxalyl chloride and a catalytic amount of DMF, in DCM, yielding ester 4. This ester can be hydrolyzed to the acid 5 using NaOH in a THF/water mixture. Acid 5 can be coupled to the known aniline 6 (Bell, I. M., et al., PCT Int. Appl., WO 2004082605 A2 20040930) employing the standard peptide coupling reagent combination of EDCI, HOAt and triethylamine, in DMF, to provided the claimed compound 7. A variety of carboxylic acids, similar to acid 3, either commercially available, or prepared by a variety of common methods, can similarly be utilized in the above procedure to provide compounds of the present invention. Substituted analogs of glycine esters, if not commercially available, can be prepared by a variety of common methods, one of which is illustrated in scheme 2, for the preparation of N-benzyl glycine analogs of the present invention.

PCT Int. Appl., WO 2004082605 A2 20040930) employing the standard peptide coupling reagent combination of EDCI, HOAt and triethylamine, in DMF, to provided the claimed compound 13. Analogs of amine 8, if not commercially available, can be prepared by a variety of common methods; in the case of benzylic amines containing a chiral benzylic substituent the methods of Ellman and coworkers (*Tetrahedron Lett.*, 1999, 40, 6709-6712) can be utilized.

SCHEME 3

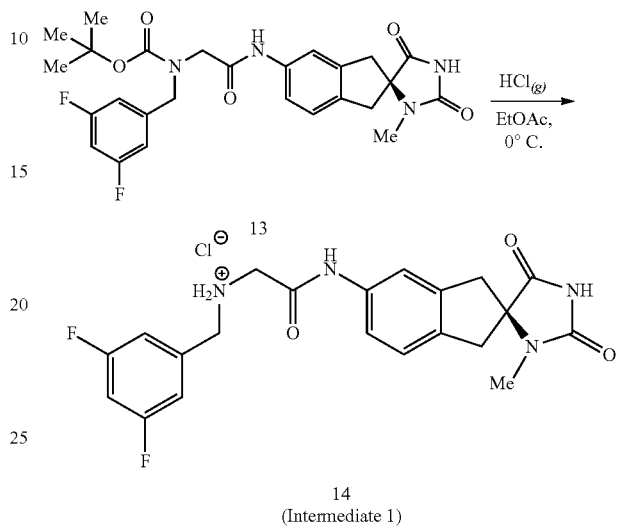

SCHEME 2

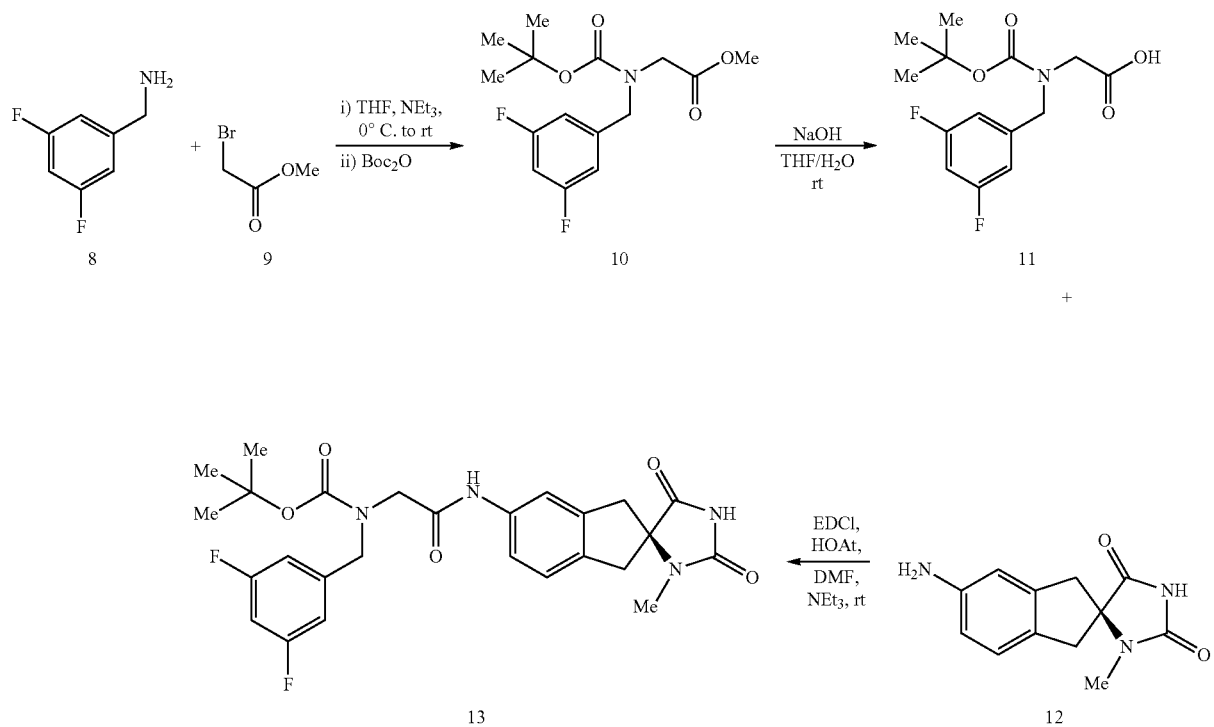

Benzylic amine 8 can be allowed to react with methyl bromoacetate (9) in THF to give primarily the mono-alkylation product, which is subsequently treated, in the same pot, with Boc-anhydride, to provide ester 10. Treatment of this ester with aqueous sodium hydroxide gives the acid 11. Acid 11 can be coupled to the known aniline 12 (Bell, I. M., et al., Scheme 3 illustrates the conversion of the claimed carbamate 13, into the useful intermediate 14. Removal of the tert-butyl carbamate using anhydrous hydrogen chloride in chilled ethyl acetate cleanly provides the hydrochloride salt 14. Alternatively, other strong acids may be employed, such as TFA, to provide analogous salts of 14.

SCHEME 4

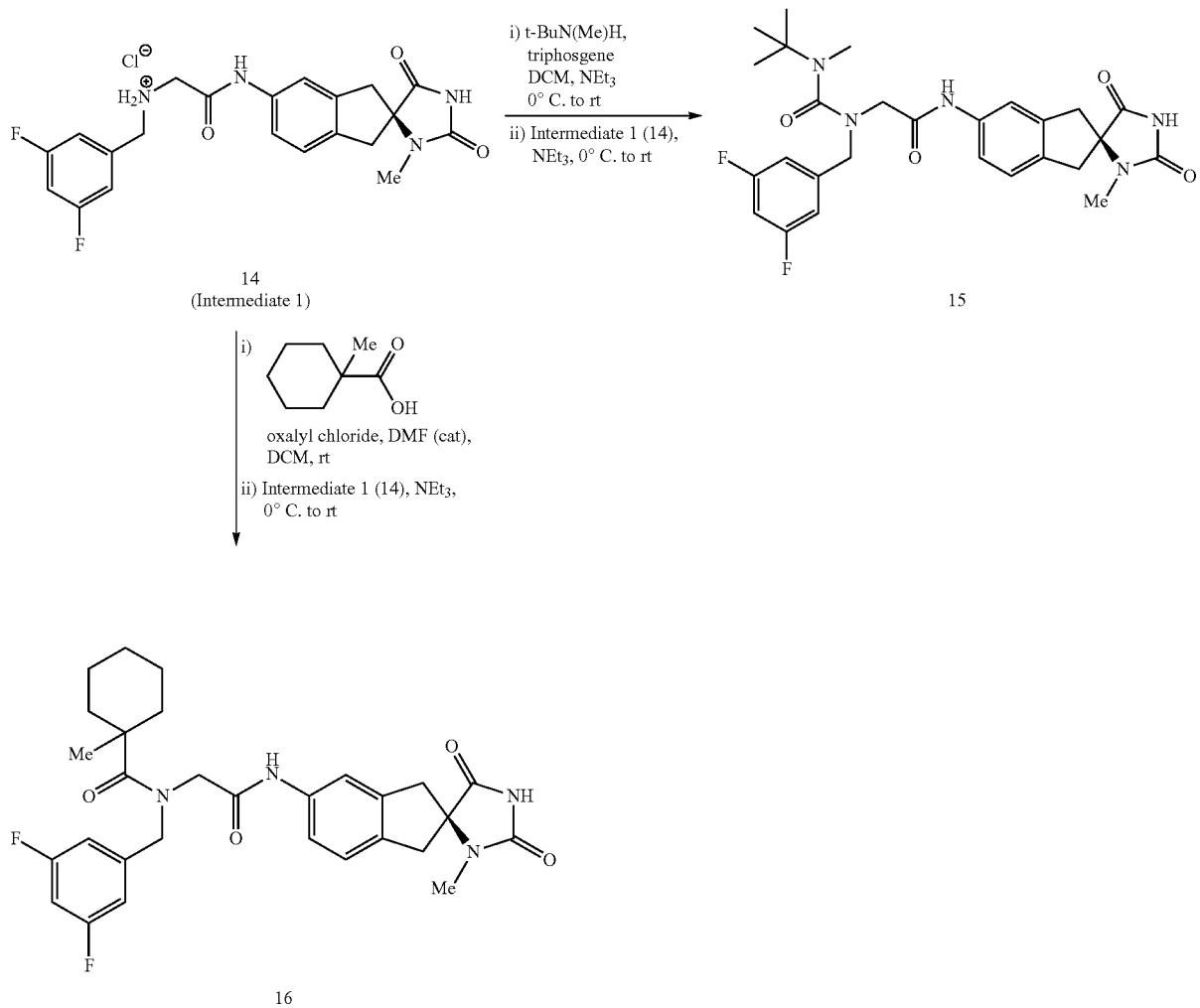

Scheme 4 shows the conversion of compound 14, into additional compounds of the present invention. The reaction between tert-butylmethyl amine and one third an equivalent of triphosgene, in DCM, in the presence of triethylamine, produces the expected carbamoyl chloride which subsequently reacts with 14, in the presence of additional triethylamine, to provide claimed compound 15. Alternatively, acid chlorides, commercially obtained, or prepared in situ from the requisite carboxylic acid, oxalyl chloride and a catalytic amount of DMF, in DCM, can react with compound 14, in the presence of triethylamine to give claimed compound 16. It is understood that alternative methods for amide and urea formation utilizing intermediate 14 may also be employed to provide claimed compounds 15 and 16.

SCHEME 5

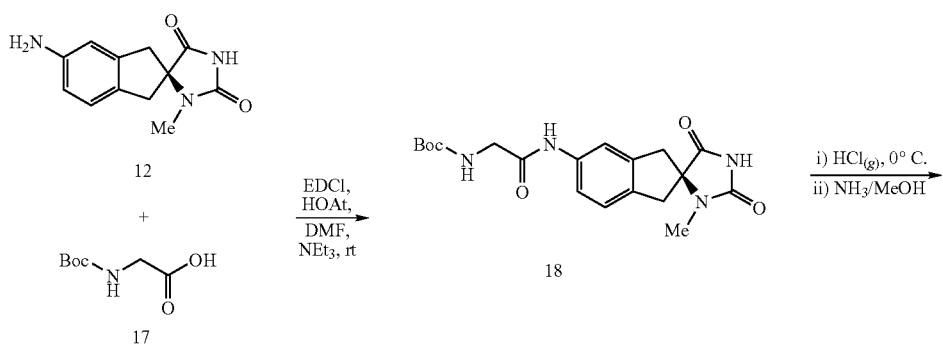

-continued

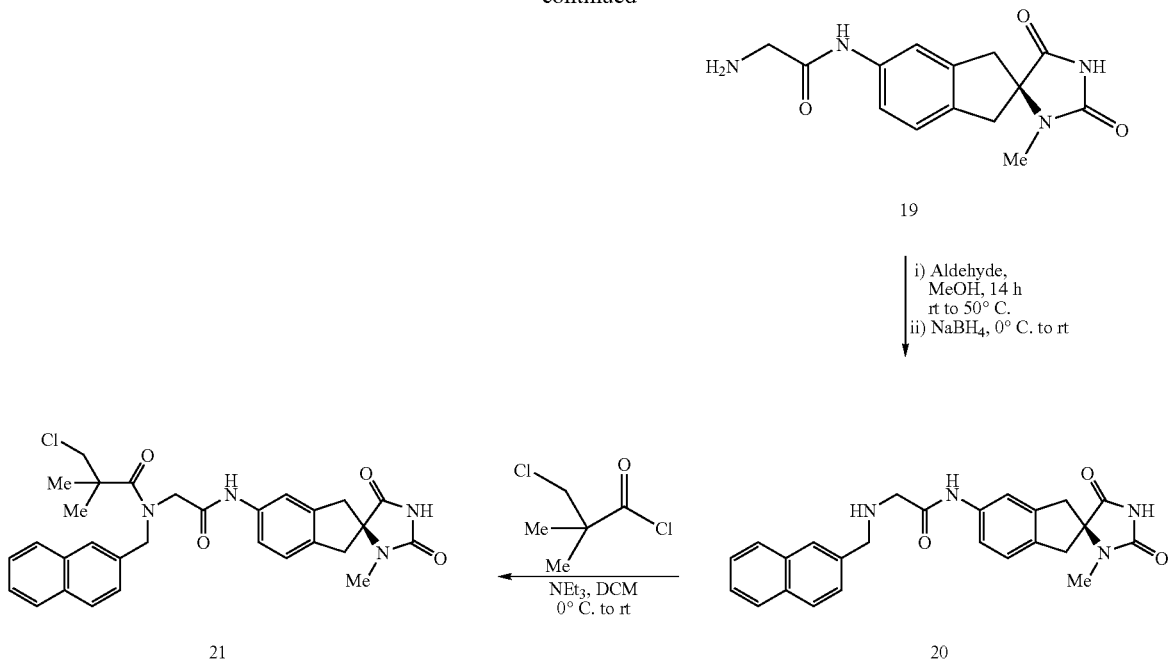

Scheme 5 depicts an additional method by which compounds of the present invention may be prepared. Known compound 12 (Bell, I. M., et al., PCT Int. Appl., WO 2004082605 A2 20040930) can be coupled to the acid 17 employing the standard peptide coupling reagent combination of EDCI, HOAt and triethylamine, in DMF, to provided the protected amine 18. The tert-butyl carbamate of 18 can be removed using anhydrous hydrogen chloride, in methanol, at 0° C. The expected amine hydrochloride can be converted to the free amine 19, using ammonia in methanol, in conjunction with silica gel chromatography. This amine, 19, can then be condensed with various aldehydes to form the imine, by heating the two reagents, in methanol, at 50° C., for 14 hours. Once progress in the imine-forming step has halted, cooling the mixture to 0° C. is followed by the addition of sodium borohydride to quickly give compound 20. The amine 20, which is of similar utility relative to intermediate 14, can react with acid chlorides, such as 3-chloro-2,2-dimethylpropanoyl chloride, to give claimed compound 21.

While scheme 1 specifically depicts the preparation and use of acid 3, it is understood that alternative acids may be obtained and utilized in order to provide various compounds of the present invention. For example, scheme 6 illustrates the synthesis of claimed compounds that are analogous to those in scheme 1 but of a more general structure. Acid 22 (denoting $R^9CO_2H$ and $R^{29}CO_2H$), obtained commercially or prepared by means know to those skilled in the art, may be converted, in situ, to the acid chloride using appropriate reagent, such as oxalyl chloride and a catalytic amount of DMF, in an aprotic solvent, such as DCM. Alternatively, these acid chlorides may be obtained commercially when available. Said acid chlorides may then couple to amines of general structure 23, facilitated by the addition of a base, such as triethylamine, at a temperature affording a desirable rate of reaction, to give ester 24. It is to be understood that throughout these general schemes (6-9) and consistent with the claims of the present invention, $R^9$ and $R^{11}$ constitute an associated pair of substituents, as do $R^{29}$ and $R^{21}$ when they appear in the same general structure (e.g. 24). The ester 24, although not limited to methyl ester, may then be hydrolyzed by an appropriate base, such as NaOH, in a solvent mixture, such as water/THF, to provide acid 25. Acid 25 may then be coupled to aniline 26 using a variety of peptide coupling reagent combinations, such as EDCI and HOAt, in the presence of an appropriate base, such as triethylamine, in an appropriate solvent, such as DMF, to yield compound 27.

SCHEME 6

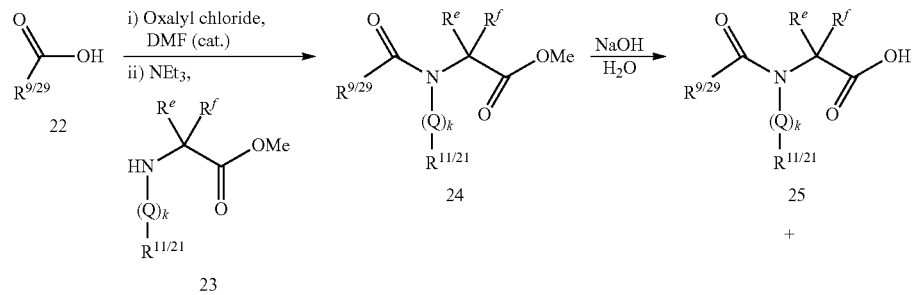

-continued

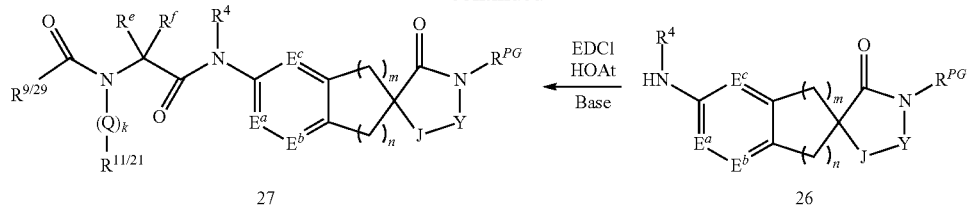

27 → 26 (EDCl, HOAt, Base)

While the methodology shown in scheme 2 is exemplified using amine 8 and ester 9, it is understood that it may be applied to a variety of reagents, such as those described herein, in order to provide compounds of the present invention. For example, scheme 7 illustrates the synthesis of analogous carbamates to that in scheme 2 but of a more general structure. Amine 28 can displace the halide (not limited to bromide) of ester 29, in a solvent, such as THF, in the presence of a base, such as triethylamine, at an appropriate temperature, to give a secondary amine which can be acylated, in the same reaction mixture, with an appropriate carbamate-forming reagent, such as Boc-anhydride, to give ester 30. Alternatively, the secondary amine could be isolated, purified and then subsequently acylated to arrive at 30. The ester 30, although not limited to methyl ester, may then be hydrolyzed by an appropriate base, such as NaOH, in a solvent mixture, such as water/THF, to provide acid 31. Acid 31 may then be coupled to aniline 26 using a variety of peptide coupling reagent combinations, such as EDCI and HOAt, in the presence of an appropriate base, such as triethylamine, in an appropriate solvent, such as DMF, to yield compound 32. It is understood by those skilled in the art that in some cases alternative reagents or conditions may be used to effect the transformations in scheme 7. For instance, racemic reaction sequences may be utilized, followed by chiral separations at appropriate steps to provide compounds of the present invention. The exact choice of reagents, solvents, temperatures, and other reaction conditions, depends upon the nature of the intended product. In some cases, additional chemical steps may be required to obtain the compounds of interest, or various protecting group strategies may be employed.

SCHEME 7

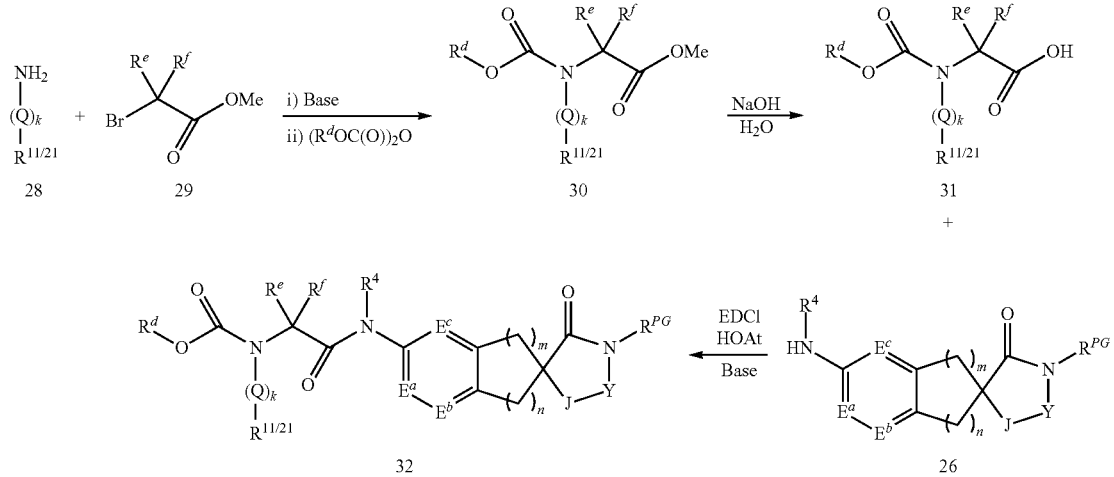

Scheme 3, shows the conversion of claimed compound 13 into the useful intermediate 14; while Scheme 8 depicts this, and additional transformations, of a more general structure. The Boc-protected amine 33, can be deprotected using a strong acid, such as HCl or TFA, in an appropriate solvent, such as EtOAc, generally at reduced temperatures, to cleanly provide the amine hydrochloride salt 34. Compound 34 can then be transformed into urea 35, by reacting with isocyanates/carbamoyl chlorides commercially obtained or prepared in situ from amine, base and triphosgene, facilitated by the addition of an appropriate base such as triethylamine, in an appropriate such as DCM or DMF. Amine 34 can alternatively be coupled to acid 22, through its corresponding acid chlorides, as previously described, or through a variety of peptide coupling reagent combinations, as previously described, to give claimed compounds 27. Although not illustrated, compound 34, is also useful in the preparation of claimed sulfonamides by using reagents such as sulfonyl chlorides, along with a base, such as triethylamine, in an appropriate solvent, such as DCM.

SCHEME 8

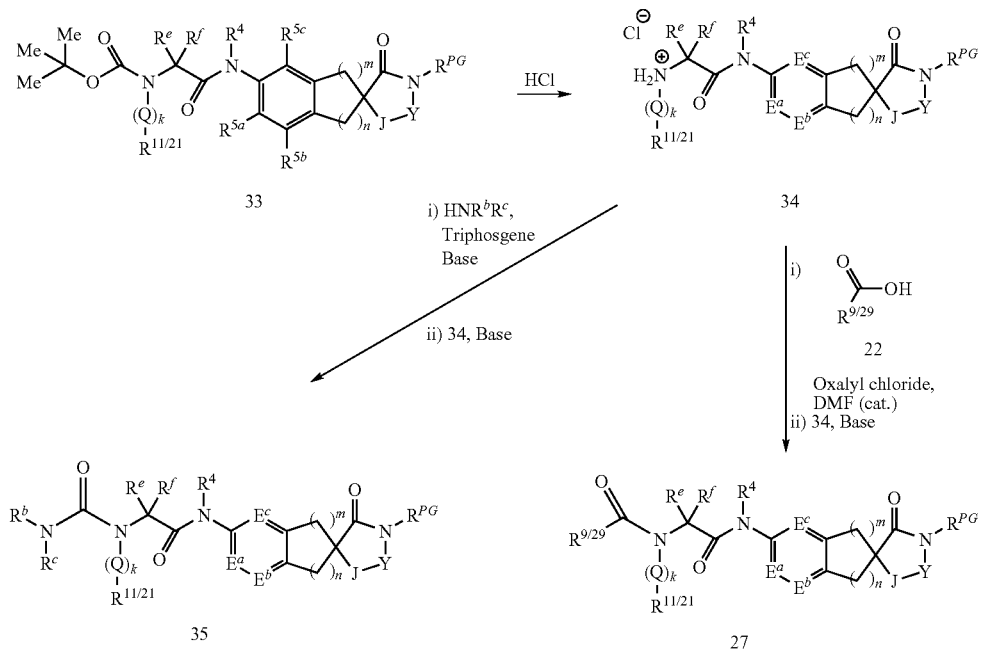

It is understood by those skilled in the art that in some cases alternative reagents or conditions may be used to effect the transformations in scheme 8. For instance, racemic reaction sequences may be utilized, followed by chiral separations at appropriate steps to provide compounds of the present invention. The exact choice of reagents, solvents, temperatures, and other reaction conditions, depends upon the nature of the intended product. In some cases, additional chemical steps may be required to obtain the compounds of interest, or various protecting group strategies may be employed.

Scheme 9, similar to scheme 6, illustrates an alternative method for the preparation of compounds of the present invention, using general structures. Boc-protected, substituted (or unsubstituted) glycine acid 36, can be coupled to aniline 26 using a variety of peptide coupling reagent combinations, such as EDCI and HOAt, in the presence of an appropriate base, such as triethylamine, in an appropriate solvent, such as DMF, to yield compound 37. The carbamate of 37, can be removed using a strong acid, such as HCl, in an appropriate solvent, such as MeOH, to give the corresponding amine hydrochloride, from which can be formed the free-base primary amine 38, using ammonia in MeOH, in conjunction with silica gel chromatography, or alternative free-base-forming conditions. Primary amine 38 can then be allowed to condense with aldehydes or ketones, in an appropriate solvent, like MeOH, at an elevated temperature, when necessary, to give an imine which is then reduced by the introduction of an appropriate reducing reagent, like NaBH$_4$, to give amine 39. Amine 39, can then be allowed to react with acid chloride 40, with the addition of a base, like triethylamine, in an aprotic, like DCM to give compound 27. Additionally, 39 can be utilized in the production of claimed carbamates, ureas, and sulfonamides of the present invention using standard procedures known to those skilled in the art.

SCHEME 9

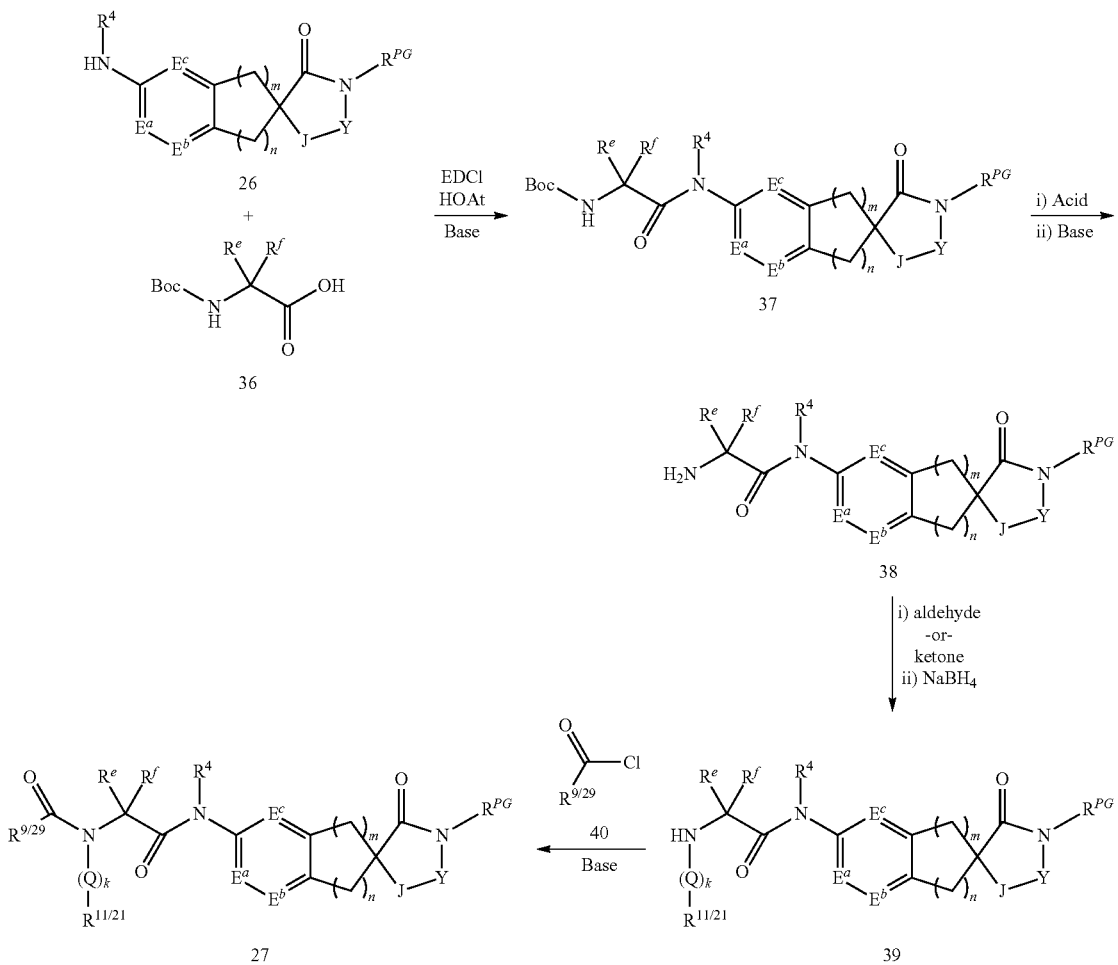

It is understood by those skilled in the art that in some cases alternative reagents or conditions may be used to effect the transformations in the schemes outlined above. For instance, racemic reaction sequences may be utilized, followed by chiral separations at appropriate steps to provide compounds of the present invention. The exact choice of reagents, solvents, temperatures, and other reaction conditions, depends upon the nature of the intended product. In some cases, additional chemical steps may be required to obtain the compounds of interest, or various protecting group strategies may be employed.

In some cases the final product may be further modified, for example, by manipulation of substituents. These manipulations may include, but are not limited to, reduction, oxidation, alkylation, acylation, and hydrolysis reactions which are commonly known to those skilled in the art.

In some cases the order of carrying out the foregoing reaction schemes may be varied to facilitate the reaction or to avoid unwanted reaction products. Additionally, various protecting group strategies may be employed to facilitate the reaction or to avoid unwanted reaction products. The following examples are provided so that the invention might be more fully understood. These examples are illustrative only and should not be construed as limiting the invention in any way.

Example 1

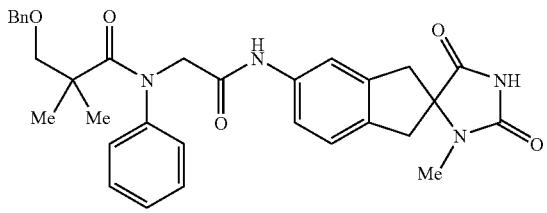 [SMILES: CN1C(=O)NC(=O)C12Cc1ccc(NC(=O)CN(C(=O)C(C)(C)COCc3ccccc3)c3ccccc3)cc1C2]

(±)-3-(benzyloxy)-2,2-dimethyl-N-{2-[(3-methyl-2,5-dioxo-1',3'-dihydrospiro[imidazolidine-4,2'-inden]-5'-yl)amino]-2-oxoethyl}-N-phenylpropanamide Step A. methyl 3-(benzyloxy)-2,2-dimethylpropanoate To a stirred solution of methyl 3-hydroxy-2,2-dimethylpropanoate (600. mg, 4.54 mmol) in DMF (9.0 mL), cooled to 0° C., was added NaH (120. mg, 4.99 mmol). After warming to ambient temperature for 30 minutes, the reaction was cooled to 0° C., prior to the introduction of benzyl bromide (854 mg, 4.99 mmol). After warming to ambient temperature, the reaction was heated to 50° C. for 4 hours, before being allowed to return to ambient temperature. The bulk of the DMF was removed in vacuo, and the residue was diluted with water and EtOAc. The organic layer was washed several times with water and then once with saturated brine. The organics were then dried over sodium sulfate, filtered and concentrated in vacuo, to yield a residue which was applied to a silica gel column for purification, eluting with 100% DCM. The resulting impure material was applied again to silica gel and eluted with a gradient of $CH_2Cl_2$:hexanes—85:15 to 100:0. Clean product-containing fractions were pooled and concentrated in vacuo to give the title compound. MS: m/z=223 (M+1).

Step B. 3-(benzyloxy)-2,2-dimethylpropanoic acid

To a stirred solution of methyl 3-(benzyloxy)-2,2-dimethylpropanoate prepared according to Step A (952 mg, 4.28 mmol), in THF (11 mL) was added aqueous 1M NaOH (5.14 mL, 5.14 mmol). Little to no progress was seen at ambient temperature. Additional NaOH (~7 mL, ~7 mmol) was then added and the temperature was raised to 65° C., for 20 hours. After cooling to ambient temperature, the bulk of the THF was removed in vacuo. Aqueous 3M HCl (~5 mL, ~15 mmol) was then slowly added, resulting in the formation of a precipitate. This mixture was filtered through filter paper, and washed with a minimal amount of water. After placing under a strong vacuum for a few hours, the title compound was obtained. MS: m/z=231 (M+23 (Na$^+$)).

Step C. ethyl[[3-(benzyloxy)-2,2-dimethylpropanoyl](phenyl)amino]acetate

To a stirred solution of 3-(benzyloxy)-2,2-dimethylpropanoic acid from Step B (415 mg, 1.99 mmol) in DCM (20 mL) was added one drop of DMF (cat.) followed by the drop wise addition of oxalyl chloride (329 mg, 2.59 mmol) over 10 minutes, while at ambient temperature. After the evolution of gas has ceased, the reaction was cooled to 0° C., prior to the introduction of ethyl anilinoacetate (429 mg, 2.39 mmol) and triethylamine (302 mg, 2.99 mmol). After 2 hours at 0° C., the reaction was allowed to warm to ambient temperature and then stir for an additional 1 hour. The reaction mixture was applied directly to a silica gel column for purification, eluting with a gradient of $CH_2Cl_2$:MeOH—99.5:0.5 to 98:2. Product containing fractions were pooled and concentrated in vacuo to give the title compound. MS: m/z=370 (M+1).

Step D. [[3-(benzyloxy)-2,2-dimethylpropanoyl](phenyl)amino]acetic acid

To a stirred solution of ethyl[[3-(benzyloxy)-2,2-dimethylpropanoyl](phenyl)amino]acetate from Step C (530. mg, 1.44 mmol) in THF (10 mL), at ambient temperature, was added aqueous 1M NaOH (2.40 mL, 2.40 mmol). The stirred reaction was then heated to 50° C. for 19 hours, before being allowed to cool to ambient temperature. The bulk of the THF was then removed in vacuo, and aqueous 1M HCl (2.4 mL, 2.4 mmol) was then added resulting in an oily biphasic mixture. The mixture was extracted with ethyl acetate (twice) and the combined organics were washed with water and lastly saturated brine. The organics were then dried over sodium sulfate, filtered and concentrated in vacuo to yield the title compound which was used without further purification. MS: m/z=342 (M+1).

Step E. (±)-3-(benzyloxy)-2,2-dimethyl-N-{2-[(3-methyl-2,5-dioxo-1',3'-dihydrospiro[imidazolidine-4, 2'-inden]-5'-yl)amino]-2-oxoethyl}-N-phenylpropanamide To a stirred solution of [[3-(benzyloxy)-2,2-dimethylpropanoyl](phenyl)amino]acetic acid from Step D (100. mg, 0.293 mmol), (±)-5'-amino-3-methyl-1',3'-dihydro-2H,5H-spiro[imidazolidine-4,2'-indene]-2,5-dione (75.0 mg, 0.322 mmol), and HOAt (16.0 mg, 0.117 mmol) in DMF (3 mL) was added triethylamine (71.0 mg, 0.703 mmol) and EDCI (79.0 mg, 0.410 mmol). The reaction mixture was stirred at ambient temperature for 16 hours, after which time the reaction was judged to be complete by LCMS analysis. The mixture was diluted with EtOAc (60 mL) and washed three times with 30 mL of water (containing a dash of 1M HCl), once with half-saturated brine and once with saturated brine. The organics were then dried over sodium sulfate, filtered and concentrated in vacuo to give a residue which was applied to a silica gel column for purification, eluting with a gradient of $CH_2Cl_2$:MeOH—99:1 to 92:8. Clean product-containing fractions were pooled and concentrated in vacuo to give the title compound as a white solid. MS: m/z=577 (M+23 (Na$^+$)). HRMS: m/z=555.2597; calculated m/z=555.2602 for $C_{32}H_{35}N_4O_5$.

Example 2

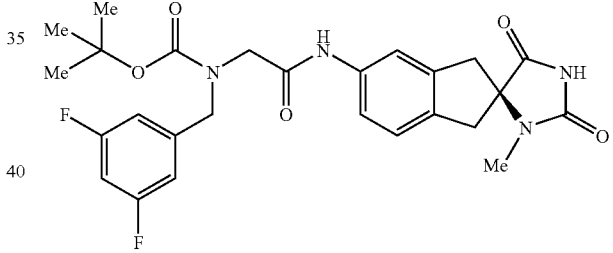

tert-butyl (3,5-difluorobenzyl)(2-{[(4S)-3-methyl-2, 5-dioxo-1',3'-dihydrospiro[imidazolidine-4,2'-inden]-5'-yl]amino}-2-oxoethyl)carbamate Step A. methyl[(tert-butoxycarbonyl)(3,5-difluorobenzyl)amino]acetate To a stirred solution of 1-(3,5-difluorophenyl)methanamine (1.00 g, 6.99 mmol) and triethylamine (848 mg, 8.38 mmol) in THF (70 mL), cooled to 0° C., was added methyl bromoacetate (1.07 g, 6.99 mmol). The reaction was allowed to warm to ambient temperature overnight. The next day, the reaction was cooled to 0° C. prior to the introduction of additional methyl bromoacetate (1.07 g, 6.99 mmol) and triethyamine (848 mg, 8.38 mmol). The reaction was allowed to warm to ambient temperature overnight. The next day, the reaction was cooled to 0° C. prior to the introduction of boc-anhydride (1.83 g, 8.38 mmol) and triethylamine (848 mg, 8.38 mmol). The reaction was allowed to warm to ambient temperature overnight. The next day, the reaction mixture was diluted with EtOAc and water. The organics were washed with brine, dried over sodium sulfate, filtered and concentrated in vacuo to give a residue which was applied to a silica gel column for purification, eluting with EtOAc:hexanes—5:95 to 30:70. Product containing fractions were pooled and concentrated in vacuo to give the title compound. MS: m/z=216 (M−99(−Boc+2H)).

Step B. [(tert-butoxycarbonyl)(3,5-difluorobenzyl)amino]acetic acid

To a stirred solution of methyl[(tert-butoxycarbonyl)(3,5-difluorobenzyl)amino]acetate from Step B (1.89 g, 5.99 mmol) in THF (60 mL) was added potassium trimethylsilanolate (1.00 g, 7.79 mmol). The reaction mixture was allowed to stir at ambient temperature for 72 hours. The bulk of the THF was then removed in vacuo, and the residue was diluted with water. The aqueous layer was extracted three times with diethyl ether, discarding ether extracts. The aqueous layer was placed under reduce pressure to remove residual ether and then was brought to an acidic pH with aqueous 1 M HCl to obtain an oil. The oil was dissolved in EtOAc and the combined organics were dried over sodium sulfate, filtered and concentrated in vacuo to yield the title compound. MS: m/z=319 (M+18 ($NH_4^+$)).

Step C. tert-butyl (3,5-difluorobenzyl)(2-{[(4S)-3-methyl-2,5-dioxo-1',3'-dihydrospiro[imidazolidine-4,2'-inden]-5'-yl]amino}-2-oxoethyl)carbamate To a stirred solution of [(tert-butoxycarbonyl)(3,5-difluorobenzyl)amino]acetic acid from Step B (1.13 g, 3.75 mmol) in DMF (7.5 mL) was added (4S)-5'-amino-3-methyl-1',3'-dihydro-2H,5H-spiro[imidazolidine-4,2'-indene]-2,5-dione (867 mg, 3.75 mmol), EDCI (934 mg, 4.87 mmol), HOAt (510. mg, 3.75 mmol) and lastly triethylamine (493 mg, 4.87 mmol). This reaction was found to be complete after 3 hours by LCMS analysis. The reaction mixture was partitioned between 0.5 M HCl (100 mL) and EtOAc (100 mL) The organics were washed with water, then brine, dried over sodium sulfate, filtered and concentrated in vacuo to give a residue which was applied to a silica gel column for purification, eluting with DCM:MeOH—99:1 to 95:5. Product containing fractions were pooled and concentrated in vacuo to give the title compound. MS: m/z=515 (M+1). HRMS: m/z=515.2108; calculated m/z=515.2101 for $C_{26}H_{29}N_4O_5F_2$.

INTERMEDIATE 1

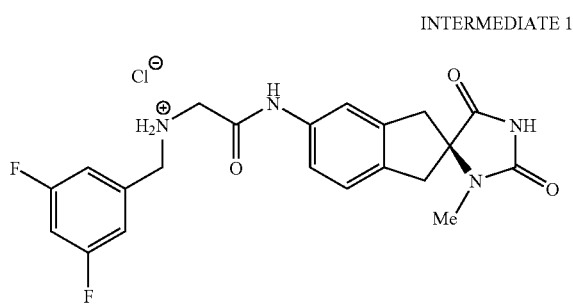 [SMILES: CN1C(=O)NC(=O)[C@@]12Cc1ccc(NC(=O)C[NH2+]Cc3cc(F)cc(F)c3)cc1C2 ; [Cl-]]

N-(3,5-difluorobenzyl)-2-{[(4S)-3-methyl-2,5-dioxo-1',3'-dihydrospiro[imidazolidine-4,2'-inden]-5'-yl]amino}-2-oxoethanaminium chloride To a solution of tent-butyl (3,5-difluorobenzyl)(2-{[(4S)-3-methyl-2,5-dioxo-1',3'-dihydrospiro[imidazolidine-4,2'-inden]-5'-yl]amino}-2-oxoethyl)carbamate (1.80 g, 3.50 mmol, Example 2) in EtOAc (35 mL), cooled to 0° C. was bubbled in anhydrous hydrogen chloride for a period of about 5 minutes. After standing for 30 minutes, at 0° C., the solvent was removed in vacuo to yield the title compound as a white solid. This solid was paced under high vacuum for 18 hours at ambient temperature, to give the title compound. MS: m/z=415 (M+1).

Example 3

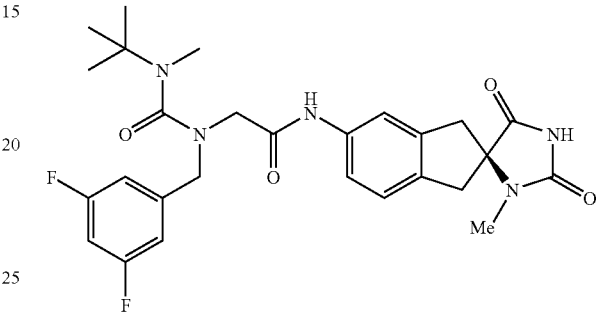

2-[{[tert-butyl(methyl)amino]carbonyl}(3,5-difluorobenzyl)amino]-N-[(4S)-3-methyl-2,5-dioxo-1',3'-dihydrospiro[imidazolidine-4,2'-inden]-5'-yl]acetamide To a solution of N,2-dimethylpropan-2-amine (16.0 mg, 0.189 mmol) and triethylamine (19.1 mg, 0.189 mmol) in DCM (1.5 mL), cooled to 0° C., was added triphosgene (19.0 mg, 0.0640 mmol), followed by additional triethylamine (28.7 mg, 0.284 mmol). After 10 minutes of stirring at 0° C., the ice bath was removed and the reaction was allowed to warm to ambient temperature. After 45 minutes at ambient temperature the reaction was cooled to 0° C. prior to the introduction of a chilled (0° C.), DCM (1 mL) solution of triethylamine (19.1 mg, 0.189 mmol) and N-(3,5-difluorobenzyl)-2-{[(4S)-3-methyl-2,5-dioxo-1',3'-dihydrospiro[imidazolidine-4,2'-inden]-5'-yl]amino}-2-oxoethanaminium chloride (85.0 mg, 0.189 mmol, Intermediate 1). The ice bath was allowed to slowly melt overnight as the reaction warmed to ambient temperature. The reaction was then diluted with EtOAc (50 mL) and then washed with 1M HCl (50 mL, twice), half-saturated brine (50 mL) and saturated brine (50 mL). After drying over sodium sulfate, filtration and concentration in vacuo gave a residue which was applied to a silica gel column for purification, eluting with DCM:MeOH—99:1 to 90:10. The product containing factions were pooled and concentrated in vacuo to give a residue that was not of sufficient purity. This residue was applied to a second silica gel column for purification, eluting with DCM:MeOH—99:1 to 95:5. The product containing factions were pooled and concentrated in vacuo to give 30 mg of the title compound. MS: m/z=550 (M+23($Na^+$)). HRMS: m/z=528.2428; calculated m/z=528.2417 for $C_{27}H_{32}N_5O_4F_2$.

Example 4

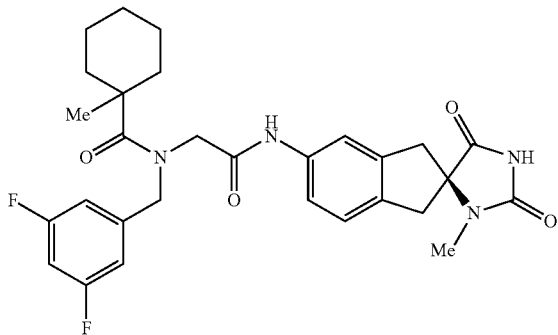 [SMILES: CN1C(=O)NC(=O)[C@@]12Cc1ccc(NC(=O)CN(Cc3cc(F)cc(F)c3)C(=O)C3(C)CCCCC3)cc1C2]

N-(3,5-difluorobenzyl)-1-methyl-N-(2-{[(4S)-3-methyl-2,5-dioxo-1',3'-dihydrospiro-[imidazolidine-4,2'-inden]-5'-yl]amino}-2-oxoethyl)cyclohexanecarboxamide To a solution of 1-methylcyclohexanecarboxylic acid (32.0 mg, 0.222 mmol) in DCM (1.5 mL) was added one drop of DMF (cat.), followed by oxalyl chloride (37.0 mg, 0.228 mmol), while at ambient temperature and under a constant stream of nitrogen. Upon cessation of gas evolution, the reaction mixture was cooled to 0° C. prior to the introduction of triethylamine (34.0 mg, 0.333 mmol) as a solution in DCM (2.0 mL), and then N-(3,5-difluorobenzyl)-2-{[(4S)-3-methyl-2,5-dioxo-1',3'-dihydrospiro[imidazolidine-4,2'-inden]-5'-yl]amino}-2-oxoethanaminium chloride (50.0 mg, 0.111 mmol, Intermediate 1). After 1 hour the reaction mixture was applied directly to a silica gel column for purification, eluting with DCM:MeOH—99:1 to 95:5. Product containing fractions were pooled and concentrated in vacuo to give the title compound. MS: m/z=561 (M+23(Na$^+$)). HRMS: m/z=539.2477; calculated m/z=539.2464 for $C_{29}H_{33}N_4O_4F_2$.

Example 5

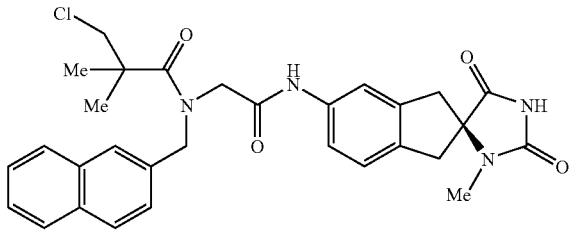 [SMILES: CN1C(=O)NC(=O)[C@@]12Cc1ccc(NC(=O)CN(Cc3ccc4ccccc4c3)C(=O)C(C)(C)CCl)cc1C2]

3-chloro-2,2-dimethyl-N-(2-{[(4S)-3-methyl-2,5-dioxo-1',3'-dihydrospiro[imidazolidine-4,2'-inden]-5'-yl]amino}-2-oxoethyl)-N-(2-naphthylmethyl)propanamide Step A. tert-butyl (2-{[(4S)-3-methyl-2,5-dioxo-1',3'-dihydrospiro[imidazolidine-4,2'-inden]-5'-yl]amino}-2-oxoethyl)carbamate To a dry mixture of [(tert-butoxycarbonyl)amino]acetic acid (4.17 g, 23.8 mmol), (4S)-5'-amino-3-methyl-1',3'-dihydro-2H,5H-spiro[imidazolidine-4,2'-indene]-2,5-dione (5.00 g, 21.6 mmol), EDCI (5.39 g, 28.1 mmol), and HOAt (2.94 g, 21.6 mmol) was added THF (100 mL) and DMF (20 mL), followed by triethylamine (3.28 g, 32.4 mmol). The reaction mixture was stirred at ambient temperature for 18 hours. The bulk of the solvent was removed in vacuo, and then the residue was partitioned between EtOAc (100 mL) and water (200 mL), forming a tri-phasic mixture. The lower aqueous layer was drained off without removing any of the solids. The organics were washed with half-saturated brine and then saturated brine. At this point the solids were removed by filtration, washed with EtOAc, air-dried and then placed under high vacuum, to provide the title compound. MS: m/z=389 (M+1).

Step B. 2-amino-N-[(4S)-3-methyl-2,5-dioxo-1',3'-dihydrospiro[imidazolidine-4,2'-inden]-5'-yl]acetamide To a suspension of tert-butyl (2-{[(4S)-3-methyl-2,5-dioxo-1',3'-dihydrospiro[imidazolidine-4,2'-inden]-5'-yl]amino}-2-oxoethyl)carbamate from Step A (1.80 g, 4.63 mmol) in EtOAc (50 mL), at 0° C., was added anhydrous HCl (bubbled in through a pipet, for 5 minutes). After an additional 30 minutes of standing at 0° C., the solvent and excess HCl was removed in vacuo to yield a solid. This solid was then dissolved in the minimal amount of MeOH and treated with a methanolic 2 N ammonia solution (20 mL, 40 mmol). This mixture was stirred for 30 min at ambient temperature, before the bulk of the MeOH was removed in vacuo. The residue was applied to a silica gel column for purification, eluting with DCM:MeOH (10% conc. NH$_4$OH)—95:5 to 85:15. Product containing fractions were pooled and concentrated in vacuo to give the title compound. MS: m/z=289 (M+1).

Step C. N-[(4S)-3-methyl-2,5-dioxo-1',3'-dihydrospiro[imidazolidine-4,2'-inden]-5'-yl]-2-[(2-naphthylmethyl)amino]acetamide A stirred solution of 2-amino-N-[(4S)-3-methyl-2,5-dioxo-1',3'-dihydrospiro[imidazolidine-4,2'-inden]-5'-yl]acetamide from Step B (80.0 mg, 0.277 mmol) and 2-naphthaldehyde (65.0 mg, 0.416 mmol), in MeOH (3 mL) was heated to 50° C. After 5 hours, no additional formation of the intermediate imine could be observed, so the reaction was cooled to 0° C., prior to the introduction of sodium borohydride (21.0 mg, 0.555 mmol). After 10 minutes the reaction was complete. The bulk of the solvent was remove in vacuo, and the resulting residue was applied to a silica gel column for purification, eluting with DCM:MeOH (10% conc. NH$_4$OH)—98:2 to 92:8. Product containing fractions were pooled and concentrated in vacuo to give the title compound. MS: m/z=429 (M+1).

Step D. 3-chloro-2,2-dimethyl-N-(2-{[(4S)-3-methyl-2,5-dioxo-1',3'-dihydrospiro[imidazolidine-4,2'-inden]-5'-yl]amino}-2-oxoethyl)-N-(2-naphthylmethyl)propanamide To a stirred solution of N-[(4S)-3-methyl-2,5-dioxo-1',3'-dihydrospiro[imidazolidine-4,2'-inden]-5'-yl]-2-[(2-naphthylmethyl)amino]acetamide from Step C (19 mg, 0.044 mmol), in DCM (1 mL), at 0° C. was added 3-chloro-2,2-dimethylpropanoyl chloride (10 mg, 0.067 mmol) and triethylamine (9.0 mg, 0.089 mmol). After 1 hour the reaction mixture was applied directly to a silica gel column for purification, eluting with DCM:MeOH—99:1 to 96:4. Product containing fractions were pooled and concentrated in vacuo to give the title compound. MS: m/z=547 (M($^{35}$Cl)+1). HRMS: m/z=547.2103; calculated m/z=547.2107 for $C_{30}H_{32}N_4O_5(^{35}Cl)_1$.

INTERMEDIATE 2

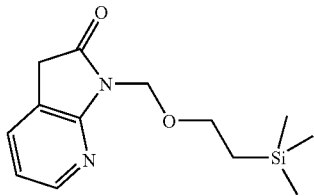

1-{[2-(Trimethylsilyl)ethoxy]methyl}-1,3-dihydro-2H-pyrrolo[2,3-b]pyridin-2-one

Step A. 1-{[2-(Trimethylsilyl)ethoxy]methyl}-1H-pyrrolo[2,3-b]pyridine

Sodium hydride (60% dispersion in mineral oil; 16.2 g, 0.404 mol) was added in portions over 25 min to a solution of 7-azaindole (39.8 g, 0.337 mol) in DMF (200 mL) at 0° C. and the mixture was stirred for 1 h. 2-(Trimethylsilyl)ethoxymethyl chloride (71.8 mL, 0.404 mol) was then added slowly over 15 min, keeping the temperature of the reaction mixture below 10° C. After 1 h, the reaction was quenched with water (500 mL) and the mixture was extracted with $CH_2Cl_2$ (5×300 mL) The combined organic layers were washed with saturated brine, dried over $MgSO_4$, filtered, concentrated and dried under high vacuum to give the title compound. MS: m/z=249 (M+1).

Step B. 3,3-Dibromo-1-{[2-(trimethylsilyl)ethoxy]methyl}-1,3-dihydro-2H-pyrrolo[2,3-b]pyridin-2-one A solution of 1-{[2-(trimethylsilyl)ethoxy]methyl}-1H-pyrrolo[2,3-b]pyridine from Step A (43.1 g, 0.1735 mol) in dioxane (300 mL) was added dropwise over 30 min to a suspension of pyridine hydrobromide perbromide (277 g, 0.8677 mol) in dioxane (300 mL). The reaction was stirred at ambient temperature using an overhead mechanical stirrer to produce two layers. After 60 min, the reaction was quenched with water (300 mL) and extracted with EtOAc (500 mL). The aqueous layer was extracted further with EtOAc (2×300 mL) and the combined organic layers were washed with $H_2O$ (4×300 mL; the final wash was pH 5-6), then brine (300 mL), dried over $MgSO_4$, filtered and concentrated in vacuo. The crude product was immediately dissolved in $CH_2Cl_2$ and the solution filtered through a plug of silica, eluting with $CH_2Cl_2$ until the dark red color had completely eluted from the plug. The filtrate was washed with saturated aqueous $NaHCO_3$ (400 mL), then brine (400 mL), dried over $MgSO_4$ filtered, and concentrated in vacuo to give the title compound. MS: m/z=423 (M+1).

Step C. 1-{[2-(Trimethylsilyl)ethoxy]methyl}-1,3-dihydro-2H-pyrrolo[2,3-b]pyridin-2-one Zinc (100 g, 1.54 mol) was added to a solution of 3,3-dibromo-1-{[2-(trimethylsilyl)ethoxy]methyl}-1,3-dihydro-2H-pyrrolo[2,3-b]pyridin-2-one (65 g, 0.154 mol) in THF (880 mL) and saturated aqueous $NH_4Cl$ (220 mL). After 3 h, the reaction mixture was filtered and concentrated in vacuo. The residue was partitioned between EtOAc and $H_2O$ which resulted in the formation of a white precipitate. Both layers were filtered through a Celite pad and the layers were separated. The aqueous layer was washed with EtOAc (2×500 mL) and the combined organic layers were washed with $H_2O$, dried over $MgSO_4$, filtered, and concentrated under reduced pressure. The crude product was purified by silica gel chromatography, eluting with $CH_2Cl_2$:EtOAc—90:10, to give the title compound. MS: m/z=265 (M+1).

INTERMEDIATE 3

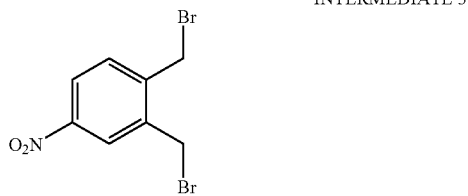

1,2-Bis(bromomethyl)-4-nitrobenzene

Step A. (4-Nitro-1,2-phenylene)dimethanol

A solution of 4-nitrophthalic acid (40 g, 189.5 mmol) in THF (500 mL) was added dropwise over 1.5 h to a solution of borane-THF complex (1 M, 490 mL, 490 mmol), keeping the reaction temperature between 0° C. and 5° C. After the addition, the reaction mixture was allowed to warm slowly to ambient temperature and stirred for 18 h. MeOH (100 mL) was added carefully and the precipitated solid dissolved. The mixture was concentrated in vacuo to about 500 mL, cooled to 0° C., and 10 N NaOH was added to adjust the pH to 10-11. This mixture was extracted with EtOAc (3×600 mL) and the combined organic layers were washed with brine, dried over $Na_2SO_4$, filtered, and concentrated in vacuo to give the title compound. MS: m/z=207 (M–OH+$CH_3CN$).

Step B. 1,2-Bis(bromomethyl)-4-nitrobenzene

Phosphorus tribromide (20.1 mL, 212 mmol) in $Et_2O$ (250 mL) was added dropwise over 1.5 h to a solution of (4-nitro-1,2-phenylene)dimethanol from Step A (35.3 g, 193 mmol) in $Et_2O$ (750 mL). After 18 h, the reaction mixture was cooled to 0° C. and quenched with $H_2O$ (100 mL). The layers were separated and the organic layer was washed with $H_2O$ (2×200 mL), then saturated aqueous $NaHCO_3$, dried over $Na_2SO_4$, filtered, and concentrated in vacuo to give the title compound. MS: m/z=309 (M+1).

INTERMEDIATE 4

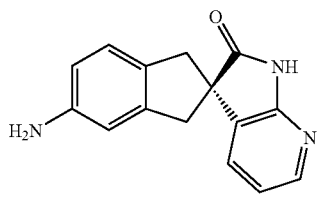

(R)-5-Amino-1,3-dihydrospiro[indene-2,3'-pyrrolo[2,3-b]pyridin]-2'(1'H)-one

Step A. (±)-5-Nitro-1'-{[2-(trimethylsilyl)ethoxy]methyl}-1,3-dihydro spiro[indene-2,3'-pyrrolo[2,3-b]pyridin]-2'(1'H)-one To a solution of 1,2-bis(bromomethyl)-4-nitrobenzene (40.9 g, 132 mmol, described in Intermediate 3) and 1-{[2-(trimethylsilyl)ethoxy]methyl}-1,3-dihydro-2H-pyrrolo[2,3-b]pyridin-2-one (31.5 g, 119 mmol, described in Intermediate 2) in DMF (2 L) was added cesium carbonate (129 g, 397 mmol), portionwise, over 5 min. After 18 h, acetic acid (7.6 mL) was added and the mixture was concentrated to a volume of about 500 mL, then partitioned between EtOAc (1.5 L) and H$_2$O (1 L). The organic layer was washed with H$_2$O (1 L), then brine (500 mL), then dried over Na$_2$SO$_4$, filtered, and concentrated in vacuo. The crude product was purified by silica gel chromatography, eluting with a gradient of hexane:EtOAc—100:0 to 0:100, to give the title compound. MS: m/z=412 (M+1).

Step B. (±)-5-Amino-1'-{[2-(trimethylsilyl)ethoxy]methyl}-1,3-dihydrospiro[indene-2,3'-pyrrolo[2,3-b]pyridin]-2'(1'H)-one A mixture of 10% Pd/C (3 g) and (±)-5-nitro-1'-{[2-(trimethylsilyl)ethoxy]methyl}-1,3-dihydrospiro[indene-2,3'-pyrrolo[2,3-b]pyridin]-2'(1'H)-one from Step A (19.1 g, 46.4 mmol) was stirred vigorously in EtOH (400 mL) under an atmosphere of hydrogen (ca. 1 atm). After 18 h, the mixture was filtered through a pad of Celite, washing extensively with MeOH, and the filtrate was concentrated in vacuo to give the title compound. MS: m/z=382 (M+1).

Step C. tert-Butyl(R)-(2'-oxo-1'-{[2-(trimethylsilyl)ethoxy]methyl}-1,1',2',3-tetrahydrospiro[indene-2,3'-pyrrolo[2,3-b]pyridin]-5-yl)carbamate A solution of (±)-5-amino-1'-{[2-(trimethylsilyl)ethoxy]methyl}-1,3-dihydrospiro[indene-2,3'-pyrrolo[2,3-b]pyridin]-2'(1'H)-one from Step B (104 g, 273 mmol) and di-tert-butyl dicarbonate (71.5 g, 328 mmol) in CHCl$_3$ (1 L) was heated to reflux for 17 h. The cooled mixture was concentrated in vacuo and the residue was purified by silica gel chromatography, eluting with hexane:EtOAc—100:0 to 50:50, to give the racemic product. The enantiomers were resolved by HPLC, utilizing a ChiralPak AD column and eluting with EtOH. The first major peak to elute was tert-butyl (S)-(2'-oxo-1'-{[2-(trimethylsilyl)ethoxy]methyl}-1,1',2',3-tetrahydrospiro[indene-2,3'-pyrrolo[2,3-b]pyridin]-5-yl)carbamate, and the second major peak to elute was tert-butyl(R)-(2'-oxo-1'-{[2-(trimethylsilyl)ethoxy]methyl}-1,1',2',3-tetrahydrospiro[indene-2,3'-pyrrolo[2,3-b]pyridin]-5-yl)carbamate, the title compound. MS: m/z=482 (M+1).

Step D. (R)-5-Amino-1,3-dihydro spiro[indene-2,3'-pyrrolo[2,3-b]pyridin]-2'(1'H)-one A solution of tert-butyl(R)-(2'-oxo-1'-{[2-(trimethylsilyl)ethoxy]methyl}-1,1',2',3-tetrahydrospiro[indene-2,3'-pyrrolo[2,3-b]pyridin]-5-yl)carbamate from Step C (13.4 g, 27.8 mmol) in MeOH (300 mL) was saturated with HCl (g). The mixture was resaturated with HCl (g) every 30 min until the starting material was consumed, and then concentrated in vacuo. The residue was dissolved in MeOH (150 mL) and treated with ethylenediamine (1.9 mL, 27.8 mmol) and 10 N sodium hydroxide (6 mL, 60 mmol) to adjust the mixture to pH 10. After 30 min, the mixture was diluted with H$_2$O (400 mL) and extracted with CHCl$_3$ (1 L). The organic layer was dried over Na$_2$SO$_4$, filtered, and concentrated in vacuo. The crude material was triturated with MeOH (35 mL) to give the title compound. MS: m/z=252 (M+1).

The examples appearing in the following tables were prepared by analogy to the above examples and intermediates, as described or prepared as a result of similar transformations with modifications known to those skilled in the art. The requisite starting materials and intermediates were described herein (vide supra), commercially available, known in the literature, or readily synthesized by one skilled in the art. In some cases, additional synthetic transformations that are well known to those skilled in the art were utilized after the key amide coupling to provide other products of interest. Straightforward protecting group strategies were applied in some routes. Some of the examples described in the tables were synthesized as mixtures of stereoisomers and subsequently purified to give individual isomers.

TABLE 1

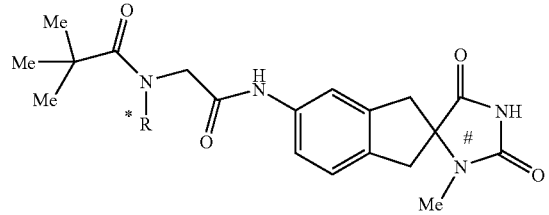

| Example | R | * | # | LCMS (M + 1) |
|---|---|---|---|---|
| 6 | Me | | ± | 387 |
| 7 | prop-2-yn-1-yl | | ± | 411 |
| 8 | 2,2-dimethylpropyl | | ± | 443 |
| 9 | tetrahydro-2H-pyran-4-ylmethyl | | ± | 471 |
| 10 | 2-ethylbutyl | | ± | 457 |
| 11 | tetrahydro-2H-pyran-2-ylmethyl | ± | ± | 471 |
| 12 | (5-methylisoxazol-3-yl)methyl | | S | 467 |
| 13 | 1-methylpentyl | R | S | 457 |

TABLE 2

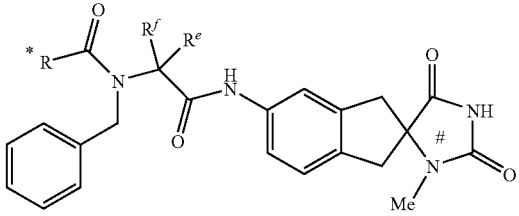

| Example | R | * | R$^e$, R$^f$ | # | LCMS (M + 1) |
|---|---|---|---|---|---|
| 14 | 2-(benzyloxy)-1,1-dimethylethyl | | H, H | ± | 569 |
| 15 | 2-hydroxy-1,1-dimethylethyl | | H, H | ± | 479 |
| 16 | 2-(benzyloxy)-1,1-dimethylethyl | | H, H | S | 569 |
| 17 | 2-(acetyloxy)-1,1-dimethylethyl | | H, H | ± | 507 |
| 18 | methoxycarbonyl | | H, H | ± | 465 |
| 19 | cyclopropyl | | H, H | ± | 447 |
| 20 | 2-(benzyloxy)-1,1-dimethylethyl | | H, H | R | 569 |
| 21 | methoxymethyl | | H, H | ± | 451 |
| 22 | 2-chloro-1,1-dimethylethyl | | H, H | ± | 497 |
| 23 | 1-methyl-1-(methylthio)ethyl | | H, H | ± | 495 |
| 24 | 1-methyl-1-(methylsulfinyl)ethyl | ± | H, H | ± | 511 |
| 25 | 1-methyl-1-(methylsulfonyl)ethyl | | H, H | ± | 527 |
| 26 | 2-chloro-1,1-dimethylethyl | | H, H | S | 497 |
| 27 | 1-[(tert-butoxycarbonyl)amino]-1-methylethyl | | H, H | ± | 564 |
| 28 | 1-amino-1-methylethyl | | H, H | ± | 464 |
| 29 | 1-hydroxy-1-methylethyl | | H, H | ± | 465 |
| 30 | 1,1-dimethyl-2-phenylethyl | | H, H | ± | 539 |

TABLE 2-continued

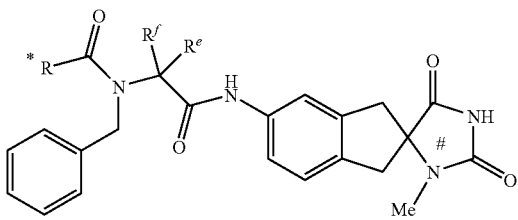

| Example | R | * | $R^e, R^f$ | # | LCMS (M + 1) |
|---|---|---|---|---|---|
| 31 | tert-butyl | | —CH₂CH₂— | ± | 489 |
| 32 | hydroxymethyl | | H, H | ± | 437 |
| 33 | (methylthio)methyl | | H, H | ± | 467 |
| 34 | 1-methylcyclopropyl | | H, H | S | 461 |
| 35 | 1-(trifluoromethyl)cyclopropyl | | H, H | S | 515 |
| 36 | 1-(trifluoromethyl)cyclobutyl | | H, H | S | 529 |

TABLE 3

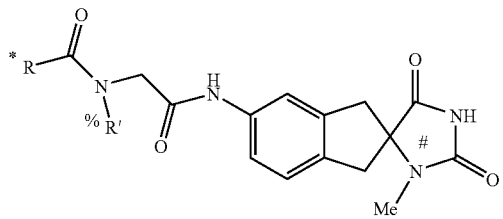

| Example | R | * | R' | % | # | LCMS (M + 1) |
|---|---|---|---|---|---|---|
| 37 | 2-hydroxy-1,1-dimethylethyl | | phenyl | | ± | 465 |
| 38 | phenyl | | tert-butyl | | ± | 449 |
| 39 | 2,2,2-trifluoro-1-hydroxy-1-methylethyl | S | 2,3-dihydro-1H-inden-1-yl | R | S | 545 |
| 40 | 1-(benzyloxy)-2,2,2-trifluoro-1-methylethyl | S | cycloheptyl | | S | 615 |
| 41 | 2,2,2-trifluoro-1-hydroxy-1-methylethyl | S | cycloheptyl | | S | 525 |

TABLE 4

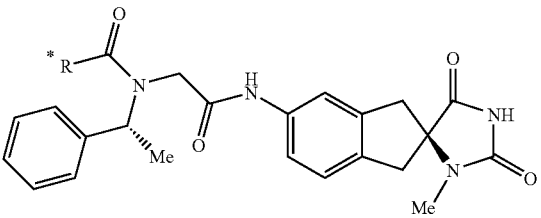

| Example | R | * | LCMS (M + 1) |
|---|---|---|---|
| 42 | 1-(trifluoromethyl)cyclopropyl | | 529 |
| 43 | 1-(trifluoromethyl)cyclobutyl | | 543 |
| 44 | 2,2-dichloro-1-methylcyclopropyl | ± | 534 |
| 45 | cyclobutyl | | 475 |
| 46 | dichloromethyl | | 503 |
| 47 | bromo(difluoro)methyl | | 549 |
| 48 | trichloromethyl | | 537 |
| 49 | 1-phenylcyclopropyl | | 537 |
| 50 | 1-methyl-1-phenylethyl | | 539 |

TABLE 4-continued

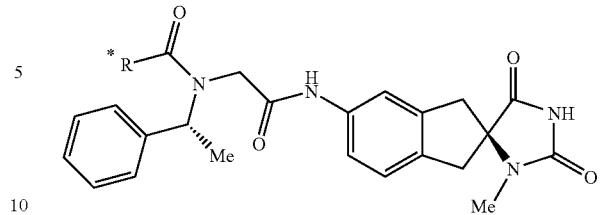

| Example | R | * | LCMS (M + 1) |
|---|---|---|---|
| 51 | 1-methylcyclohexyl | | 517 |
| 52 | 2,2,3,3-tetramethylcyclopropyl | | 517 |
| 53 | 1-cyanocyclopropyl | | 486 |
| 54 | 1,1-dichloro-2,2,2-trifluoroethyl | | 571 |
| 55 | 1-phenylcyclopentyl | | 565 |
| 56 | 2-chloro-1,1,2,2-tetrafluoroethyl | | 555 |
| 57 | 1-bromo-1-methylethyl | | 541 |
| 58 | 1,1-dimethylprop-2-yn-1-yl | | 487 |
| 59 | 1-phenylcyclohexyl | | 579 |
| 60 | 1-phenylethyl | | 525 |
| 61 | 1-methylcyclpropyl | | 475 |
| 62 | cyclopropylmethyl | | 475 |
| 63 | 1-adamantyl | | 555 |
| 64 | bicyclo[2.2.2]oct-1-yl | | 529 |
| 65 | 2-adamantyl | | 555 |
| 66 | tetrahydro-2H-pyran-4-yl | | 505 |
| 67 | 3-methyl-2-thienyl | | 517 |
| 68 | 3,5-dimethylisoxazol-4-yl | | 516 |
| 69 | tetrahydro-2H-pyran-3-yl | ± | 505 |
| 70 | 3-tent-butyl-1-methyl-1H-pyrazol-5-yl | | 557 |
| 71 | 5-tert-butyl-2-methyl-3-furyl | | 557 |
| 72 | 1-tert-butyl-3-methyl-1H-pyrazol-5-yl | | 557 |
| 73 | 2,2-dimethyltetrahydro-2H-pyran-4-yl | ± | 533 |

TABLE 5

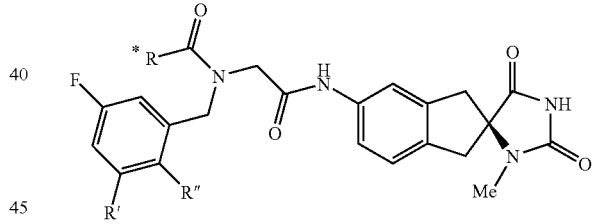

| Example | R | * | R' | R" | LCMS (M + 1) |
|---|---|---|---|---|---|
| 74 | 1-(trifluoromethyl)cyclobutyl | | F | H | 565 |
| 75 | 1-(trifluoromethyl)cyclopropyl | | F | H | 551 |
| 76 | bicyclo[2.2.1]hept-1-yl | | F | H | 537 |
| 77 | 1-hydroxycyclohexyl | | F | H | 541 |
| 78 | 2-methyltetrahydrofuran-2-yl | ± | F | H | 527 |
| 79 | 2-methyltetrahydrofuran-2-yl | S | F | H | 527 |
| 80 | 2,2-dimethyl-5-oxotetrahydrofuran-3-yl | ± | F | H | 555 |
| 81 | 5-oxopyrrolidin-2-yl | ± | F | H | 526 |
| 82 | tetrahydrofuran-3-yl | ± | F | H | 513 |
| 83 | 1-(trifluoromethyl)cyclopropyl | | F | F | 569 |
| 84 | 1-(trifluoromethyl)cyclobutyl | | F | F | 583 |
| 85 | 2-methyltetrahydrofuran-2-yl | R | F | H | 527 |
| 86 | 1-(trifluoromethyl)cyclopentyl | | F | H | 579 |
| 87 | 1-(benzyloxy)-2,2,2-trifluoro-1-methylethyl | R | F | H | 645 |
| 88 | 2,2,2-trifluoro-1-hydroxy-1-methylethyl | R | F | H | 555 |
| 89 | 1-(benzyloxy)-2,2,2-trifluoro-1-methylethyl | S | F | H | 645 |
| 90 | 2,2,2-trifluoro-1-hydroxy-1-methylethyl | S | F | H | 555 |

TABLE 5-continued

| Example | R | * | R' | R" | LCMS (M + 1) |
|---|---|---|---|---|---|
| 91 | 2,2,2-trifluoro-1-(hydroxymethyl)ethyl | ± | F | H | 555 |
| 92 | 1-(methoxycarbonyl)cyclopropyl | | F | H | 541 |
| 93 | 1-carboxycyclopropyl | | F | H | 527 |
| 94 | 1-(trifluoromethyl)cyclohexyl | | F | H | 593 |
| 95 | 2,2,3,3,3-pentafluoro-1-hydroxy-1-methylpropyl | S | F | H | 605 |
| 96 | 1-methylpiperidin-4-yl | | F | H | 540 |
| 97 | 1-methylpiperidin-3-yl | S | F | H | 540 |
| 98 | 1-methylpiperidin-3-yl | R | F | H | 540 |
| 99 | 1-methylpiperidin-2-yl | ± | F | H | 540 |
| 100 | 2,2,3,3,3-pentafluoro-1-hydroxy-1-methylpropyl | R | F | H | 605 |
| 101 | 4-methylpiperidin-4-yl | | F | H | 540 |
| 102 | 1,4-dimethylpiperidin-4-yl | | F | H | 554 |

TABLE 6

| Example | R | * | R' | R" | % | Z | LCMS (M + 1) |
|---|---|---|---|---|---|---|---|
| 103 | 1-(trifluoromethyl)cyclopropyl | | F | H | R | Me | 565 |
| 104 | 1-(trifluoromethyl)cyclobutyl | | F | H | R | Me | 579 |
| 105 | 1-methylcyclohexyl | | F | H | R | Me | 553 |
| 106 | 1-(trifluoromethyl)cyclopropyl | | F | F | R | Me | 583 |
| 107 | 1-(trifluoromethyl)cyclopropyl | | H | F | R | Me | 565 |
| 108 | 1-(trifluoromethyl)cyclopropyl | | H | F | S | Me | 565 |
| 109 | 2,2,2-trifluoro-1-hydroxy-1-methylethyl | S | F | H | R | Me | 569 |
| 110 | 2,2,2-trifluoro-1-hydroxy-1-methylethyl | S | F | H | R | n-Pr | 597 |

TABLE 7

| Example | R | * | R' | # | LCMS (M + 1) |
|---|---|---|---|---|---|
| 111 | Dimethylamino | | H | ± | 450 |
| 112 | Dimethylamino | | F | S | 486 |
| 113 | tert-butylamino | | F | S | 514 |
| 114 | 2-azabicyclo[2.2.1]hept-2-yl | ± | H | S | 502 |
| 115 | 2-oxa-5-azabicyclo[2.2.1]hept-5-yl | ± | H | S | 504 |
| 116 | Isopropylamino | | F | S | 500 |
| 117 | isopropyl(methyl)amino | | F | S | 514 |
| 118 | (2,2,2-trifluoroethyl)amino | | F | S | 540 |

TABLE 8

| Example | R | R' | # | LCMS (M + 1) |
|---|---|---|---|---|
| 119 | tert-butyl | Bn | ± | 479 |
| 120 | Me | Bn | ± | 437 |
| 121 | tert-butyl | Bn | S | 479 |
| 122 | tert-butyl | Me | ± | 403 |
| 123 | isopropyl | Bn | ± | 465 |

The compounds appearing in Tables 9 through 11 were prepared by analogy to the previous examples with the exception that (R)-5-Amino-1,3-dihydrospiro[indene-2,3'-pyrrolo[2,3-b]pyridin]-2'(1'H)-one (Intermediate 4) was used in place of 5'-amino-3-methyl-1',3'-dihydro-2H,5H-spiro[imidazolidine-4,2'-indene]-2,5-dione.

TABLE 9

| Example | R | * | R' | LCMS (M + 1) |
|---|---|---|---|---|
| 124 | 1-(trifluoromethyl)cyclobutyl | | F | 603 |
| 125 | 1-(trifluoromethyl)cyclopropyl | | F | 589 |
| 126 | tert-butoxy | | H | 535 |

TABLE 9-continued

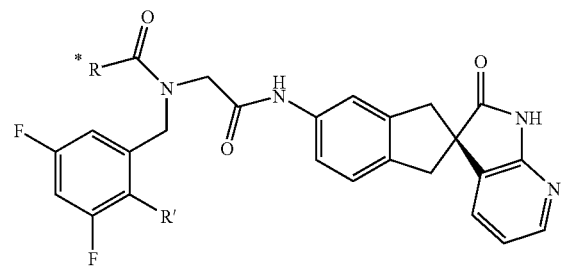

| Example | R | * | R' | LCMS (M + 1) |
|---|---|---|---|---|
| 127 | 1-(trifluoromethyl)cyclopropyl | | H | 571 |
| 128 | 1-(trifluoromethyl)cyclobutyl | | H | 585 |
| 129 | 2,2,2-trifluoro-1-hydroxy-1-methylethyl | R | H | 575 |
| 130 | 2,2,2-trifluoro-1-hydroxy-1-methylethyl | S | H | 575 |
| 131 | piperidin-3-yl | ± | H | 546 |
| 132 | piperidin-2-yl | ± | H | 546 |
| 133 | 4-methylpiperidin-4-yl | | H | 560 |
| 134 | 1,4-dimethylpiperidin-4-yl | | H | 574 |
| 135 | 1-azabicyclo[2.2.2]oct-3-yl | ± | H | 572 |
| 136 | 3-methylpyrrolidin-3-yl | ± | H | 546 |
| 137 | 1,3-dimethylpyrrolidin-3-yl | ± | H | 560 |
| 138 | 3-methylpiperidin-3-yl | ± | H | 560 |
| 139 | 1,3-dimethylpiperidin-3-yl | ± | H | 574 |

TABLE 10

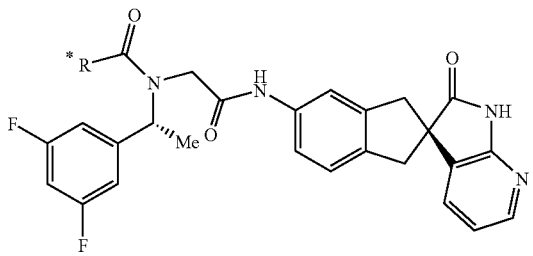

| Example | R | * | LCMS (M + 1) |
|---|---|---|---|
| 140 | tert-butoxy | | 549 |
| 141 | 1-(trifluoromethyl)cyclopropyl | | 585 |
| 142 | 1-(trifluoromethyl)cyclobutyl | | 599 |
| 143 | 2,2,2-trifluoro-1-hydroxy-1-methylethyl | S | 589 |
| 144 | 4-methylpiperidin-4-yl | | 574 |
| 145 | 1,4-dimethylpiperidin-4-yl | | 588 |

TABLE 11

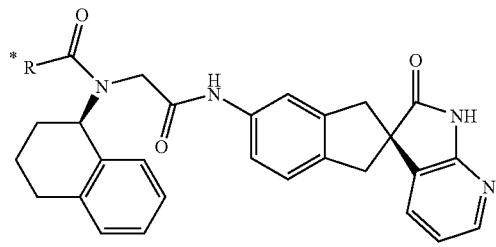

| Example | R | * | LCMS (M + 1) |
|---|---|---|---|
| 146 | 1-(tert-butoxycarbonyl)-3-methylpiperidin-3-yl | ± | 664 |
| 147 | 1-(tert-butoxycarbonyl)-4-methylpiperidin-4-yl | | 664 |

TABLE 11-continued

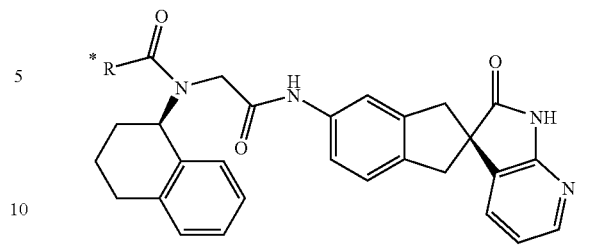

| Example | R | * | LCMS (M + 1) |
|---|---|---|---|
| 148 | 3-methylpiperidin-3-yl | ± | 564 |
| 149 | 3-methylpiperidin-3-yl | S | 564 |
| 150 | 4-methylpiperidin-4-yl | | 564 |
| 151 | 3-methylpiperidin-3-yl | R | 564 |

Although specific enantiomers and diastereomers appear in the above Examples and Intermediates, it is well understood by those skilled in the art that modifications to reaction conditions and reagents (for example, but not limited to: using the opposite chirality for starting materials; different catalysts; using the opposite chirality for reagents; choosing to use a different enantiomer or diastereomer subsequent to a chiral resolution) will provide alternative enantiomers and diastereomers, all of which are included in the spirit and scope of the invention. It is intended that all of the possible optical isomers and diastereomers in mixtures and as pure or partially purified compounds are included within the ambit of this invention. The present invention is meant to comprehend all such isomeric forms of these compounds.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of the formula Ii:

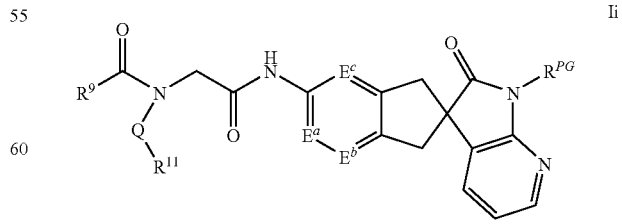

Ii wherein:
Q is independently selected from:
(1) —$CH_2$—,
(2) —$CHR^d$—

(3) —C(R$^d$)$_2$—,
(4) —C(halo)R$^a$—, and
(5) —C(halo)$_2$—;
E$^a$ is —C(R$^{5a}$)═,
E$^b$ is —C(R$^{5b}$)═,
E$^c$ is —C(R$^{5c}$)═,
R$^{5a}$, R$^{5b}$ and R$^{5c}$ are each hydrogen,
R$^9$ is selected from:
—C$_3$cycloalkyl, or C$_4$cycloalkyl, unsubstituted or substituted with 1-5 substituents each independently selected from:
(a) halo,
(b) —OR$^a$,
(c) —CN,
(d) —CO$_2$R$^a$,
(e) —C$_{1-6}$alkyl, which is unsubstituted or substituted with 1-6 halo,
(f) —NR$^b$R$^c$,
(g) —C≡CR$^a$,
(h) phenyl or heterocycle, wherein the heterocycle is selected from: pyridyl, pyrimidinyl, pyrazinyl, pyridazinyl, piperidyl, piperazinyl, pyrrolidinyl, thienyl, morpholinyl, thiazolyl, oxazolyl, isoxazolyl, furanyl, tetrahydrofuranyl, and tetrahydropyranyl, which phenyl or heterocycle is unsubstituted or substituted with 1-5 substituents each independently selected from:
(i) halo,
(ii) —OR$^a$,
(iii) —CN,
(iv) —CO$_2$R$^a$,
(v) —C$_{1-6}$alkyl, which is optionally substituted with 1-6 halo,
R$^{11}$ is independently selected from the group consisting of: C$_{5-8}$cycloalkyl, phenyl, tetrahydronaphthyl, and indanyl, where R$^{11}$ is unsubstituted or substituted with 1-5 substituents each independently selected from halo,
R$^{PG}$ is hydrogen,
R$^a$ is independently selected from:
(1) hydrogen,
(2) C$_{1-6}$alkyl, which is unsubstituted or substituted with 1-7 substituents each independently selected from:
(a) halo,
(b) —O—C$_{1-6}$alkyl, which is unsubstituted or substituted with 1-6 halo,
(c) hydroxyl,
(d) —CN, and
(e) phenyl or heterocycle wherein heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl, and pyrazinyl, which phenyl or heterocycle is unsubstituted or substituted with 1-3 substituents each independently selected from:
(i) halo,
(ii) —O—C$_{1-6}$alkyl, which is unsubstituted or substituted with 1-6 halo,
(iii) —CN,
(iv) nitro,
(v) hydroxyl, and
(vi) —C$_{1-6}$alkyl, which is unsubstituted or substituted with 1-6 halo,
(3) phenyl or heterocycle wherein heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl, and pyrazinyl, which phenyl or heterocycle is unsubstituted or substituted with 1-3 substituents each independently selected from:
(a) halo,
(b) —CN,
(c) —O—C$_{1-6}$alkyl, which is unsubstituted or substituted with 1-6 halo,
(d) nitro,
(e) hydroxyl, and
(f) —C$_{1-6}$alkyl, which is unsubstituted or substituted with 1-6 halo,
(4) —C$_{3-6}$cycloalkyl, which is unsubstituted or substituted with 1-6 halo;
R$^b$ and R$^c$ are each independently selected from:
(1) hydrogen,
(2) C$_{1-6}$alkyl, which is unsubstituted or substituted with 1-7 substituents each independently selected from:
(a) halo,
(b) —OR$^a$,
(c) —CN,
(d) —CO$_2$R$^a$, and
(e) phenyl or heterocycle wherein heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl, and pyrazinyl, which phenyl or heterocycle is unsubstituted or substituted with 1-3 substituents each independently selected from:
(i) halo,
(ii) —OR$^a$,
(iii) —C$_{1-6}$alkyl, which is unsubstituted or substituted with 1-6 halo, and
(iv) nitro,
(3) phenyl or heterocycle wherein heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl, and pyrazinyl, which phenyl or heterocycle is unsubstituted or substituted with 1-3 substituents each independently selected from:
(a) halo,
(b) —OR$^a$,
(c) —C$_{1-6}$alkyl, which is unsubstituted or substituted with 1-6 halo,
(d) —C$_{3-6}$cycloalkyl, which is unsubstituted or substituted with 1-6 halo,
(e) —CN, and
(f) —CO$_2$R$^a$,
(4) —C$_{3-6}$cycloalkyl, which is unsubstituted or substituted with 1-6 halo;
or where R$^b$ and R$^c$ and the nitrogen to which they are attached join to form a 4-, 5-, or 6-membered ring, optionally containing an additional heteroatom selected from N, O, and S wherein the sulfur is optionally oxidized to the sulfone or sulfoxide, which ring is unsubstituted or substituted with 1-4 substituents each independently selected from:
(a) halo,
(b) —OR$^a$, and
(c) —C$_{1-6}$alkyl, which is unsubstituted or substituted with 1-6 halo, and
(d) phenyl;

$R^d$ is independently selected from:
   (1) $C_{1-6}$alkyl, which is unsubstituted or substituted with 1-4 substituents each independently selected from:
      (a) halo,
      (b) —$OR^a$,
      (c) —$CO_2R^a$,
      (d) —CN, and
      (e) phenyl or heterocycle, wherein heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl, and pyrazinyl, which phenyl or heterocycle is unsubstituted or substituted with 1-3 substituents each independently selected from:
         (i) halo,
         (ii) —$OR^a$,
         (iii) —$C_{1-6}$alkyl, which is unsubstituted or substituted with 1-6 halo, and
         (iv) nitro,
   (2) phenyl or heterocycle, wherein heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl, and pyrazinyl, which phenyl or heterocycle is unsubstituted or substituted with 1-3 substituents each independently selected from:
      (a) halo,
      (b) —$OR^a$,
      (c) —$C_{1-6}$alkyl, which is unsubstituted or substituted with 1-6 halo,
      (d) —$C_{3-6}$cycloalkyl, which is unsubstituted or substituted with 1-6 halo
      (e) —CN, and
      (f) —$CO_2R^a$,
   (3) —$C_{3-6}$cycloalkyl, which is unsubstituted or substituted with 1-6 halo;
or a pharmaceutically acceptable salt thereof and individual enantiomers and diastereomers thereof.

2. The compound of claim 1, wherein:
Q is independently selected from: —$CH_2$—, —$CHR^d$—, and —$C(R^d)_2$—;
or a pharmaceutically acceptable salt thereof and individual enantiomers and diastereomers thereof.

3. A compound selected from:

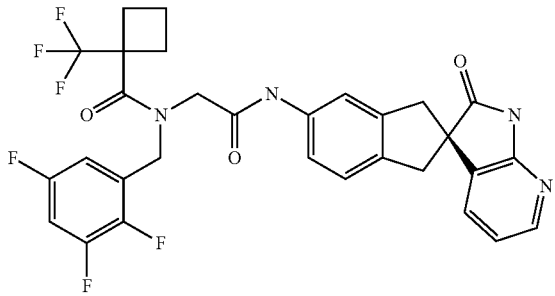

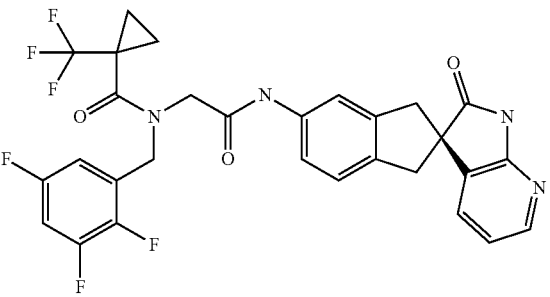

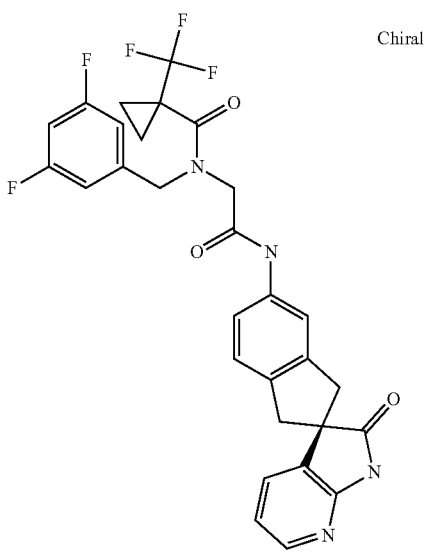

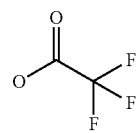

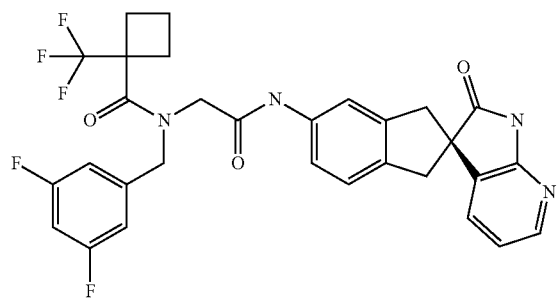

87
-continued
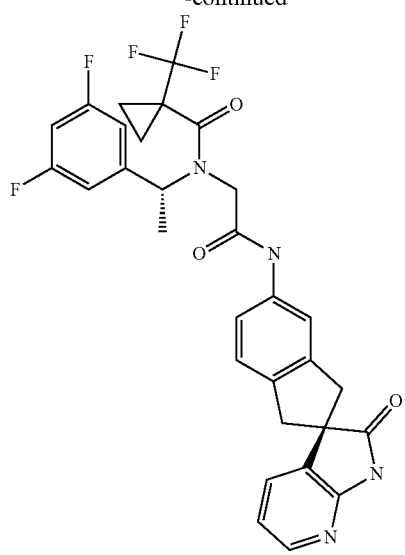
88
-continued
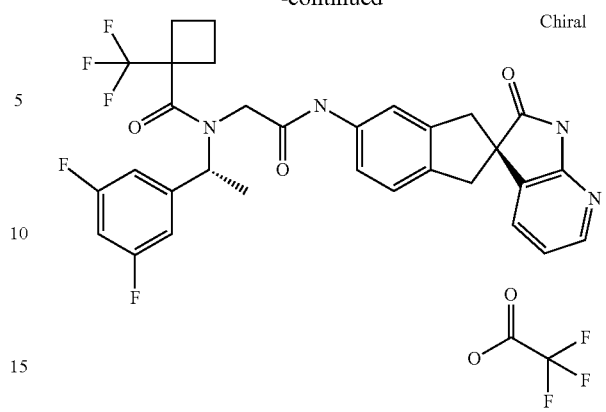
or a pharmaceutically acceptable salt thereof and individual enantiomers and diastereomers thereof.
4. A pharmaceutical composition which comprises an inert carrier and the compound of claim 1.
* * * * *

UNITED STATES PATENT AND TRADEMARK OFFICE
CERTIFICATE OF CORRECTION

PATENT NO. : 8,372,859 B2
APPLICATION NO. : 12/594993
DATED : February 12, 2013
INVENTOR(S) : Wood et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 587 days.

Signed and Sealed this
Twentieth Day of August, 2013

Teresa Stanek Rea
*Acting Director of the United States Patent and Trademark Office*